(12) United States Patent
Anderson et al.

(10) Patent No.: US 12,054,789 B2
(45) Date of Patent: Aug. 6, 2024

(54) CAPTURING, CONCENTRATING, AND DETECTING MICROBES IN A SAMPLE USING MAGNETIC IONIC LIQUIDS AND RECOMBINASE POLYMERASE AMPLIFICATION

(71) Applicant: Iowa State University Research Foundation, Inc., Ames, IA (US)

(72) Inventors: Jared L. Anderson, Ames, IA (US); Byron F. Brehm-Stecher, Ames, IA (US); Kevin D. Clark, Ames, IA (US); Stephanie A. Hice, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 870 days.

(21) Appl. No.: 16/792,734

(22) Filed: Feb. 17, 2020

(65) Prior Publication Data
US 2020/0325525 A1 Oct. 15, 2020

Related U.S. Application Data

(60) Provisional application No. 62/834,169, filed on Apr. 15, 2019.

(51) Int. Cl.

| | | |
|---|---|---|
| *C12Q 1/68* | (2018.01) | |
| *C07F 5/00* | (2006.01) | |
| *C07F 13/00* | (2006.01) | |
| *C07F 15/04* | (2006.01) | |
| *C07F 15/06* | (2006.01) | |
| *C12N 1/02* | (2006.01) | |
| *C12N 1/20* | (2006.01) | |
| *C12N 15/10* | (2006.01) | |
| *C12Q 1/04* | (2006.01) | |
| *C12Q 1/24* | (2006.01) | |
| *C12Q 1/6806* | (2018.01) | |
| *C12Q 1/689* | (2018.01) | |

(52) U.S. Cl.
CPC .............. *C12Q 1/689* (2013.01); *C07F 5/003* (2013.01); *C07F 13/005* (2013.01); *C07F 15/045* (2013.01); *C07F 15/065* (2013.01); *C12N 1/02* (2013.01); *C12N 1/20* (2013.01); *C12N 15/1013* (2013.01); *C12Q 1/04* (2013.01); *C12Q 1/24* (2013.01); *C12Q 1/6806* (2013.01)

(58) Field of Classification Search
CPC . C12Q 1/689; C12Q 1/04; C12Q 1/24; C12Q 1/6806; C07F 5/003; C07F 13/005; C07F 15/045; C07F 15/065; C12N 1/02; C12N 1/20; C12N 15/1013
See application file for complete search history.

(56) References Cited

U.S. PATENT DOCUMENTS

| 10,280,416 B1 | 5/2019 | Anderson et al. |
| 11,046,991 B2 * | 6/2021 | Anderson ........ G01N 33/48735 |
| 2018/0298417 A1 * | 10/2018 | Anderson ............... H01F 1/447 |

OTHER PUBLICATIONS

Santos et al. RSC Advances, 2014, 4, 40008-40018 (Year: 2014).*
Zhao et al. Journal of Virological Methods 263, Jan. 2019, 96-100 (Year: 2019).*
Silva et al. Journal of Virological Methods 222 (2015) 138-144 (Year: 2015).*
Yeh et al. "Self-powered integrated microfluidic point-of-care low-cost enabling (SIMPLE) chip" Science Advances Mar. 22, 2017; 3:e1501645; pp. 1-11. (Year: 2017).*
Merib et al., "Magnetic ionic liquids as versatile extraction phases for the rapid determination of estrogens in human urine by dispersive liquid-liquid microextraction coupled with high-performance liquid chromatography-diode array detection", Analytical and Bioanalytical Chemistry, vol. 410, pp. 4689-4699, 2018.
Mester et al., "Use of Ionic Liquid-Based Extraction for Recovery of *Salmonella typhimurium* and Listeria monocytogenes from Food Matrices", Journal of Food Protection, vol. 73, No. 4, pp. 680-687, 2010.
Morton et al., "Phage Display-Derived Binders Able to Distinguish Listeria monocytogenes from Other *Listeria* Species", PLOS One, vol. 8, Issue 9, 11 pages, Sep. 2013.
Murinda et al., "Real-Time Isothermal Detection of Shiga Toxin-Producing *Escherichia coli* Using Recombinase Polymerase Amplification", Foodborne Pathogens and Disease, vol. 11, No. 7, pp. 529-536, 2014.
Murphy, Steven C., "Shelf-Life of Fluid Milk Products—Microbial Spoilage—The Evaluation of Shelf-Life", Cornell University, Dairy Foods Science Notes, 5 pages, Jun. 30, 2009.
Nikaido, Hiroshi, "Molecular Basis of Bacterial Outer Membrane Permeability Revisited", Microbiology and Molecular Biology Reviews, vol. 67, No. 4, pp. 593-656, Dec. 2003.
Oliver, James D., "The Viable but Nonculturable State in Bacteria", Journal of Microbiology, vol. 43, No. S, pp. 93-100, Feb. 2005.
Omiccioli et al., "A new platform for Real-Time PCR detection of *Salmonella* spp., Listeria monocytogenes and *Escherichia coli* O157 in milk", Food Microbiology, vol. 26, pp. 615-622, Apr. 19, 2009.
Park et al., "Identification of *Salmonella enterica* subspecies I, *Salmonella enterica* serovars Typhimurium, Enteritidis and Typhi using multiplex PCR", FEMS Microbial Letters, vol. 301, pp. 137-146, Sep. 24, 2009.
Piepenburg et al., "DNA Detection Using Recombination Proteins", PLoS Biology, vol. 4, Issue 7, pp. 1115-1121, Jul. 2006.

(Continued)

*Primary Examiner* — Jezia Riley
(74) *Attorney, Agent, or Firm* — McKee, Voorhees & Sease, PLC

(57) ABSTRACT

In this disclosure, a method or kit for using the method of extracting, concentrating, and detecting microbes from a sample is disclosed. The method disclosed herein use transition or rare earth metal-based magnetic ionic liquids (MILs) to extract viable microbes from a sample and to detect them via an amplification-based method and/or a non-amplification-based methods. The method and kit can be used in-field and on-site for detection of viable microbes in a sample within about an hour, without using any powered heat source or powered tool.

12 Claims, 12 Drawing Sheets
Specification includes a Sequence Listing.

(56) References Cited

OTHER PUBLICATIONS

Pierson et al., "Synthesis and characterization of low viscosity hexafluoroacetylacetonate-based hydrophobic magnetic ionic liquids", New J. Chem., vol. 41, pp. 5498-5505, May 25, 2017.
Posthuma-Trumpie et al., "Lateral flow (immuno)assay: its strengths, weaknesses, opportunities and threats. A literature survey", Anal. Bioanal. Chem., vol. 393, pp. 569-582, 2009.
Rossmanith et al., "The use of chromogenic bacteria as coloured substitutes for pathogens: A simple strategy during design and development of a new method for sample pretreatment", Letters in Applied Microbiology, vol. 50, pp. 230-233, 2010.
Rossmanith et al., "Development of matrix lysis for concentration of gram positive bacteria from food and blood", Journal of Microbiological Methods, vol. 69, pp. 504-511, Mar. 13, 2007.
Fabre et al., "CRISPR Is an Optimal Target for the Design of Specific PCR Assays for *Salmonella enterica* Serotypes Typhi and Paratyphi A", vol. 8, Issue 1, 11 pages, Jan. 2014.
Santos et al., "Magnetic ionic liquids: synthesis, properties and applications", RSC Advances, vol. 4, pp. 40008-40018, Aug. 5, 2014.
Siragusa, Gregory R., "Statistical Validation of the Track-Dilution Plating Method from Ground Beef and Carcass Surface Samples", Journal of Rapid Methods and Automation in Microbiology, vol. 7, pp. 155-161, May 3, 1999.
Suo et al., "Evaluation of a multiplex selective enrichment broth SEL for simultaneous detection of injured *Salmonella, Escherichia coli* O157:H7 and Listeria monocytogenes", Brazilian Journal of Microbiology, vol. 44:3, pp. 737-742, 2013.
Trujillo-Rodriguez et al., "Magnetic ionic liquids as non-conventional extraction solvents for the determination of polycyclic aromatic hydrocarbons", Analytica Chimica Acta, vol. 934, pp. 106-113, Jun. 8, 2016.
Vibbert et al., "Accelerating Sample Preparation Through Enzyme-Assisted Microfiltration of *Salmonella* in Chicken Extract", Biotechnol. Prog., vol. 31, No. 6, pp. 1551-1562, 2015.
Wang et al., "Enzymatic Digestion for Improved Bacteria Separation from Leafy Green Vegetables", Journal of Food Protection, vol. 79, No. 8, pp. 1378-1386, Mar. 17, 2016.
Wolffs et al., "Direct Quantitation and Detection of *Salmonellae* in Biological Samples without Enrichment, Using Two-Step Filtration and Real-Time PCR", Applied and Environmental Microbiology, vol. 72, No. 6, pp. 3896-3900, Jun. 2006.
Wu, V.C.H., "A review of microbial injury and recovery methods in food", Food Microbiology, vol. 25, pp. 735-744, Apr. 25, 2008.
Yan et al., "Isothermal amplified detection of DNA and RNA", Molecular BioSystems, vol. 10, pp. 970-1003, Feb. 18, 2014.
Chapman et al., "Comparison of culture, PCR and immunoassays for detecting *Escherichia coli* O157 following enrichment culture and immunomagnetic separation performed on naturally contaminated raw meat products", International Journal of Food Microbiology, vol. 68, pp. 11-20, Jan. 6, 2001.
Clark et al., "Magnetic ionic liquids as PCR-compatible solvents for DNA extraction from biological samples", Chem. Commun., vol. 51, pp. 16771-16773, Sep. 27, 2015.
Heininger et al., "PCR and Blood Culture for Detection of *Escherichia coli* Bacteremia in Rats", Journal of Clinical Microbiology, vol. 37, No. 8, pp. 2479-2482. Aug. 1999.
Mehdi et al., "Hydrophobic ionic liquids with strongly coordinating anions", The Royal Society of Chemistry, vol. 46, pp. 234-236, Nov. 21, 2009.
Nacham et al., "Synthesis and Characterization of the Physicochemical and Magnetic Properties for Perfluoroalkyl Ester and Fe(III) Carboxylate-based Hydrophobic Magnetic Ionic Liquids", The Royal Society of Chemistry, vol. 5, pp. 11109-11117, Jan. 13, 2016.
Nacham et al., "Synthetic Strategies for Tailoring the Physicochemical and Magnetic Properties of Hydrophobic Magnetic Ionic Liquids", Chemistry of Materials, vol. 27, pp. 923-931, Jan. 5, 2015.
Pérez et al., "Immunomagnetic Separation with Mediated Flow Injection Analysis Amperometric Detection of Viable *Escherichia coli* O157", Analytical Chemistry, vol. 70, No. 11, pp. 2380-2386, Jun. 1, 1998.
Rosatella et al., "New Low Viscous Cholinium-based Magnetic Ionic Liquids", New J. Chem., vol. 40, pp. 3124-3129, Jan. 19, 2016.
Sheridan et al., "Detection of mRNA by Reverse Transcription-PCR as an Indicator of Viability in *Escherichia coli* Cells", Applied and Environmental Microbiology, vol. 64, No. 4, pp. 1313-1318, Jan. 26, 1998.
Xie et al., "Thermomorphic Behavior of the Ionic Liquids [C4mim][FeCl4] and [C12mim][FeCl4]", Chem Phys Chem., vol. 12, pp. 364-368, 2011.
Yoshida et al., "Influence of Structural Variations in 1-alkyl-3-methylimidazolium Cation and Tetrahalogenoferrate(III) Anion on the Physical Properties of the Paramagnetic Ionic Liquids", J. Mater Chem., vol. 16, pp. 1254-1262, Jan. 9, 2006.
Zhang, Suojiang et al., "Ionic liquids with metal chelate anions", Chem. Comm., vol. 48, pp. 2334-2336, 2012.
Agrawal et al., "A high affinity phage-displayed peptide as a recognition probe for the detection of *Salmonella typhimurium*", Journal of Biotechnology, vol. 231, pp. 40-45, May 19, 2016.
Amagliani et al., "Development of a magnetic capture hybridization-PCR assay for Listeria monocytogenes direct detection in milk samples", Journal of Applied Microbiology, vol. 100, pp. 375-383, 2006.
Bhagwat, Arvind, "Simultaneous detection of *Escherichia coli* O157:H7, Listeria monocytogenes and *Salmonella* strains by real-time PCR", International Journal of Food Microbiology, vol. 84, pp. 217-224, 2003.
Braden, Christopher, "*Salmonella enterica* Serotype Enteritidis and Eggs: A National Epidemic in the United States", Food Safety, vol. 43, pp. 512-517, Aug. 15, 2006.
Centers for Disease Control, "National Enteric Disease Surveillance: *Salmonella* Annual Report, 2016", National Center for Emerging and Zoonotic Infectious Diseases, Division of Foodborne, Waterborne, and Environmental Diseases, 87 pages, Feb. 28, 2018.
Chatzimitakos et al., "Magnetic ionic liquid in stirring-assisted drop-breakup microextraction: Proof-of-concept extraction of phenolic endocrine disrupters and acidic pharmaceuticals", Analytica Chimica Acta, vol. 910, pp. 53-59, Jan. 8, 2016.
Cheung et al., "Application of BAX system, Tecra Unique(tm) *Salmonella* test, and a conventional culture method for the detection of *Salmonella* in ready-to-eat and raw foods", Journal of Applied Microbiology, vol. 103, pp. 219-227, 2007.
Clark et al., "Rapid preconcentration of viable bacteria using magnetic ionic liquids for PCR amplification and culture-based diagnostics", Anal. Bioanal. Chem., vol. 409, pp. 4983-4991, Jun. 20, 2017.
Clark et al., "Preservation of DNA in nuclease-rich samples using magnetic ionic liquids", The Royal Society of Chemistry, vol. 6, pp. 39846-39851, Apr. 11, 2016.
Clark et al., "Extraction of DNA by Magnetic Ionic Liquids: Tunable Solvents for Rapid and Selective DNA Analysis", Analytical Chemistry, vol. 87, pp. 1552-1559, Jan. 11, 2015.
Clark et al., "Magnetic ionic liquids in analytical chemistry: A review", Analytica Chimica Acta, vol. 934, pp. 9-21, Jun. 13, 2016.
Daher et al., "Recombinase Polymerase Amplification for Diagnostic Applications", Clinical Chemistry, vol. 62:7, pp. 947-658, 2016.
Davis et al., "Deterministic hydrodynamics: Taking blood apart", PNAS, vol. 103, No. 40, pp. 14779-14784, Oct. 3, 2006.
Domrose et al., "Efficient recombinant production of prodigiosin in Pseudomonas putida", Frontiers in Microbiology, vol. 6, Article 972, 10 pages, Sep. 2015.
Ducret et al., "Characterization and resuscitation of 'non-culturable' cells of Legionella pneumophila", BMC Microbiology, vol. 14:3, 10 pages, 2014.
Duncan et al., "A combined approach for the enhanced detection and isolation of *Bartonella* species in dog blood samples: Pre-enrichment liquid culture followed by PCR and subculture onto agar plates", Journal of Microbiological Methods, vol. 69, pp. 273-281, Jan. 24, 2007.

(56) References Cited

OTHER PUBLICATIONS

Emaus et al., "Preconcentration of DNA using magnetic ionic liquids that are compatible with real-time PCR for rapid nucleic acid quantification", Analytical and Bioanalytical Chemistry, vol. 410, pp. 4135-4144, Apr. 28, 2018.
Entis et al., "Rapid Methods for Detection, Identification, and Enumeration", Compendium of Methods for the Microbiological Examination of Foods, Chapter 10, pp. 89-126, 2015.
Fan et al., "Dynamic DNA Hybridization on a Chip Using Paramagnetic Beads", Anal. Chem., vol. 71, pp. 4851-4859, 1999.
Garrido et al., "A new multiplex real-time PCR developed method for *Salmonella* spp. and Listeria monocytogenes detection in food and environmental samples", Food Control, vol. 30, pp. 76-85, 2013.
Garrison et al., "Thermo-Mechanical and Antibacterial Properties of Soybean Oil-Based Cationic Polyurethane Coatings: Effects of Amine Ratio and Degree of Crosslinking", Macromolecular Materials and Engineering, vol. 299, pp. 1042-1051, 2014.
El-Gazzar et al., "*Salmonellae*, Salmonellosis, and Dairy Foods: A Review", Journal of Dairy Science, vol. 75, pp. 2327-2343, May 1, 1992.
Haddix et al., "Kinetic Analysis of Growth Rate, ATP, and Pigmentation Suggests an Energy-Spilling Function for the Pigment Prodigiosin of Serratia marcescens", Journal of Bacteriology, vol. 190, No. 22, pp. 7453-7463, Nov. 2008.
Hice et al., "Capture, Concentration, and Detection of *Salmonella* in Foods Using Magnetic Ionic Liquids and Recombinase Polymerase Amplification", Analytical Chemistry, vol. 91, pp. 1113-1120, 2019.
Hoffmann et al., "Economic Burden of Major Foodborne Illnesses Acquired in the United States", United States Department of Agriculture, Economic Information Bulletin No. 140, 59 pages, May 2015.
Jacobsen et al., "Quantification of mRNA in *Salmonella* sp. seeded soil and chicken manure using magnetic capture hybridization RT-PCR", Journal of Microbiological Methods, vol. 69, pp. 315-321, Feb. 2007.
Jokerst et al., "Development of a Paper-Based Analytical Device for Colorimetric Detection of Select Foodborne Pathogens", Analytical Chemistry, vol. 84, pp. 2900-2907, Feb. 7, 2012.
Kersting et al., "Multiplex isothermal solid-phase recombinase polymerase amplification for the specific and fast DNA-based detection of three bacterial pathogens", Microchim Acta, vol. 181, pp. 1715-1723, Feb. 18, 2014.
Kersting et al., "Rapid detection of Plasmodium falciparum with isothermal recombinase polymerase amplification and lateral flow analysis", Malaria Journal, vol. 13:99, 9 pages, 2014.
Kim et al., "SEL, a Selective Enrichment Broth for Simultaneous Growth of *Salmonella enterica, Escherichia coli* O157: H7, and Listeria monocytogenes", Applied and Environmental Microbiology, vol. 74, No. 15, pp. 4853-4866, Aug. 2008.
Kim et al., "Rapid Detection of *Salmonella enterica* Serovar Enteritidis from Eggs and Chicken Meat by Real-Time Recombinase Polymerase Amplification in Comparison with the Two-Step Real-Time PCR", Journal of Food Safety, vol. 36, pp. 402-411, 2016.
Lavu et al., "Selection and Characterization of Aptamers Using a Modified Whole Cell Bacterium SELEX for the Detection of *Salmonella enterica* Serovar Typhimurium", ACS Combinatorial Science, vol. 18, pp. 292-301, Apr. 12, 2016.
Lazcka et al., "Pathogen detection: A perspective of traditional methods and biosensors", Biosensors and Bioelectronics, vol. 22, pp. 1205-1217, 2007.
Li et al., "Advances in isothermal amplification: novel strategies inspired by biological processes", Biosensors and Bioelectronics, vol. 64, pp. 196-211, 2015.
Lillis et al., "Non-Instrumented Incubation of a Recombinase Polymerase Amplification Assay for the Rapid and Sensitive Detection of Proviral HIV-1 DNA", PLOS One, vol. 9, Issue 9, 9 pages, Sep. 2014.
Liu et al., "Development of an isothermal amplification-based assay for the rapid visual detection of *Salmonella* bacteria", J. Dairy Sci., vol. 100, pp. 7016-7025, May 24, 2017.
Lund-Olesen et al., "Capture of DNA in microfluidic channel using magnetic beads: Increasing capture efficiency with integrated microfluidic mixer", Journal of Magnetism and Magnetic Materials, vol. 311, pp. 396-400, 2007.
Mannoor et al., "Electrical detection of pathogenic bacteria via immobilized antimicrobial peptides", PNAS, vol. 107, No. 45, pp. 19207-19212, Nov. 9, 2010.

* cited by examiner

CAPTURING, CONCENTRATING, AND DETECTING MICROBES IN A SAMPLE USING MAGNETIC IONIC LIQUIDS AND RECOMBINASE POLYMERASE AMPLIFICATION

CROSS-REFERENCE TO RELATED APPLICATIONS

This application claims priority under 35 U.S.C. § 119 to Provisional application U.S. Ser. No. 62/834,169, filed on Apr. 15, 2019, which is herein incorporated by reference in its entirety including without limitation, the specification, claims, and abstract, as well as any figures, tables, or examples thereof.

GRANT REFERENCE

This invention was made with government support under Grant number CHE-1709372 awarded by the National Science Foundation. The government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 9, 2020, is named P12752US01_SEQ_LISTING_04-09-20_ST25 and is 1,239 bytes in size.

FIELD OF THE INVENTION

The present disclosure relates to a method and kit for capturing, concentrating, and detecting microbes in a sample using magnetic ionic liquids (MILs) and recombinase polymerase amplification (RPA). Specifically, a method combining magnetic ionic liquid (MIL)-based sample preparation and Recombinase Polymerase Amplification (RPA) for rapid detection of viable microbes in a sample is disclosed. The disclosed methods or kits provide a rapid and practical tool to detect any microbe or microbes on-site at levels as low as $10^3$ CFU/mL in a sample within about an hour.

BACKGROUND OF THE INVENTION

Microbes are everywhere. They can be in drinking water, beverage, river, lake, surface water, soil, air (as in aerosol), food, or food products. They can also be found in biologic fluids or solids from mammals or humans. Most of time, the existence or concentration of microbes does not need to be determined, at least in a short time frame. However, sometime, determination of particular microbes' existence and/or concentration is highly desirable, preferably as soon as possible, for diagnosis, safety, environmental monitoring, product quality control, or manufacturing purposes.

The family Enterobacteriaceae is a related grouping of gram-negative, facultatively anaerobic rod-shaped bacteria. The family contains several genera of importance to agriculture, food safety and human health, including *Cronobacter, Enterobacter, Envinia, Escherichia, Klebsiella, Pantoea, Pectobacterium, Salmonella, Serratia, Shigella* and *Yersinia*.

*Salmonella* is a good example. *Salmonella* is a ubiquitous, gram-negative genus of bacteria that is widespread in the environment or intestinal tracts of mammals and avian species and can be found as a contaminant in various foods, food ingredients, and in industrial food processing environments. Harmful *Salmonella* infection typically results from ingestion of tainted food products, including consumption of contaminated poultry, eggs, and dairy products. The Centers for Disease Control and Prevention (CDC) estimates that nontyphoidal *Salmonella* spp. are responsible for 1.2 million cases of illness, 19,000 hospitalizations, and nearly 380 deaths in the United States annually. The economic burden of *Salmonella* spp., determined by the number of illnesses and their severity, is greater than 3.4 billion USD annually, making it one of the five most costly foodborne pathogens.

Therefore, rapid, streamlined, and field-deployable methods for detection of some microbes, especially some like *Salmonella* spp. and other foodborne pathogens are crucial for maintaining public health, identifying pathogens capable of causing illness, ensuring the safety and quality of the food stream, and reducing costs and burdens resulted from pathogen contamination and remedies thereof. Even in some other situations where microbes are not harmful to human, it is still desirable to determine their existence and concentrations for other useful purposes.

Current detection techniques for microbe detection used by any industry include standard culture methods and polymerase chain reaction (PCR), due to the selectivity, reliability, and regulatory acceptance of these techniques. Although culture-based methods are still considered the "gold standard" for detection and enumeration of microbes, they are expensive, energy and waste-intensive, and time consuming due to their reliance on cell growth and the need for multiple steps to achieve the detection in a laboratory, which is usually not close to the site where detection is required.

A typical culture process for detection of microbes, such as *Salmonella*, may include a non-selective pre-enrichment, selective enrichment, and selective plating steps, as well as additional downstream confirmation steps, such as the use of diagnostic agar slants, biochemical testing, and/or serotyping. Some samples may also require delayed secondary enrichment, which involves re-incubation of *Salmonella*-negative samples and non-selective pre-enrichments for up to an additional week, followed by a repeat of selective enrichment-to-confirmation steps. As a result, cultural detection of microbes or *Salmonella* may require between several days to more than a week, depending on the sources needed to be sampled.

As an example, any delays in detection of *Salmonella*, if present, can lead to shipping, sale, and consumption of contaminated foods, thereby endangering public health. To reduce detection time, the food industry uses PCR, often as a means for rapid screening of food samples for contamination.

PCR couples a thermostable DNA polymerase and temperature cycling regime for in vitro amplification of target DNA sequences to levels detectable by gel electrophoresis or real-time fluorescence. Although PCR has gained wide acceptance in the food industry over past 20 years, the thermal cyclers needed for PCR are still expensive and complicated. As a result, most systems including PCR remain bench-bound or have limited portability for field use or on-site application.

Recently, recombinase polymerase amplification (RPA) has demonstrated its potential as an alternative means for the rapid detection of microbial pathogens and viruses. Unlike PCR, which relies on high heat to denature and separate duplex DNA (dsDNA), RPA accomplishes this at lower temperatures using an enzyme, recombinase.

In RPA, a recombinase/oligonucleotide primer complex initiates amplification following the identification of homologous target sequences within a dsDNA template. The recombinase/primer complex catalyzes the separation of the dsDNA, enabling the primer to hybridize to its target. Single-stranded DNA-binding proteins (SSB) aid in the hybridization process by preventing separation of the primer-sequence hybrid, followed by elongation. As with PCR, a DNA polymerase (Bacillus subtilis Pol I, Bsu) catalyzes product formation using the single-stranded DNA as a template. Exponential amplification is achieved as newly-synthesized copies of dsDNA act as templates for subsequent amplification cycles.

A major difference between PCR and RPA is their respective temperature profile used for amplification. RPA is an isothermal process—meaning "occurring under conditions of constant temperature". The isothermal nature of RPA obviates the need for a thermal cycler, allowing use of simple, small, and inexpensive heating devices. The optimal temperature of RPA has been reported to be from 37° C. to 42° C., but amplification of some specific products has been demonstrated at temperatures ranging from 25° C. to 45° C. Suitable product amplification can be achieved in less than 20 min with RPA, as time-consuming ramping between separate denaturation, annealing and extension temperatures is not required. Together, these attributes make RPA advantageous for use in resource-poor environments, such as in-field or on-site applications.

Although RPA products can be visualized using gel electrophoresis, gels electrophoresis also require specialized equipment and are time-consuming, taking upwards of 35 min to get results. As an alternative, disposable, colorimetric lateral flow devices can be used for rapid (<10 min) amplicon detection. These paper- or nitrocellulose-based devices rely on capillary action and therefore have no requirement for power.

Nucleic acid lateral flow immunoassays (NALFIA), used together with RPA, are typically based on a sandwich-type assay. Like RPA itself, these NALFIA devices are portable, economical and, simple to use outside of laboratory settings—characteristics that make them ideal for use in the field.

Although nucleic acid amplification techniques are highly specific, their successful applications for early microbes or pathogen detection in any sample may be limited by inherently low pathogen levels. Without a suitable means for capturing, concentrating, and purifying microbes prior to downstream analysis ("extraction" in purely chemical terms), the detection of pathogens in a sample may suffer from lack of reproducibility or from poor sensitivity due to inhibitory substances carried over from the sample matrix. Therefore, effective pathogen extraction from a real sample is still a critical starting step.

Cultural enrichment is commonly used prior to detection, allowing dilution of matrix-associated assay inhibitors, recovery of stressed or injured cells, and generation of a detectable level of the cells. Cultural enrichment may also enable selective growth of the pathogens, if a pathogen-specific enrichment medium is used. However, key drawbacks for cultural enrichment remain to be their increased assay time, possible outgrowth of target organisms by competitive microflora, and loss of information on the initial pathogen load.

While filtration- and centrifugation-based sample preparation techniques can enable physical enrichment of cells, clogging of filters and co-isolation of particles or debris, which may interfere with assay performance, can be problematic.

Magnetic techniques can also be used for capturing, concentrating, and purifying of cells from complex matrices in a given sample. The most widely-used magnet-based approaches involve magnetic microbeads or nanoparticle substrates functionalized with pathogen-specific antibodies capable of binding to cell surface antigens. Other approaches for functionalizing substrates for cell capture include one that uses of cationic charge, which is non-selective, and those that depend on semi-selective cell-ligand interactions, such as lectins, antimicrobial peptides, or antibiotics. In these approaches, functionalized magnetic beads or nanoparticles are dispersed throughout a sample slurry where they encounter and bind to bacteria. A magnetic field is then applied for physical isolation of the cell-enriched sorbent.

Drawbacks to particulate magnetic sorbents such as microbeads may include aggregation, diffusion- or suspension-based limitations, or poor access to microscopic physical niches where bacteria may be present. These issues may result in lower extraction efficiencies and/or clogging of microfluidic systems. These problems may be addressed, but not completely avoided, through the use of functionalized nanoparticles.

However, regardless of whether microbeads or nanoparticles are used, the antibodies used in immunomagnetic approaches may be expensive, unstable under harsh sample conditions, or have limited shelf lives.

Magnetic ionic liquids (MILs) are paramagnetic molten salts comprised of organic/inorganic cations and anions that exhibit melting points at or below 100° C. Like conventional ionic liquids (ILs), MILs possess negligible vapor pressures at ambient temperatures and tunable physicochemical properties including viscosity, solvent miscibility, and solvation capabilities. Owing to their tunable chemical structures and susceptibility to magnetic fields, MILs have been applied for the analysis of hormones in biological fluids, acidic pharmaceuticals, and endocrine disrupters, as well as for the extraction and preservation of nucleic acids.

Very recently, MILs were also investigated as solvents for the preconcentration of viable bacteria for culture and PCR-based detection. By dispersing the hydrophobic MIL in an aqueous suspension of *Escherichia coli* K12, viable cells were rapidly extracted and concentrated for downstream analysis as described in U.S. patent application Ser. No. 15/950,916, filed on Apr. 18, 2018 and titled "RAPID PRECONCENTRATION OF VIABLE BACTERIA USING MAGNETIC IONIC LIQUID FOR PCR AMPLIFICATION AND CULTURE-BASED DIAGNOSTICS", which is incorporated herein by reference.

Despite successful implementation of the MIL-based preconcentration approach for detection of *E. coli* DNA by qPCR, the expensive thermal cycling equipment and optical unit required for detection represent significant limitations for on-site and field-testing applications. Additionally, the ability of MIL solvents to extract industry-relevant foodborne pathogens, such as *Salmonella* Typhimurium, in a complex and real sample, such as in a food sample, has not been explored. Thus, a method for capturing, concentrating, and detecting industry-relevant microbes or foodborne pathogen, on-site and in the field, from a real sample, is still needed.

Accordingly, it is an objective of the present disclosure to provide a method using a combination of magnetic ionic liquids (MILs) for the extraction and preconcentration of viable microbes or their diagnostically useful cellular components, including, but not limited to DNA, RNA, or other nucleic acids, from a sample, such as food samples, and Recombinase Polymerase Amplification (RPA) for rapid detection of the microbes, such as *Salmonella*.

It is also an objective of the present disclosure to provide a kit for utilizing the disclosed method for detecting microbes, such as *Salmonella* from a sample.

BRIEF SUMMARY OF THE INVENTION

In one aspect, disclosed herein is a method of extracting, concentrating, detecting viable microbes from a sample, the method comprises contacting a sample with a magnetic ionic liquid (MIL) for the period of a contacting time; extracting the microbes or their diagnostically useful cellular components, including, but not limited to DNA, RNA, other nucleic acids, proteins, enzymes, lipids or cell wall materials characteristic of the target organism, from the magnetic ionic liquid using an aqueous extracting medium to generate an extracted sample; and using a detection method to identify the microbes, wherein the sample comprises viable microbes. Preferably the detection method can be a non-amplification-based diagnostic method or an amplification-based diagnostic method.

In some embodiments, the magnetic ionic liquid extracts the viable microbes from the sample. In some other embodiments, the magnetic ionic liquid extracts microbes' diagnostically useful cellular components, including, but not limited to DNA, RNA, other nucleic acids, proteins, enzymes, lipids or cell wall materials characteristic of the target organism from the sample. In some other embodiments, wherein the aqueous extracting medium enhances the microbes' or their diagnostically useful cellular components, including, but not limited to DNA, RNA, other nucleic acids, proteins, enzymes, lipids or cell wall materials characteristic of the target organism, recovery, compared to using water.

In a preferred embodiment, a method of extracting, concentrating, and detecting microbes is disclosed; the method comprising contacting a sample with a magnetic ionic liquid (MIL) for the period of a contacting time; extracting the microbes or their diagnostically useful cellular components, including, but not limited to DNA, RNA, other nucleic acids, proteins, enzymes, lipids or cell wall materials characteristic of the target organism, from the magnetic ionic liquid using an aqueous extracting medium to generate an extracted microbe sample; detecting the microbes; wherein the detecting is performed by an amplification-based detection method, a non-amplification-based detection method, or both; wherein the sample comprises viable microbes and wherein the viable microbes comprise gram-negative bacteria, gram-positive bacteria, or a mixture thereof.

In a preferred embodiment, the microbes are gram-negative bacteria selected from the group consisting of *Cronobacter sakazakii*, *E. coli*, *Klebsiella aerogenes*, *Pantoea eucalypti*, *Pantoea stewartii*, *Pectobacterium carotovorum*, *Salmonella bongori*, *Salmonella enterica*, *Serratia marcescens*, *Yersinia enterocolitica*, and mixtures thereof.

In a preferred embodiment, the sample is an aqueous solution derived from food, water, or aerosol as a result of dilution, extraction, soaking, rinsing, washing, collecting, concentrating, or combination thereof; and wherein the magnetic ionic liquid extracts the viable microbes from the sample. In a preferred embodiment, the extracting medium is a Luria-Bertani-derived nutrient broth comprising more than 10 g/L of tryptone, more than 5 g/L of yeast extract, more than 10 g/L of NaCl, or combination thereof. Preferably, there is a volume ratio between the magnetic ionic liquid and the extracting medium is from about 1:5 to 1:15.

A preferred embodiment is a kit for extracting, concentrating, detecting viable microbes in a sample, comprising a magnetic ionic liquid and an extracting medium, wherein the extracting medium is a Luria-Bertani-derived nutrient broth comprising more than 10 g/L of tryptone, 10 g/L of NaCl, 5 g/L of yeast extract, or combination thereof; wherein a volume ratio between the magnetic ionic liquid and the extracting medium is from about 1:5 to 1:15; and a power-free heat source, wherein the magnetic ionic liquid comprises a paramagnetic anionic component and a cationic component, or a paramagnetic cationic component and an anionic component.

In a preferred embodiment, the magnetic ionic liquid comprises a paramagnetic anionic component and a cationic component, wherein the cationic component has a general formula (I), (IV), or (V)

$$[(PR^1R^2R^3R^4)^+] \quad (I)$$

wherein each of the $R^1$, $R^2$, $R^3$, and $R^4$ is independently an unsubstituted or substituted alkyl;
wherein the paramagnetic anionic component has the following general formula (II), $$[M(Y)_x^-] \quad (II)$$

wherein M is transition metal or rare earth metal ion; and Y is a chelating agent having the general formula (III),

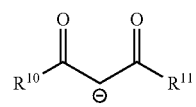

(III)

each of the $R^{10}$ and $R^{11}$ are independently a substituted or unsubstituted methyl, phenyl, thiophenyl, napthyl, alkyl, or aryl group; and x is 3 or 4

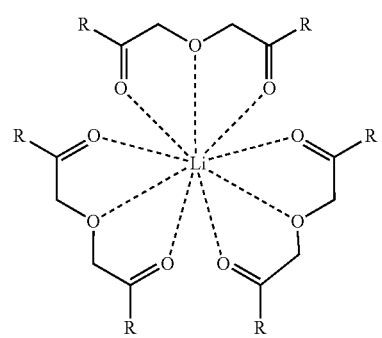

(IV)

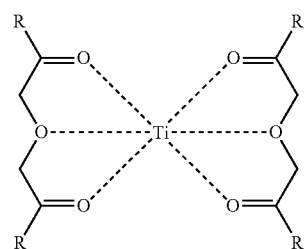

(V)

wherein R is one or more of the following:

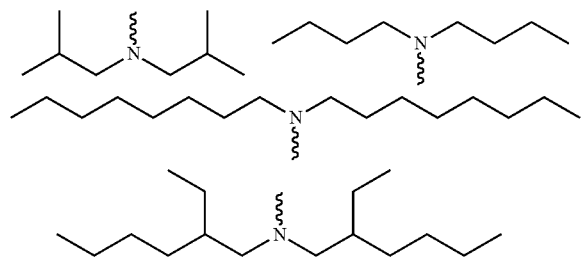

and wherein Ti comprises Co, Ni, Mn or a combination thereof and Ln comprises Dy, Gd, Ho, or a combination thereof.

In a preferred embodiment, the magnetic ionic liquid comprises a paramagnetic cationic component and an anionic component, wherein the anionic component has a general formula (VI) or (VII)

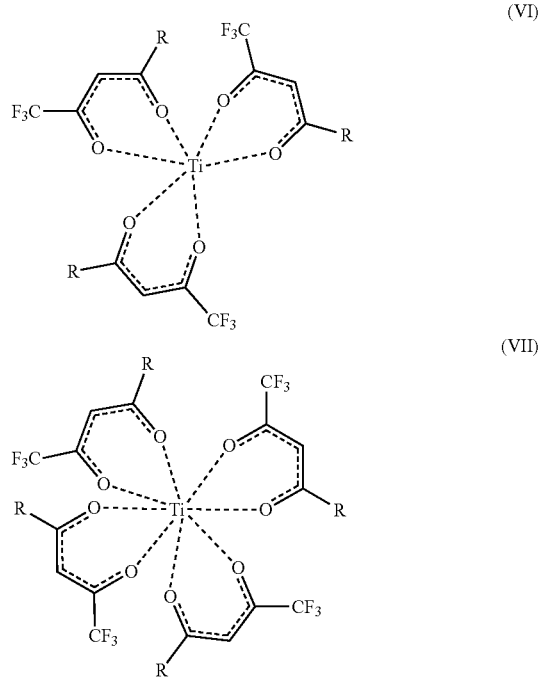

wherein R is one or more of the following:

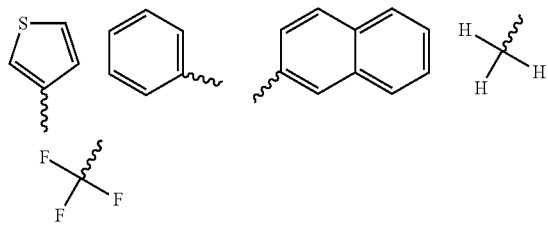

and wherein Ti comprises Co, Ni, Mn or a combination thereof and Ln comprises Dy, Gd, Ho, or a combination thereof.

In yet another aspect, disclosed herein is a kit for extracting, concentrating, detecting viable microbes from a sample, the kit comprises a magnetic ionic liquid as disclosed herein; an enzyme for Recombinase Polymerase Amplification (RPA); and a primer for RPA, wherein the primer is one for Salmonella-specific DLH gene.

The methods disclosed herein represent the first use of a magnetic ionic liquid for capturing and concentrating viable microbes from a real sample, including at-risk foods and of RPA for amplification of microbial DNA or RNA, using a chemically powered heat source. Thereafter, microbial RPA amplicons could be detected in less than 10 minutes using a simple chromatographic readout.

The disclosed method is simple, streamlined, and amenable to analyses in the field or in other resource-limited places.

Apart from their magnetic properties, the MILs used here have other advantageous characteristics useful for the analysis of aqueous, liquid, solid, or air samples, such as foods or food suspensions, where microbes may exist or multiply. Unlike other recently reported MILs, which have reported room temperature densities that are on par with that of water, some exemplary Ni(II) and Co(II) MILs disclosed herein have densities of ~1.3 g/mL, which lie between the densities of glycerol (1.26 g/mL) and corn syrup (~1.4 g/mL). Because some exemplary MILs used the method disclosed herein are both hydrophobic and denser than water and can be collected through either simple density-based sedimentation or with application of an external magnet, they are well-suited for analysis of aqueous solutions such as liquid foods or food suspensions.

For automated and high-throughput applications in any industry, it is possible to use a strong electromagnet for fast and uniform capture of cell-enriched MILs. It is also possible to minimize the costs and environmental impacts of high-throughput use of MILs in food testing by developing methods capable of recycling MILs for multiple rounds of cell capture.

The methods and kits disclosed herein provide new tools for rapid and efficient extraction and detection of viable microbes in samples, specifically viable Salmonella bacteria in food samples.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The patent or application file contains at least one drawing or photograph executed in color. Copies of this patent or patent application publication with color drawing(s) will be provided by the Office upon request and payment of the necessary fee.

FIG. 12A shows 1× peptone water (PW); FIG. 12B shows 5× PW; FIG. 12C shows 10× PW. Apart from the size distribution data noted for each medium, these suspensions consisted generally of well-separated droplets having minimal interactions.

DETAILED DESCRIPTION OF THE PREFERRED EMBODIMENT

Figure 1A:
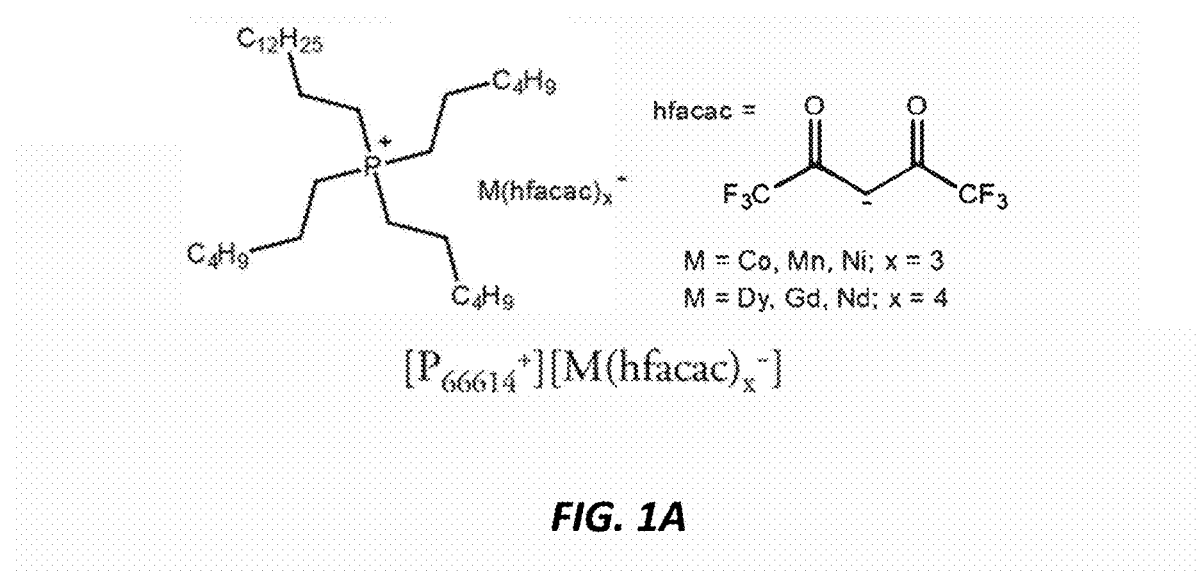
FIG. 1A shows the general structures of some exemplary MILs, including those used in Example 1.

The present disclosure relates to a method for extracting, concentrating, detecting viable microbes from a sample. The embodiments of the methods and kits are not limited to any particular metal ion, chelating species, microbe, extracting medium, RPA method, or detection methods for amplicons which can vary and are understood by skilled artisans based on the present disclosure.

It is further to be understood that all terminology used herein is for describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of the disclosed MILs, synthesis thereof, and methods are presented in a range format. The description in range format is merely for convenience and brevity and should not be construed as an inflexible limitation on the scope of the disclosed MILs and methods. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present disclosure may be more readily understood, certain terms are first defined. Unless defined otherwise, all technical and scientific terms used herein have the same meaning as commonly understood by one of ordinary skill in the art to which embodiments of the disclosed MILs and methods pertain. Many methods and materials similar, modified, or equivalent to those described herein can be used in the practice of the embodiments of the disclosed MILs and methods without undue experimentation. The preferred materials and methods are described herein. In describing and claiming the embodiments of the disclosed MILs and methods, the following terminology will be used in accordance with the definitions set out below.

The term "about," as used herein, refers to variations in size, distance or any other types of measurements that can be resulted from the inherent heterogeneous nature of the measured objects and imprecise nature of the measurements themselves. The term "about" also encompasses variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods, and the like. The term "about" also encompasses amounts that differ due to different equilibrium conditions for a composition resulting from a particular initial mixture. Whether or not modified by the term "about", the claims include equivalents to the quantities.

As used herein the term, "diagnostically useful cellular components" includes, but is not limited to, DNA, RNA, other nucleic acids, proteins, enzymes, lipids or cell wall materials characteristic of the target organism.

The term "independently" means that where more than one substituent is selected from a number of possible substituents, those substituents may be the same or different.

As used herein, "substituted" refers to an organic group as defined below (i.e., an alkyl group) in which one or more bonds to a hydrogen atom contained therein are replaced by a bond to non-hydrogen or non-carbon atoms. Substituted groups also include groups in which one or more bonds to carbon(s) or hydrogen(s) atom replaced by one or more bonds, including double or triple bonds, to a heteroatom. Thus, a substituted group is substituted with one or more substituents, unless otherwise specified. A substituted group can be substituted with 1, 2, 3, 4, 5, or 6 substituents.

Substituted ring groups include rings and ring systems in which a bond to a hydrogen atom is replaced with a bond to a carbon atom. Therefore, substituted cycloalkyl, aryl, heterocyclyl, and heteroaryl groups may also be substituted with substituted or unsubstituted alkyl, alkenyl, and alkynyl groups are as defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Alkenyl groups or alkenes are straight chain, branched, or cyclic alkyl groups having 2 to about 30 carbon atoms, and further including at least one double bond. In some embodiments, alkenyl groups have from 2 to about 20 carbon, or typically, from 2 to 10 carbon atoms. Alkenyl groups may be substituted or unsubstituted. Alkenyl groups may be substituted similarly to alkyl groups.

As used herein, the terms "alkylene", cycloalkylene", alkynylene, and alkenylene", alone or as part of another substituent, refer to a divalent radical derived from an alkyl, cycloalkyl, or alkenyl group, respectively, as exemplified by —$CH_2CH_2CH_2$—. For alkylene, cycloalkylene, alkynylene, and alkenylene groups, no orientation of the linking group is implied.

As used herein, "aryl" or "aromatic" groups are cyclic aromatic hydrocarbons that do not contain heteroatoms. Aryl groups include monocyclic, bicyclic, and polycyclic ring systems. Thus, aryl groups include, but are not limited to, phenyl, azulenyl, heptalenyl, biphenylenyl, indacenyl, florenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, in others from 6 to 12 or 6-10 carbon atoms in the ring portions of the groups. The phrase "aryl groups" includes groups containing fused rings, such as fused aromatic-aliphatic ring systems. Aryl groups may be substituted or unsubstituted.

In one aspect, disclosed herein is a method of extracting, concentrating, detecting viable microbes from a sample, the method comprises contacting a sample with a magnetic ionic liquid (MIL) for the period of a contacting time; extracting the microbes or their diagnostically useful cellular components, including, but not limited to DNA, RNA, or other nucleic acids, from the magnetic ionic liquid using an aqueous extracting medium to generate an extracted sample; and using Recombinase Polymerase Amplification (RPA) on the extracted sample for amplifying DNA or RNA of the microbes, wherein the sample comprises viable microbes.

In another aspect, disclosed herein is a method of extracting, concentrating, detecting viable microbes from a sample, the method comprises contacting a sample with a magnetic ionic liquid (MIL) for the period of a contacting time; extracting the microbes or their diagnostically useful cellular components, including, but not limited to DNA, RNA, or other nucleic acids, from the magnetic ionic liquid using an aqueous extracting medium to generate an extracted sample; and using Recombinase Polymerase Amplification (RPA) on the extracted sample for amplifying DNA or RNA of the microbes; wherein the RPA is carried out with a power-free heat source, wherein the sample comprises viable microbes.

In yet another aspect, disclosed herein is a method of extracting, concentrating, detecting viable microbes from a sample, the method comprises contacting a sample with a magnetic ionic liquid (MIL) for the period of a contacting time; extracting the microbes or their diagnostically useful cellular components, including, but not limited to DNA, RNA, or other nucleic acids, from the magnetic ionic liquid using an aqueous extracting medium to generate an extracted sample; wherein the extracting medium is a Luria-Bertani-derived nutrient broth comprising more than 10 g/L of tryptone, 10 g/L of NaCl, 5 g/L of yeast extract, or combination thereof; and using Recombinase Polymerase Amplification (RPA) on the extracted sample for amplifying DNA or RNA of the microbes, wherein the sample comprises viable microbes.

In yet another aspect, disclosed herein is a method of extracting, concentrating, detecting viable microbes from a sample, the method comprises contacting a sample with a magnetic ionic liquid (MIL) for the period of a contacting time; extracting the microbes or their diagnostically useful cellular components, including, but not limited to DNA, RNA, or other nucleic acids, from the magnetic ionic liquid using an aqueous extracting medium to generate an extracted sample; and using Recombinase Polymerase Amplification (RPA) on the extracted sample for amplifying DNA or RNA of the microbes, wherein the sample comprises viable microbes; wherein the microbes are *Salmonella*, and wherein RPA is carried out with a primer for *Salmonella*-specific DLH gene.

In some embodiments, wherein the extracting medium is a Luria-Bertani-derived nutrient broth comprising more than 10 g/L of tryptone, more than 5 g/L of yeast extract, more than 10 g/L of NaCl, or combination thereof. In some other embodiments, the extracting medium is a Luria-Bertani-derived nutrient broth comprising from more than 10 g/L to about 20 g/L of NaCl, from more than 10 g/L to about 20 g/L of tryptone, from more than 5 g/L to about 20 g/L of yeast extract, or combination thereof.

In some embodiments, the power-free heat source is a chemical heat pack. A chemical heat pack is based on exothermic chemical reactions and may be regenerable. In some other embodiments, the power-free heat source is a portable heat source energized by a battery or solar energy or light. In some other embodiments, the power-free heat source is a USB-powered incubator or battery powered infrared lamp. In some other embodiments, the power-free heat source is body heat from a mammal or human.

During the contacting time, the microbes, their diagnostically useful cellular components, including, but not limited to DNA, RNA, other nucleic acids, proteins, enzymes, lipids or cell wall materials characteristic of the target organism, or both migrate from the sample to the MIL. In some embodiments, the magnetic ionic liquid extracts the viable or intact microbes from the sample during the contact time. In some other embodiments, the MIL extracts the microbes' diagnostically useful cellular components, including, but not limited to DNA, RNA, other nucleic acids, proteins, enzymes, lipids or cell wall materials characteristic of the target organism, from the sample during the contact time.

In some other embodiments, wherein the medium enhances the microbes' or their diagnostically useful cellular components', including, but not limited to DNA, RNA, other nucleic acids, proteins, enzymes, lipids or cell wall materials characteristic of the target organism, recovery, compared to using water.

As used herein, "extract" means that the microbes or their diagnostically useful cellular components, including, but not limited to DNA, RNA, other nucleic acids, proteins, enzymes, lipids or cell wall materials characteristic of the target organism, in the sample migrates onto or into the MIL during the contact time and then from the MIL to the extracting medium during the extracting step. After the "contacting" step and before the "extracting" step, the MIL can be mixed well with the sample, if the sample is liquid or contains liquid. In some situations, if the sample cannot mix with MIL liquid thoroughly, water or a solvent can be added to the sample or the mixture of the sample and MIL, so the added water and solvent can be the medium for the microbes to migrate from the sample to MIL.

As used herein, a "sample" can be a liquid or solid substance that contains the microbes to be extracted. In some other situation, a sample can one derived from a substance that contains the microbes to be detected through one or more routine water or solvent extraction methods known in the art. In some other situation, a sample can a liquid or solid material that have been used to accumulate microbes from other source. For example, a sample can be a liquid media or solid material that is used to collect aerosols that contain the microbes to be detected via cyclonic concentrator devices.

A sample can be a food sample that is originated directly from animals or plants, such as milk, juice, or derived from those originated from animals or plants, with or without any sample preparation or treatment procedure. A sample can also be a mixture of water or solvent and a specimen collected from any substance that can comprises the microbes to be detected. A sample can be a food sample that is from a food or food source that can comprise microbes.

A sample can a water sample collected from a river, lake, pond, tank, reservoir, surface water, or any other water source. A sample can also be a soil sample taken from any place.

A sample can also be a biological fluid or solid from a mammal or human, such as blood, plasma, urine, feces, or other body fluid or solid.

In some embodiments, the sample is food or a food product. In some other embodiments, the samples is milk, juice, or egg.

In some embodiments, the sample comprises the viable microbes. In some other embodiments, the sample comprises the viable microbes at a concentration of about $10^3$ CFU/ml or greater.

A sample can be a slurry or aqueous suspension made of a solid or dry food or other solid specimen by dilution and homogenization using water or a buffer system, a common procedure used as the first step in traditional microbiological analysis of solid or dry foods, a surface sample collected into an aqueous medium as a rinsate or from a sponge or swab, or an air sample collected into an aqueous medium via cyclonic concentration.

As used herein, microbes can be bacteria, archaea, fungi (yeasts, molds, etc.) protozoa, viruses, or mixtures thereof. Microbes of a specific type (genus, species, etc.) usually share some characteristic DNA or RNA among themselves and can be distinguished from another types of microbes because of their respective characteristic DNA or RNA sequences. In some embodiments, the microbes are *Cronobacter sakazakii, E. coli, Klebsiella aerogenes, Pantoea eucalypti, Pantoea stewartii, Pectobacterium carotovorum, Salmonella bongori, Salmonella enterica, Serratia marcescens*, and/or *Yersinia enterocolitica*. In some other embodiments, the microbes are yeast for beer production.

In some embodiments, the microbes can be gram-negative bacteria. Various gram-negative are described herein. In other embodiments, the microbes can be gram-positive bacteria.

In some other embodiments, the microbes can be non-pathogenic *Escherichia coli*, such as *E. coli* K12 or *E. coli* ATCC 25922 or related non-pathogenic bacteria such as *Serratia marcescens*. In yet some other embodiments, the microbes can pathogenic *Escherichia coli*, such as *Escherichia coli* O157:H7, an important foodborne pathogen considered as an adulterant if present in foods.

In some embodiments, the microbes can be *Salmonella enterica, Salmonella bongori*, or a combination of *Salmonella enterica* and *Salmonella bongori*. In some embodiments, the microbes are *Salmonella* having a truncated outer membrane. In some other embodiments, the microbes are *Salmonella Minnesota*.

Gram-negative bacteria, such as members of the Family Enterobacteriaceae, possess a protective outer barrier layer, called the outer membrane (OM). The OM serves to limit the passive diffusion of molecules, particularly hydrophobic molecules (such as certain classes of antibiotics) into the interior of the cell. Treatment or interaction with various chemicals may physically damage the OM and other cellular structures or components, causing what is broadly characterized as "cell injury".

Cell injury can be detected by plating chemically-treated cells in parallel on both non-selective and selective agars and evaluating growth under each condition. Physiologically healthy (non-injured) gram-negative cells can tolerate exposure to selective agents—compounds such as the dye crystal violet or sodium desoxycholate, which are inherently toxic to gram-positive cells, which do not possess an OM structure. Injury to gram-negative cells caused by exposure to deleterious chemicals (or other "insults" such as heat) is typically characterized by damage to the OM, causing the cell to become "leaky", allowing ingress of these selective/toxic compounds, resulting in reduced growth on selective agars. Injury can therefore be detected by plating treated cells in parallel on both non-selective and selective agars and comparing the results. For example, when we exposed suspensions of S. Typhimurium to the Ni(II) MIL for times ranging from 0 min (essentially our standard 30 s extraction protocol) to 15 min, the resulting average CFU counts on TSA and BSA appeared similar, regardless of exposure time. We explored these data further using the statistical analyses reported in the Electronic Supplementary Material. For TSA, no statistically significant differences were shown in the CFU counts over time. For cases that were plated to BSA, we did find significant evidence that the CFU counts at time 5 min, 10 min, and 15 min are statistically greater compared to time 0 counts. While not wishing to be bound by the theory, we hypothesize that if the Ni(II) MIL was chemically injurious to S. Typhimurium, counts on BSA would be lower than those observed on TSA, and further, that BSA counts would continue to fall as a function of exposure time. Although we found that CFU counts on BSA were statistically different from counts at time zero, the observation that counts at 5, 10 and 15 min were greater than those at time zero support our conclusion that the Ni(II) MIL did not cause detectable injury to S. Typhimurium with this media pairing, even after exposure periods thirty times longer than our standard 30 s extraction time.

If chemically-treated cells grow to the same or similar degree on non-selective and selective agars, this indicates that the chemical treatment did not cause cellular injury and the chemical is not inherently toxic to the cells. Alternatively, if chemically-treated cells show a differential between growth on non-selective and selective agars, with lower growth on the selective agar, the chemical treatment did cause cellular injury and was toxic to the cells. In our toxicity testing, the "chemical" used to treat bacteria was the Ni(II) MIL.

Multiple strains of Salmonella and E. coli O157:H7 were tested for injury after exposed to the exemplary MIL disclosed herein for periods corresponding to the contact time experienced during our normal MIL capture and concentration protocol (as well as for longer periods of time), then plated in parallel on both non-selective and selective agars. The results showed that the exemplary MILs did not show toxicity towards wildtype Salmonella and E. coli O157:H7 strains.

It was surprising or unexpected to find out that the disclosed method was able to capture a "deep rough" mutant of Salmonella enterica serovar Minnesota, which has a defect in its OM and a severely truncated lipopolysaccharide (LPS) layer. Cells with truncated out LPS/OM are often dramatically more susceptible to chemically harsh environments or antimicrobial agents than are cells with intact LPS/OM, as they no longer possess this important barrier structure.

The claimed method's ability to capture this "deep rough" strain demonstrates two important advantages of the claimed method: 1) The capacity of the MILs to effectively bind to (capture) and concentrate these important gram-negative variants that display a very different surface to the external environment and 2) The post-capture growth behavior of this physiologically sensitive strain indicates that the claimed method is not physically harsh or deleterious to the microbes. The lack of toxic impact of the claimed method on the "deep rough" S. Minnesota strain could result from a lack of inherent chemical toxicity of the MIL, from the minimal diffusivity of the hydrophobic MIL in liquid media (which would be expected to prevent MIL molecules from entering the cell), or a combination of both of these possibilities.

In some other embodiments, the microbes can be other pathogenic bacteria. In some other embodiments, the microbes are Cronobacter, problematic bacteria in dried milk foods, including infant formula. In other embodiments, the microbes are Erwinia, an economically important plant pathogen causing vegetable soft rot. In yet some other embodiments, the microbes are Klebsiella, clinically important antibiotic-resistant strains. In some other embodiments, the microbes are Shigella or Yersinia, genera that contain important food pathogens. In some other embodiments, the microbes are Y. pestis, a causative agent of bubonic plague.

In some embodiments, during or after the contacting step, any manual or mechanical method can be used during the contact time to maximize the mixing of the MIL and the sample. In some embodiments, vortexing is used. In some embodiments, mechanical stirring is used.

In some embodiments, during or after the contacting step or during the extracting step, the sample or the mixture of the sample and MIL may subject to heat, ultrasound, pressure, water, solvent, or chemical treatment, or a combination thereof, in order to increase the extraction of the microbes and/or their diagnostically useful cellular components, including, but not limited to DNA, RNA, other nucleic acids, proteins, enzymes, lipids or cell wall materials characteristic of the target organism.

In some embodiments, during or after the contacting step, the microbes from the sample stay intact or remain viable in the MIL. In some embodiments, during or after contacting step, the microbes in MIL become disintegrated or lysed to generate their diagnostically useful cellular components, including, but not limited to DNA, RNA, other nucleic acids, proteins, enzymes, lipids or cell wall materials characteristic of the target organism. In some embodiments, the MIL or the claimed method does not cause injury to cells of the microbes.

In some embodiments, after the "contacting" step and before the "extracting" step, the MIL comprises the viable microbes, diagnostically useful cellular components, including, but not limited to DNA, RNA, other nucleic acids, proteins, enzymes, lipids or cell wall materials characteristic of the target organism, or a combination thereof. In some embodiments, the MIL comprises viable microbes. In some other embodiments, the MIL comprises lysed cells of the microbes. In yet some other embodiments, the MIL comprises the characteristic or unique DNA or RNA of the microbes.

As used herein, "using Recombinase Polymerase Amplification (RPA) on the extracted sample for amplifying DNA or RNA of the microbes" refers to contact an enzyme for Recombinase Polymerase Amplification (RPA) and a primer or primer set with the extracted sample for the purpose of amplifying the characteristic DNA or RNA of the microbes. In some embodiments, an additional reverse transcriptase (RT) enzyme is used to contact the extracted sample if the characteristic RNA sequence is targeted for amplification. In some embodiments, the primer or primer set is for the dienelactone hydrolase or "DLH" enzyme of *Salmonella*. In some other embodiments, the primer or primer set for genes related to innate bacterial immunity mechanisms (CRISPR sequences) unique to the microbes.

The microbes' characteristic DNA or RNA, which is amplified in the subsequent Recombinase Polymerase Amplification (RPA), includes virulence factors or other DNA or RNA sequences not involved in virulence but otherwise unique to the target microbes. Many of these characteristic or unique DNA or RNA sequences are known for specific target organisms. Others can be discovered via methods such as comparative genomics, or analysis of CRISPR sequences.

To achieve specific detection of an organism, we can target its DNA or RNA, as long as the sequence is unique to a specific microbe. In some embodiments, the characteristic RNA sequence of the microbes is amplified using reverse transcription RPA, an RPA reaction to which the enzyme reverse transcriptase is added in order to create amplifiable DNA from RNA, as described below. The advantage of utilizing the characteristic RNA, such as ribosomal RNA, is that such RNA sequence exists in multicopy.

In some embodiments, the characteristic DNA or RNA sequence is a gene or sequence associated with a virulence factor for a pathogen. One such exemplary gene is the invasion protein gene invA that can used for NALFIA-based detection of *Salmonella*. The other genes for virulence factors can include those for bacterial flagella involved in initial attachment of bacteria to host cells or for additional proteins involved in bacterial virulence, such as the outer membrane protein OmpA found in various gram-negative bacilli.

In other cases, the characteristic DNA or RNA sequences are genes or sequences that are not associated with virulence, but are present only in the microbe being tested for. Examples of these genes include the putative dienelactone hydrolase gene that was determined to be restricted to *Salmonella* through comparison of the *Salmonella* genome against the genomes of several closely-related bacteria, or other genetic elements, such as Clustered Regularly Interspaced Short Palendromic Repeats (CRISPR) sequences. In these cases, the ultimate function of the gene or sequence is not important, as long as it is unique to the microbe that is tested for. In some embodiments, the characteristic DNA or RNA sequences are genes or parts of genes involved in bacterial metabolism (enzymes, such as the dienelactone hydrolase or "DLH" enzyme) or genes related to innate bacterial immunity mechanisms (CRISPR sequences).

A characteristic or unique DNA or RNA sequences for a microbe can be determined or verified experimentally using assays with target and non-target strains. Alternatively, a characteristic or unique DNA or RNA sequences for a microbe can be determined in silico (computer-based) screening of data, using the PrimerBlast tool from the National Center for Biotechnology Information (NCBI). This tool allows one to screen large DNA databases to check the exclusivity (does it only detect the pathogen you're looking for?) and inclusivity (how many strains or species of this pathogen does it detect?) of the sequence targeted by the assay.

In some embodiments, using a characteristic RNA for RPA is preferred, especially ribosomal RNA (rRNA). rRNA contains variable regions that contain pathogen-specific sequences. Additionally, rRNA is present in cells at high copy numbers—up to 100,000 copies, instead of a single copy as is the case with some genomic targets. High target copy numbers can significantly enhance the sensitivity of an amplification assay such as RPA.

However, because RPA is a method for DNA amplification, RPA assays must be modified to allow detection of RNA. Specifically, a reverse transcriptase (RT) enzyme must be included for characteristic RNA detection. The RT enzyme will generate complementary DNA (cDNA) from the single-stranded rRNA template and the RPA enzyme system can use this cDNA as a substrate for DNA amplification.

Various virulence genes and virulence-enhancing genes and their corresponding primer sets have been investigated and described for the polymerase chain reaction (PCR) to detect and characterize *Salmonella*, as in Chapter 4, The Use of Molecular Methods for Detecting and Discriminating Food Borne Infectious Bacteria, Levin, R. E., CRC, 2010, CRC Press which is hereby incorporated by reference. There are presently over 30 *Salmonella*-specific genes that have been used for *Salmonella*. These include invA gene sequences that are highly conserved among all *Salmonella* serotypes.

A general principle, procedure, and optimization for DNA/RNA amplification using recombinase polymerase amplification (RPA) has been described, as in TwistAmp® DNA Amplification Kits, Assay Design Manual (https://www.twistdx.co.uk/docs/default-source/RPA-assay-design/twistamp-assay-design-manual-v2-5.pdf), which is hereby incorporated by references.

According to the TwistAmp® manual, "Primers designed for a given PCR assay may often work in RPA but may not be optimal for TwistAmp® reactions. For assays requiring less stringent detection (greater than 1,000 copies per sample tested) only a small number of primers need be screened in most cases and use of PCR primers may be sufficient." In other words, DNA/RNA sequences and their corresponding primer sets reported in the literature for PCR-based detection of *Salmonella* are helpful as a starting point for detection of *Salmonella* using RPA, but success of using the same in RPA is not predicable, considering the interference from different samples and their matrixes can be different for PCR and RPA, let alone in the claimed methods using both MIL and RPA.

Indeed, as indicated in this disclosure, targeting genes or DNA/RNA sequences with the corresponding primer sets recommended for PCR may not generate the optimal results for the disclosed methods that use RPA and/or MIL. For examples, the DLH primer set, despite its apparent divergence from existing RPA primer design considerations, was found to be surprisingly more useful for RPA and the claimed methods, compared to the InvA gene and its corresponding primer sets preferred for PCR.

In some embodiments, during the extracting step, the microbes in the MIL and/or the extracting medium stay intact or remain viable. In some embodiments, during the extracting step, the microbes become disintegrated or lysed to generate their diagnostically useful cellular components, including, but not limited to DNA, RNA, other nucleic acids, proteins, enzymes, lipids or cell wall materials characteristic of the target organism.

As used herein, an extracting medium refers to an aqueous medium or solution whose ionic strength is adjusted through the addition of various ionic species. In some embodiments, the aqueous medium promotes the release of the captured cells (microbes or diagnostically useful cellular components, including, but not limited to DNA, RNA, other nucleic acids, proteins, enzymes, lipids or cell wall materials characteristic of the target organism) from the MIL. In some embodiments, the extracting medium comprises tryptone, yeast extract, sodium chloride or a combination thereof as the ionic species used to adjust the ionic strength.

In some embodiments, the extracting medium does not affect cell viability. In some other embodiments, the extracting medium promotes cell release, cell lysis, microbes' release of their characteristic DNA/RNA for analysis, or a combination thereof, compared to using water alone. In some embodiments, the aqueous extracting medium enhances the microbes' or their diagnostically useful cellular components', including, but not limited to DNA, RNA, other nucleic acids, proteins, enzymes, lipids or cell wall materials characteristic of the target organism, recovery, compared to using water.

In some embodiments, the extracting medium is a Luria-Bertani-derived nutrient broth. In some other embodiments, the extracting medium is an aqueous solution comprising yeast extract for microbiology. In some other embodiments, the extracting medium is a Luria-Bertani-derived nutrient broth comprising tryptone. In yet some other embodiments, the extracting medium is a Luria-Bertani-derived nutrient broth comprising yeast extract for microbiology. In some embodiments, the extracting medium is a Luria-Bertani-derived nutrient broth comprising NaCl. In some other embodiments, the extracting medium is a Luria-Bertani-derived nutrient broth comprising one or more of tryptone, yeast extract, and NaCl.

In some embodiments, the extracting medium is a Luria-Bertani-derived nutrient broth or aqueous solution comprising from about 1 g/L to about 30 g/L, from about 1 g/L to about 25 g/L, from about 1 g/L to about 20 g/L, from about 1 g/L to about 15 g/L, from about 1 g/L to about 10 g/L, about 2, about 4, about 6, about 8, about 10, about 12, about 14, about 16, about 18, about 20, about 22, about 24, about 26, about 28, or any value there between of one or more tryptone, yeast extract, NaCl, or other salt(s) that are routinely used in microbiology for changing ionic strength of an aqueous solution.

In some embodiments, the extracting medium is a Luria-Bertani-derived nutrient broth or aqueous solution comprising from about 1 g/L to about 20 g/L, from about 1 g/L to about 15 g/L, from about 1 g/L to about 10 g/L of tryptone and from about 1 g/L to 10 g/L or from about 1 g/L to about 5 g/L of yeast extract.

In some other embodiments, the extracting medium is a Luria-Bertani-derived nutrient broth or aqueous solution comprising from about 1 g/L to about 20 g/L, from about 1 g/L to about 15 g/L, from about 1 g/L to about 10 g/L of tryptone and from about 1 g/L to 10 g/L or from about 1 g/L to about 5 g/L of NaCl.

In some embodiments, a volume ratio between the magnetic ionic liquid and the extracting medium is from about 1:5 to about 1:15, from about 5:1 to about 1:15, from about 2:1 to about 1:15, from about 1:1 to about 1:15, from about 1:3 to about 1:15, from about 1:5 to about 1:10, from about 1:5 to about 1:8, or any value there between.

In some embodiments, the extracted microbe sample comprises the viable microbes, diagnostically useful cellular components, including, but not limited to DNA, RNA, other nucleic acids, proteins, enzymes, lipids or cell wall materials characteristic of the target organism or a combination thereof. In some embodiments, the extracted microbe sample comprises the viable microbes. In some other embodiments, the extracted microbe sample comprises the lysed cell of the microbes. In yet some other embodiments, the extracted microbe sample comprises the characteristic or unique DNA or RNA of the microbes.

In some embodiments, the method further comprises lysing the microbes' cells in the extracted sample. The method for lysing cell can be heat, chemical lysing, electrical shock, or any other method known in the art.

In some embodiments, the cells are subject to diagnostics for detection. The cells can be subject to amplification or non-amplification-based diagnostics.

Preanalytical Sample Preparation

Detection of bacterial pathogens is a multi-step process preferably comprised of 1) a sampling step, 2) a sample-preparation step and 3) a detection step. Sampling involves application of well-established, statistically-validated approaches for product-specific analysis, prescribing the sampling procedures and number of samples needed to detect a certain level of microbes (if present) with a given degree of certainty. Sample preparation refers to the various procedures needed to process the raw sample so that it is amenable to further testing. In the case of microbial diagnostics, this involves various physical, chemical or combination treatments aimed at performing key functions, such as producing of a homogeneous sample, reducing sample volume, excluding or inactivating inhibitory substances, separating cells from food (or environmental or clinical) matrices, concentrating these cells and purifying them (removal of cell-associated assay inhibitors). Detection involves use of reagents and instruments for direct detection of organism-associated analytes (specific DNA or RNA sequences or other diagnostically-important cell features, such as unique proteins, enzymes, antigens, etc.). When proceeding from sample-to-answer, it is important to understand that inefficiencies at any of these independent, yet interdependent steps (sampling, sample preparation, detection) will propagate through the chain and impact the final results.

It is important to note that a single sample preparation step may be compatible with multiple downstream detection steps. For example, a short, slow centrifugation may be used as a means for selective sedimentation of large food particulates, while retaining the smaller and lighter bacterial cells in the supernatant. These supernatant-associated cells may then either be tested directly or subjected to further sample preparation, such as filtration, immunomagnetic separation or longer, faster centrifugation for concentration of bacterial cells (Brehm-Stecher et al., 2009).

We have found that use of MILs can provide a general, yet customizable platform for bacterial capture and concentration. Sample preparation ultimately allows a great deal of flexibility in assay construction. Our described use of MILs for preanalytical sample preparation of foods (Hice et al., 2019) accomplishes several of the ideal objectives of preanalytical sample preparation, including (capturing and) concentrating cells from the test matrix, purifying them, reducing the sample volume and producing a homogeneous sample. As MIL-based sample preparation is an independent step or module, the cells processed in this manner can be analyzed using any number of downstream detection approaches, which we categorize and describe further as "Amplification-Based Diagnostics" and "Non-Amplification-Based Diagnostics".

Amplification-Based Diagnostics

Amplification-based diagnostics are those that result in an enrichment of diagnostically-important biomolecules to levels where they can be easily detected. Example target molecules include nucleic acids (NA) such as DNA and RNA. An example of an amplification-based diagnostic test is the polymerase chain reaction (PCR) or its variants. With PCR, even a single pathogen-specific NA sequence can be exponentially enriched to a detectable level with high specificity and from complex samples containing high levels of non-target bacteria. Detection of an amplified NA sequence (an amplicon) by PCR provides evidence that the sequence, and therefore the pathogen of interest, was in the original sample. PCR depends on temperature cycling between denaturation, annealing and extension steps, or in abbreviated processes, denaturation and a combined annealing/extension step, which can provide efficiencies in speed, as it reduces cycling time. Certain advances, such as convective PCR (Krishnan et al., 2002) can accomplish temperature cycling by passage of a bolus of reagents through a temperature zones corresponding to denaturation and annealing/extension temperatures, but most commercial PCR applications remain dependent on specialized, dedicated cycling instruments.

An exciting development in nucleic acid diagnostics is the advent of isothermal amplification methods. The term "isothermal" refers to a process that occurs at a single, constant temperature. Isothermal NA amplification steps mimic cellular processes, which in higher organisms occur within temperature-regulated tissues and in bacteria at temperatures associated with the medium (water, food, etc.) in which the bacteria are growing. Isothermal NA amplification simplifies the equipment needed to generate pathogen-specific amplicons and are not limited by instrumental factors such as temperature cycling speed, allowing target organisms to be quickly identified in a sample. Several methods have been described for isothermal amplification of NA, these include, but are not limited to, transcription-mediate amplification (TMA), self-sustained sequence replication (3 SR), nucleic acid sequence-based amplification (NASBA), signal mediated amplification of RNA technology (SMART), strand displacement amplification (SDA), rolling circle amplification (RCA), loop-mediated isothermal amplification of DNA (LAMP), isothermal multiple displacement amplification (IMDA), helicase-dependent amplification (HDA), single primer isothermal amplification (SPIA), circular helicase-dependent amplification (cHDA) and recombinase polymerase amplification (RPA) (Gill and Ghaemi, 2003: Hice et al., 2019). Hice et al., (2019) coupled MIL-based capture and concentration of S. Typhimurium to RPA, using inexpensive and regenerable sodium acetate heat packs to drive RPA reactions, eliminating the need for an external power source. *Salmonella* RPA amplicons could be detected in <10 min using a simple chromatographic readout. This approach highlights the utility of MIL-based sample preparation in conjunction with isothermal NA amplification to provide a simple, streamlined detection method that is amenable to analyses in the field or in other resource-limited environments.

Preferably the amplification-based diagnostic is performed at a temperature of from about 20° C. to about 60° C., more preferably from about 20° C. to about 55° C., still more preferably from about 20° C. to about 50° C., even more preferably from about 25° C. to about 45° C., and most preferably from about 25° C. to about 40° C.

Non-Amplification-Based Diagnostics

Non-amplification-based diagnostics are those approaches that do not depend on targeted biomolecule amplification for detection of target organisms. This class of diagnostics is very broad and includes culture-based detection of bacteria using either non-selective or selective agars, labeling with fluorescent antibodies, fluorescence in situ hybridization (FISH) using RNA, DNA, peptide nucleic acid (PNA), locked nucleic acid (LNA) or other natural or synthetic probes capable of binding to NA via Watson-Crick pairing, spectroscopic methods including vibrational spectroscopy and mass spectroscopy, and others.

Another non-amplification-based diagnostic method is Gram-staining, which represents the first fundamental step towards identifying bacteria using classical bacteriological techniques. In the Gram staining process, unknown bacteria are heat fixed then exposed to a sequence of individual staining steps involving 1) crystal violet dye, 2) iodine, 3) a solvent (ethanol or acetone) and 4) safranin counterstain. Following this procedure, Gram observed that some bacteria retained crystal violet dye while some did not. Crystal violet-stained cells (purple) are referred to as "gram-positive". Cells that do not retain crystal violet are counterstained (pink) with safranin and are referred to as "gram-negative".

Many years later, it was determined that this differential staining is due to fundamental structural differences between the cell envelopes of these two classes of bacteria, with gram-positive bacteria having a single phospholipid membrane and a thick peptidoglycan layer in their cell wall which traps a crystal violet-iodine complex, preventing its removal during the solvent-based decolorization. Conversely, gram-negative bacteria have a double membrane structure and a much thinner peptidoglycan layer that does not retain the complex.

Although gram-positive and gram-negative bacteria differ in gross structure and members of the two bacterial lineages are physiologically and genetically diverse, their surfaces are adorned with similar classes of macromolecules, including polysaccharides and proteins. These macromolecules possess carboxylate, amino and phosphate moieties whose ionization state is dependent on environmental pH (Wilson et al., 2001). The molecular complexity of bacterial cells therefore gives rise to a commensurately complex distribution of surface charge. While the net surface charge of bacteria is negative, individual charged residues can interact, partner and bind with charged solutes (salts, peptides, nucleic acids, etc.) or with suspended molecular aggregates (solid particles such as cationic beads, metal hydroxides such as zirconium hydroxide, minerals such as hydroxyapatite, or liquid aggregates comprised of hydrophobic liquids such as magnetic ionic liquids).

Magnetic ionic liquids (MILs) are paramagnetic molten salts comprised of organic/inorganic cations and anions that exhibit melting points at or below about 100° C. In their use as bacterial capture reagents, MILs are added to aqueous sample suspensions and the suspension is vortexed thoroughly to form MIL microdroplets which then collide with bacteria in the sample. When MIL droplets collide with bacterial cells, we theorize that cationic and anionic MIL partners are able to interact with charged species on cell surfaces, facilitating electrostatic capture of the cells. Loss of coordinating ligands in the anionic component of the MIL may also occur, leaving the cationic metal free to interact with anionic species on bacterial surfaces, which could also promote cell capture. MIL interaction with bacterial cell surfaces is hypothesized to be driven by equilibrium theory, and factors such as strain-specific charge variability and the pH and ionic composition of the sample suspension medium are expected to promote or reduce binding.

Because the MILs are hydrophobic and denser than water, they eventually coalesce at the bottom of an aqueous food sample, a process which can be accelerated through use of an externally applied magnetic field. Consolidation of MIL droplet-bacterial cell complexes into a physically separated liquid phase leads to concentration of captured bacteria, which can then be eluted from the MIL surface by adding an ionically-rich liquid medium that favors displacement of MIL species, resulting in release of cells for downstream processing.

Structural components contributing to cell surface charge in gram-negative bacteria include the lipopolysaccharide outer membrane, a portion of which is referred to as the "0-antigen", polysaccharide capsular material in mucoid variants or in species forming capsule-enclosed aggregates of cells ("symplasmata", as with *Pantoea eucalypti*, which forms these multicellular structures containing hundreds of clonal cells bound within a thick polysaccharide envelope) and structures such as the repeat polysaccharide sequence known as the Enterobacterial Common Antigen (Octavia and Lan, 2014). Additional cell surface structures that contribute to the molecular and charge diversity of gram-negative bacteria include transmembrane proteins, fimbriae (also referred to as adhesins or pili)—stiff, hair-like appendages uniformly distributed across the cell surface and that mediate bacterial binding to host cells, two-dimensional, surface-associated protein arrays (S-layers) and flagella. Flagella (H-antigen) are whip-like structures that confer cell motility and whose number and surface arrangement may vary according to cell type (Octavia and Lan, 2014).

Structural components contributing to cell charge in gram-positive bacteria include those previously mentioned for gram-negative bacteria and include capsular polysaccharides, surface proteins, fimbriae (also called adhesins or pili), S-layers and flagella (Corbett et al., 2010; Melville and Craig, 2013; Messner et al., 2010). gram-positive bacteria also display teichoic acids (TA), which fortify cell wall rigidity by complexing with metal ions, including magnesium and sodium (Rajagopal and Walker, 2017). TA anchored to cell membrane lipids are referred to as "lipoteichoic acids". Those attached covalently to cell wall peptidoglycan are referred to as "cell wall teichoic acids". D-alanine ester or D-glucosamine modification of cell wall TA can impart zwitterionic character to these molecules (Kohler et al., 2009; Rautenberg et al., 2010).

Considering the information provided above, both gram-negative and gram-positive bacteria possess and display similar classes of macromolecules at their surfaces. Despite expected differences in polysaccharide or protein sequences among different bacteria, these macromolecules are expected to behave similarly, acting as key mediators of overall cell charge and serving as substrates for partitioning of MIL components, resulting in electrostatic binding and capture of cells. By adjusting the ionic environment, the binding equilibrium can be shifted to promote elution of captured cells back into aqueous suspension for downstream analysis.

Sample Preparation

While no preanalytical sample preparation method can be considered universal, it is reasonable to expect, by those skilled in the art of bacterial detection techniques, that MIL-based capture and concentration of bacteria can be effectively coupled with many different types of detection techniques, beyond what we have already reduced to practice (qPCR, RPA, non-selective agars, selective agars).

After sample preparation, collected bacteria cells can be subjected to direct visual detection via optical methods such as microscopy or flow cytometry, with or without application of macromolecule-specific chemical stains (stains indicating the presence of DNA, RNA, proteins, lipids, carbohydrates, etc.). Alternatively, cells can be processed for whole-cell molecular detection using rRNA-targeted fluorescent probes. These same cells may also be processed further via heat and/or chemical treatment for fractional analysis of diagnostic cellular components such as nucleic acids, using amplification-based methods such as PCR or chemically-enhanced approaches such as Enzyme-Linked Immunosorbent Assay (ELISA). These examples highlight the inherent generality of many preanalytical sample preparation techniques, where a single method for capture and concentration of bacterial cells from a sample may provide output that is suitable for multiple downstream testing methods.

RPA

In some embodiments, the RPA is applied to the extracted microbe sample for amplifying characteristic DNA or RNA of the microbes at a temperature of from about 20° C. to about 50° C., from about 20° C. to about 25° C., from about 20° C. to about 30° C., from about 20° C. to about 35° C., from about 20° C. to about 40° C., from about 20° C. to about 45° C., from about 25° C. to about 50° C., from about 25° C. to about 45° C., from about 25° C. to about 40° C., from about 25° C. to about 35° C., from about 30° C. to about 50° C., from about 30° C. to about 45° C., from about 35° C. to about 50° C., from about 35° C. to about 45° C., from about 37° C. to about 42° C., or about values there between.

In some embodiments, wherein the microbes are *Salmonella* and the RPA comprises using a DLH primer. In some other embodiments, the microbes are *Salmonella* and the RPA comprises using an invA primer.

In some embodiments, "using Recombinase Polymerase Amplification (RPA) on the extracted sample for amplifying DNA or RNA of the microbes" comprises using a power-free-heat source for RPA. As used herein, "a power-free-heat source" means a tool or device that can provide heat for RPA to be carried out at a temperature or temperature range, without using electricity at the same time. A power-free-heat source may be a battery-powered heating device (heating pad, adjustable hot plate, infrared heating lamp, etc.) or any device utilizing chemical reaction(s), solar energy, or light to generate heat, or any device capable of maintaining an appropriate RPA incubation temperature without using electricity.

In some embodiments, the claimed method comprises using a battery-powered heat source for RPA. In some other embodiments, the claimed method comprises using a chemical heat source for RPA.

The existence or absence of the amplified DNA or RNA sequences after RPA with specific primer(s) or primer set(s), which should be unique or characteristic for specific microbe(s), can be detected or confirmed by a proper and routine tool or device known to one skilled in the art for amplicon detection.

In some embodiments, the method disclosed herein further comprising detecting the amplified DNA using an amplicon detection tool or device. In some embodiments, the detection tool or device is gel electrophoresis. In some other embodiments, the detection tool or device is a nucleic acid lateral flow immunoassay (NALFIA).

Detection of pathogen-specific amplicons via NALFIA uses generic materials, with specificity provided by pathogen-specific primers. In some other embodiments, a diagnostic detection tool or device can be purchased commercially. A typical detection tool or device usually includes an absorbent pad (a reservoir where the sample is placed), a paper or nitrocellulose membrane that serves as a support for wicking/movement of the mobile phase containing amplified DNA and that is imprinted with at least two perpendicular reagent lines bound to the membrane. These lines include a line consisting of anti-fluorescein antibody (sample line) and a line consisting of biotin (control line).

Two pathogen-specific primers can be used for the amplification step, one labeled with fluorescein and the other labeled with biotin. When DNA is amplified, a double-stranded amplicon is formed, labeled at one end with fluorescein and at the other with biotin. Also mobilized by wicking of the amplicon-containing sample, are streptavidin-labeled gold nanoparticles. As it moves across the sample line, the fluorescein-labeled end of the amplicon binds to the anti-fluorescein antibody on the membrane, immobilizing the amplicon. The nanoparticles bind to the biotin-labeled end of the amplicon, their aggregation at this line forms a visible red color, indicating presence of the amplicon. Additional nanoparticles bind to the biotin that is immobilized at the control line, providing a visual indicator that the assay is working properly, so that absence of a signal at the sample line represents absence of target and not a faulty assay.

In other embodiments, other approaches that involve enzymatic labels, such as horseradish peroxidase, can signal the presence of an amplicon through generation of colorimetric or fluorescent (more sensitive) signals.

In some embodiments, the magnetic ionic liquid used in the methods or kits disclosed herein comprises a paramagnetic anionic component and a cationic component or a paramagnetic cationic component and an anionic component. In a preferred embodiment, the MIL comprises a paramagnetic anionic component and a cationic component, wherein the cationic component has a general formula (I)

$$[(PR^1R^2R^3R^4)^+]  \qquad (I)$$

wherein each of $R^1$, $R^2$, $R^3$, and $R^4$ is independently an unsubstituted or substituted alkyl; the paramagnetic anionic component (P) has the following general formula (II), $$[M(Y)_x^-]  \qquad (II)$$

wherein M is transition metal or rare earth metal ion; and Y is a chelating agent having the general formula (III),

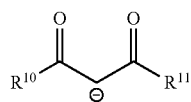
(III)

each of $R^{10}$ and $R^{11}$ is independently a substituted or unsubstituted methyl, phenyl, thiophenyl, napthyl, alkyl, or aryl group; and x is 3 or 4.

In a preferred embodiment, the MIL comprises a paramagnetic anionic component and a cationic component, wherein the cationic component has a general formula (IV) or (V) as shown below:

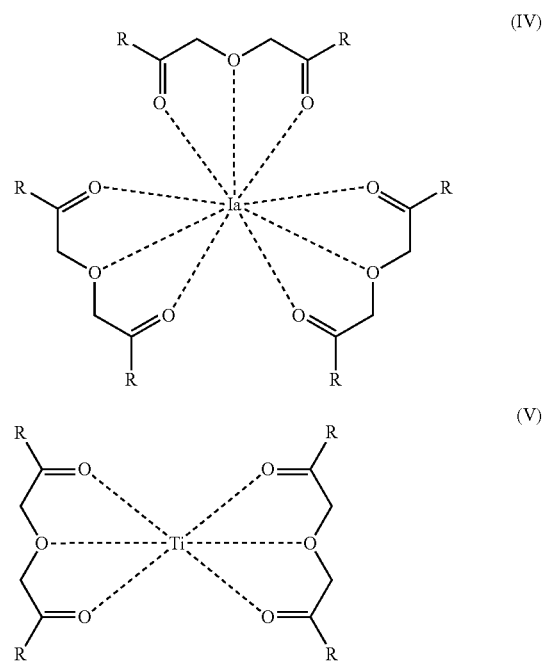

wherein R is one or more of the following:

In a preferred embodiment, the MIL comprises a paramagnetic cationic component and an anionic component, wherein the anionic component has the general formula (VI) or (VII) as shown below:

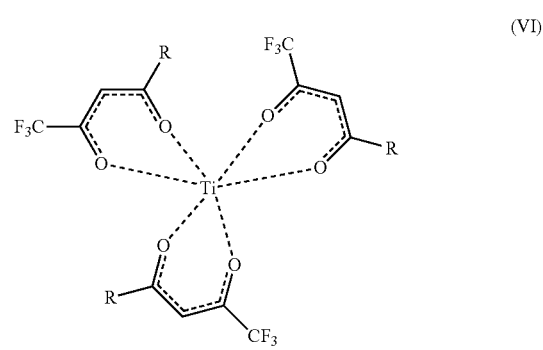

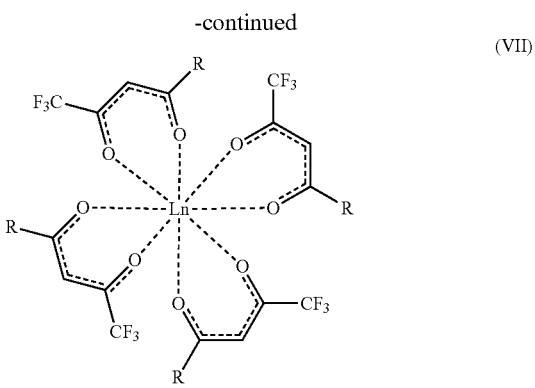

(VII)

wherein R is one or more of the following:

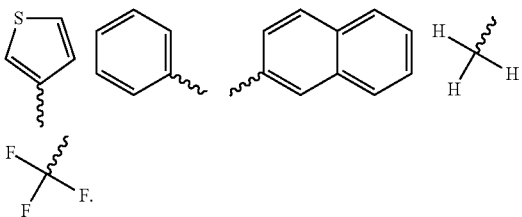

In Formulas IV, V, VI, and VII, Ti comprises Co, Ni, Mn or a combination thereof and Ln comprises Dy, Gd, Ho, or a combination thereof.

In some embodiments, in the magnetic ionic liquid disclosed herein, M is a transition metal ion. In some other embodiments, M is Co, Mn, Ni, or combination thereof.

In some embodiments, in the magnetic ionic liquid disclosed herein, M is a rare earth metal ion. In some other embodiments, M is Dy, Nd, Gd, or a combination thereof. In yet some other embodiments, M is a mixture of a transition metal ion and rare earth ion. In some other embodiments, M is Co, Mn, Ni, Dy, Nd, Gd ion, or a combination thereof.

In some embodiments, for the magnetic ionic liquid disclosed herein, $R^{10}$ and $R^{11}$ are independently a methyl, phenyl, thiophenyl, napthyl, alkyl, or aryl group substituted by one or more electron withdrawing halogens or other groups. In some other embodiments, $R^{10}$ and $R^{11}$ are independently a C1-C4 alkyl group substituted by one or more electron withdrawing halogens or other groups. In some other embodiments, $R^{10}$ and $R^{11}$ are independently a $CH_3$, $CHF_2$, $CH_2F$, or $CF_3$ group. In yet some other embodiments, $R^{10}$ and $R^{11}$ are independently a $CF_3$ group.

In some other embodiments, for the magnetic ionic liquid disclosed herein, the anionic component is [Co(hfacac)$_3^-$], [Ni(hfacac)$_3^-$], ([Mn(hfacac)$_3^-$]), ([Dy(hfacac)$_4^-$]), ([Gd(hfacac)$_4^-$]), ([Nd(hfacac)$_4^-$]), or combination thereof, wherein hfacac is

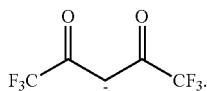

In some embodiments, for the magnetic ionic liquid disclosed herein, the cationic component is [(PR$^1$R$^2$R$^3$R$^4$)$^+$], wherein each of $R^1$, $R^2$, $R^3$, and $R^4$ is independently an unsubstituted or substituted alkyl. In other embodiments, each of $R^1$, $R^2$, $R^3$, and $R^4$ is independently a straight-chain or branched alkyl. In other embodiments, each of $R^1$, $R^2$, $R^3$, and $R^4$ is independently an $C_2$-$C_{20}$ unsubstituted alkyl. In other embodiments, each of $R^1$, $R^2$, $R^3$, and $R^4$ is independently an $C_2$-$C_{20}$ straight-chain or branched alkyl. In some other embodiments, at least one of $R^1$-$R^4$ group is different from the others in the cationic component. In some other embodiments, each of $R^1$, $R^2$, $R^3$, and $R^4$ is independently an $C_2$-$C_{20}$ unsubstituted alkyl, and at least two of $R^1$, $R^2$, $R^3$, and $R^4$ are the same. In yet some other embodiments, each of $R^1$, $R^2$, $R^3$, and $R^4$ is independently an $C_2$-$C_{20}$ unsubstituted alkyl, and three of $R^1$, $R^2$, $R^3$, and $R^4$ are the same. In some other embodiments, each of $R^1$, $R^2$, and $R^3$ is independently a $C_6$ alkyl, and $R^4$ is a $C_{14}$ alkyl. In some other embodiments, each of $R^1$, $R^2$, and $R^3$ is independently a straight-chain $C_6$ alkyl, and $R^4$ is a straight-chain $C_{14}$ alkyl.

An important feature of both the Ni(II) and Co(II) MILs is that they are cell-compatible, unlike other ILs reported for analysis of bacteria. For example, the [EMIM$^+$][SCN$^-$] IL has been previously investigated for solubilization of protein-rich food matrices as a means for sample preparation (Mester et al., 2010). The [EMIM$^+$] cation potentially acts as a detergent, while the [SCN$^-$-] anion is chaotropic. The capacity to use this IL to physically obliterate difficult food matrices, then collect released bacterial cells for analysis represents a novel advance in sample preparation. However, a major limitation of this approach is the discovery by the original authors that [EMIM$^+$][SCN$^-$] is injurious to *Salmonella* Typhimurium in this application, with only 34-45% of inoculated S. Typhimurium recovered after IL-mediated matrix lysis when plated to a selective agar (Mester et al., 2010). In our hands, when S. Typhimurium was exposed to [EMIM$^+$][SCN$^-$] as originally described for IL-based extraction of this pathogen from foods (Mester et al., 2010), no recovery was observed on either TSA or BSA, confirming the injurious nature of this IL in stark contrast to and in direct comparison with the "cell-friendly" Ni(II) MIL. The same group has reported the use of the hydrophobic IL 1-butyl-1-methylpyrrolidinium bis(trifluoromethylsulfonyl)imide ([BMPyr$^+$][Ntf$_2^-$]) for use as a medium for thermal (120° C.-150° C.) disintegration of gram-negative cells in support of pre-analytical DNA sample preparation (Fuchs-Telka, et al, 2017). These authors note that, in this application, " . . . *Salmonella* Typhimurium and *E. coli* are completely disrupted by [BMPyr$^+$][Ntf$_2^-$] . . . " (Fuchs-Telka, et al, 2017).

In contrast, we used differential plating on non-selective and selective agars, various MIL exposure times and a highly chemically-sensitive O-antigen-deficient *S. Minnesota* mutant to demonstrate that the Ni(II) MIL possesses no overt antimicrobial activities against bacteria tested. These results also highlight the suitability of the Ni(II) MIL for integration into detection schemes involving the use of selective media screens.

In some embodiments, the magnetic ionic liquid disclosed herein is water insoluble, indicated by exhibiting no observable change in color or pH of either the MIL or aqueous phase, or by that the MIL droplets still responded readily to an external magnetic field after three days of suspension in the aqueous phase. In other embodiments, the magnetic ionic liquid disclosed herein has a solubility of less than about 0.01% (v/v) in water. In other embodiments, the magnetic ionic liquid disclosed herein has a solubility of less than about 0.05% (v/v), about 0.04% (v/v), about 0.03% (v/v), about 0.02% (v/v), about 0.009% (v/v), about 0.008% (v/v), about 0.007% (v/v), about 0.006% (v/v), about 0.005% (v/v), about 0.004% (v/v), about 0.003% (v/v), about 0.002% (v/v), about 0.001% (v/v), or any value therein between in water.

In some embodiments, the magnetic ionic liquid disclosed herein has a viscosity of from about 150 cp to about 1,000 cp at the temperature of 23.7° C. In some other embodiments, the magnetic ionic liquid disclosed herein has a viscosity of from about 200 cp to about 950 cp, from about 250 cp to about 900 cp, from about 300 cp to about 850 cp, from about 350 cp to about 800 cp, from about 400 cp to about 750 cp, from about 450 cp to about 700 cp, from about 500 cp to about 650 cp, from about 550 cp to about 600 cp, about 900 cp, about 800 cp, about 700 cp, about 600 cp, about 500 cp, about 400 cp, about 300 cp, about 200 cp, or any value therein between at the temperature of 23.7° C.

In some embodiments, the magnetic ionic liquid disclosed herein has a thermal stability indicated by an onset of decomposition starting at about 110° C. or above. In some embodiments, the magnetic ionic liquid disclosed herein has a thermal stability indicated by an onset of decomposition starting at about 120° C., about 100° C., about 95° C., about 90° C., about 85° C., about 80° C., about 75° C., about 70° C., about 65° C., about 60° C., about 55° C., about 50° C., about 45° C., or any value therein between.

In some embodiments, the magnetic ionic liquid disclosed herein has a magnetic susceptibility from about 2.5 µB to about 10.0 µB, measured by a Quantum Design MPMS SQUID magnetometer. In some embodiments, the magnetic ionic liquid disclosed herein has a magnetic susceptibility from about 0.5 µB to about 3.0 µB, from about 2 µB to about 10 µB, from about 1 µB to about 5 µB, from about 1 µB to about 10.0 µB, from about 2 µB to about 10 µB, from about 3 µB to about 10.0 µB, from about 1 µB to about 5 µB, from about 5 µB to about 10.0 µB, about 10, about 9, about 8, about 7, about 6, about 5, about 4, about 3, about 2, about 1, about 0.5, about 0.2, or any value therein between as measured by a Quantum Design MPMS SQUID magnetometer.

In some embodiments, the magnetic ionic liquid disclosed herein is soluble in hexane, heptane, toluene, and benzene at 10% (v/v) MIL to solvent ratio, in acetone, acetonitrile, chloroform, dichloromethane, dioxane, ethanol, ethyl acetate, diethyl ether, methanol, or isopropyl alcohol at 20% (v/v) MIL to solvent ratio, or in hexane, heptane, toluene, and benzene at 20% (v/v) MIL to solvent ratio.

In some embodiments, the magnetic ionic liquid has a solubility of greater than about 10% (v/v) in an organic solvent (except DMSO). In some other embodiments, the magnetic ionic liquid has a solubility of greater than about 20% (v/v) in an organic solvent (except DMSO). In some other embodiments, the magnetic ionic liquid has a solubility of greater than about 1% (v/v), about 2% (v/v), about 3% (v/v), about 4% (v/v), about 5% (v/v), about 6% (v/v), about 7% (v/v), about 8% (v/v), about 9% (v/v), about 10% (v/v), about 11% (v/v), about 12% (v/v), about 13% (v/v), about 14% (v/v), about 15% (v/v), about 16% (v/v), about 17% (v/v), about 19% (v/v), or any value therein between in an organic solvent (except DMSO).

In some embodiments, the magnetic ionic liquid disclosed herein can extract viable microbes from a sample comprising the microbes. In some embodiments, the magnetic ionic liquid disclosed herein can preconcentrate viable microbes or their diagnostically useful cellular components, including, but not limited to DNA, RNA, other nucleic acids, proteins, enzymes, lipids or cell wall materials characteristic of the target organism, from a sample comprising the microbes. As used herein, "preconcentrate" means that the viable microbes or their diagnostically useful cellular components, including, but not limited to DNA, RNA, other nucleic acids, proteins, enzymes, lipids or cell wall materials characteristic of the target organism, has a higher concentration in the MIL than in the sample after the MIL is mixed with the sample.

In some embodiments, for the method of extracting, concentrating, detecting viable microbes, the magnetic ionic liquid has a higher concentration of the microbes or their diagnostically useful cellular components, including, but not limited to DNA, RNA, other nucleic acids, proteins, enzymes, lipids or cell wall materials characteristic of the target organism, than the sample, after the contacting step. In some embodiments, the ratio of the microbe concentration in the magnetic ionic liquid to one in the sample is from about 1:1 to about 50:1. In some embodiments, the ratio of the microbe concentration in the magnetic ionic liquid to one in the sample is from about 1:1 to about 25:1, from about 1:1 to about 20:1, from about 1:1 to about 15:1, from about 1:1 to about 10:1, or from about 1:1 to about 5:1. In some embodiments, the microbe or its diagnostically useful cellular components, including, but not limited to DNA, RNA, other nucleic acids, proteins, enzymes, lipids or cell wall materials characteristic of the target organism, concentration in the magnetic ionic liquid is higher than one in the sample after the contact time. In some embodiments, the microbe concentration in the magnetic ionic liquid can be lower than in the sample after the contact time.

In some embodiments, the ratio of the microbe concentration in the magnetic ionic liquid to one in the sample is from about 1:1 to about 2:1, from about 1:1 to about 40:1, about 1:1, about 5:1, about 10:1, about 15:1, about 20:1, about 25:1, about 30:1, about 35:1, about 40:1, about 50:1, or any value therein between.

In some embodiments, for the method of extracting, concentrating, detecting viable microbes, the magnetic ionic liquid has a lower concentration of the microbes or their diagnostically useful cellular components, including, but not limited to DNA, RNA, other nucleic acids, proteins, enzymes, lipids or cell wall materials characteristic of the target organism, than the sample, after the contacting step.

In some embodiments, for the method of extracting, concentrating, detecting viable microbes, the weight ratio between the magnetic ionic liquid and the sample is between about 1:10 to about 1:100. In some embodiments, for the method of extracting, concentrating, detecting microbes, the weight ratio between the magnetic ionic liquid and the sample is between about 1:10 to about 1:20, between about 1:10 to about 1:30, between about 1:10 to 1:40, between about 1:10 to 1:50, between about 1:10 to 1:60, between about 1:70 to 1:80, between about 1:10 to 1:90, between about 10:1 to 1:10, between about 1:20 to 1:50, between about 1:20 to 1:100, between about 1:40 to 1:80, between about 1:50 to 1:10, between about 1:10 to 1:20, about 10:1, about 5:1, about 1:1, about 1:5, about 1:10, about 1:20, about 1:30, about 1:40, about 1:50, about 1:60, about 1:70, about 1:80, about 1:90, about 1:100, or any value therein between.

In some embodiments, for the method of extracting, concentrating, detecting microbes, the viable microbes have a concentration of at least $10^3$ or $10^4$ CFU/mL in the sample or liquid part of the sample.

In some embodiments, for the method of extracting, concentrating, detecting microbes, wherein the sample is a heterogeneous aqueous solution. In some other embodiments, the sample is a heterogeneous aqueous solution comprising food, milk, juice, biological fluid, blood, or any suspended food solid. In yet some other embodiments, the sample is an aqueous solution comprising milk, juice, biological fluid, or blood. In some other embodiments, the sample is an aqueous solution comprising or suspended with any material that can host viable microbes. In yet some other embodiments, the sample comprises soil that can host the microbes.

In some embodiments, for the method of extracting, concentrating, detecting microbes, the contact time for the extracting step is from about 30 seconds to about 10 min. In some embodiments, the contact time is from about 1 minute to about 1 hour, from 1 minute to about 2 hours, from 1 minute to about 5 hours, from about 1 hour to 24 hours, about 5 minutes, about 10 minutes, about 2 minutes, about 1 hour, about 2 hours, about 5 hours, about 10 hours, or any value therein between.

In some embodiments, during the contact time, a manual or mechanical method is utilized to maximize the contact between the MIL and the food sample for the whole contact time or only for a part of the contact time.

In some embodiments, the method of extracting, concentrating, detecting microbes further comprises mixing the sample and magnetic ionic liquid during contact time through manual or mechanical agitation after the contacting step starts. Vortexing and hand shaking are examples of agitation to maximize the interaction between the MIL and the sample.

In some embodiments, the method of extracting, concentrating, detecting microbes further comprises separating the magnetic ionic liquid from the sample by a magnetic field. In some other embodiments, the method further comprises separating the magnetic ionic liquid from the sample by a magnetic field of from about 0.1 tesla to about 2 tesla.

In some embodiments, the method of extracting, concentrating, detecting microbes comprises extracting the microbes or their diagnostically useful cellular components, including, but not limited to DNA, RNA, other nucleic acids, proteins, enzymes, lipids or cell wall materials characteristic of the target organism, from the magnetic ionic liquid to an aqueous extracting medium. In some embodiments, the aqueous extracting medium is a nutrient broth, salt solution, or aqueous medium that recovers the microbes or their diagnostically useful cellular components, including, but not limited to DNA, RNA, other nucleic acids, proteins, enzymes, lipids or cell wall materials characteristic of the target organism, from the MIL.

In some embodiments, the method of extracting, concentrating, detecting microbes further comprises enriching, culturing, or multiplying the microbes extracted from the sample by the MIL and/or the extracting medium. The techniques are any one of those that would be used by one skilled in the art to increase population of microbes.

In some other embodiments, the method further comprises using mass/flow cytometry for detecting characteristic DNA of the microbes. In yet some other embodiments, the method further comprises using a culture-based method to multiply and identify the microbes.

In another aspect, disclosed herein is a kit for extracting, concentrating, detecting microbes from a sample, the kit comprises a magnetic ionic liquid and an enzyme for Recombinase Polymerase Amplification (RPA), wherein the magnetic ionic liquid comprises a paramagnetic anionic component and a cationic component, wherein the cationic component has a general formula (I);

$[(PR^1R^2R^3R^4)^+]$ (I);

wherein each of the $R^1$, $R^2$, $R^3$, and $R^4$ is independently an unsubstituted or substituted alkyl;

wherein the paramagnetic anionic component has the following general formula (II),

$[M(Y)_x^-]$ (II)

wherein M is transition metal or rare earth metal ion; and Y is a chelating agent having the general formula (III),

(III)

each of the $R^{10}$ and $R^{11}$ are independently a substituted or unsubstituted methyl, phenyl, thiophenyl, napthyl, alkyl, or aryl group; and x is 3 or 4.

In some embodiments, the magnetic ionic liquid is one disclosed herein in this disclosure.

In another aspect, disclosed herein is a kit for extracting, concentrating, detecting viable microbes from a sample, the kit comprises a magnetic ionic liquid as disclosed herein; an enzyme for Recombinase Polymerase Amplification (RPA); and a power-free heat source.

In another aspect, disclosed herein is a kit for extracting, concentrating, detecting viable microbes from a sample, the kit comprises a magnetic ionic liquid as disclosed herein; an enzyme for Recombinase Polymerase Amplification (RPA); and an extracting medium; wherein the extracting medium comprises more than 10 g/L of tryptone, 10 g/L of NaCl, 5 g/L of yeast extract, or combination thereof.

In yet another aspect, disclosed herein is a kit for extracting, concentrating, detecting viable microbes from a sample, the kit comprises a magnetic ionic liquid as disclosed herein; an enzyme for Recombinase Polymerase Amplification (RPA); and a primer for RPA, wherein the primer is one for Salmonella-specific DLH gene.

In some embodiments, wherein the extracting medium is a Luria-Bertani-derived nutrient broth comprising more than 10 g/L of tryptone, more than 5 g/L of yeast extract, more than 10 g/L of NaCl, or combination thereof. In some other embodiments, the extracting medium is a Luria-Bertani-derived nutrient broth comprising from more than 10 g/L to about 20 g/L of NaCl, from more than 10 g/L g/L to about 20 g/L of tryptone, from more than 5 g/L to about 20 g/L of yeast extract, or combination thereof.

In some embodiments, the kit further comprises an extracting medium. In some other embodiments, the extracting medium enhances the microbes' or their diagnostically useful cellular components', including, but not limited to DNA, RNA, other nucleic acids, proteins, enzymes, lipids or cell wall materials characteristic of the target organism, recovery, compared to using water. In some embodiments, the extracting medium is a Luria-Bertani-derived nutrient broth. In some other embodiments, the extracting medium comprises tryptone, yeast extract, NaCl, or combination thereof. In yet some other embodiments, the extracting medium is a Luria-Bertani-derived nutrient broth comprising tryptone, yeast extract, NaCl, or combination thereof.

In some embodiments, the kit further comprises a primer or primer set for RPA specifically designed for the microbes. In some other embodiments, the kit further comprises a primer or primer set for RPA specifically designed for Salmonella. In yet some other embodiments, the kit further comprises a DLH primer or primer set for RPA specifically designed for Salmonella. In some embodiments, the primer set is (Forward primer) 5'-GCC GGG CAG CRA TTA TTC TGC ATG AA-3' (SEQ ID NO: 1) and (Reverse primer) 5'-TGG CGT ATA CGG GAA CCG TAA TAG CA-3' (SEQ ID NO: 2).

In some embodiments, the kit further comprises a reverse transcriptase (RT). The RT enzyme generates a complementary DNA (cDNA) from the single-stranded rRNA template and the RPA enzyme system can use this cDNA as a substrate for DNA amplification.

In some embodiments, the kit further comprises a power-free heat source. In some other embodiments, the kit further comprises a chemical heat pack for RPA. A chemical heat pack is based on exothermic chemical reactions and may be regenerable. In some other embodiments, the kit further comprises a portable heat source for RPA powered by a battery or solar energy or light.

In some embodiments, the kit further comprises an amplicon detection tool or device. In some embodiments, the amplicon detection tool is a nucleic acid lateral flow immunoassay (NALFIA) disposable cartridge.

As used herein, a chemical heat source refers to a device that generate heat solely from the chemicals within the device, without using or transforming any other energy source, such as mechanical or electrical source into heat. A chemical heat source includes, but is not limited to, super-cooled, food-grade sodium acetate pack.

As used herein, a portable heat source is a power-free heat source and includes a battery-powered heat source or a solar-powered heat source. As used herein, a battery-powered heat source refers to a device that convert the energy stored in a battery into heat. A battery-powered heat source includes, but is not limited to, a USB-powered incubator or battery powered infrared lamp.

As used herein, a solar-powered heat source refers to a device that convert the solar energy or natural light into heat.

As used herein, a power tool or a power equipment refers to a device that consumes electricity for performing its intended function.

As disclosed herein, a method of using a class of magnetic ionic liquids (MILs), which have very low water solubility, tunable chemical structure, low viscosity, suitable hydrophobicity and greater magnetic susceptibility, and RPA for determining microbes' identity and concentration is described. A kit for carrying out the disclosed method is also described.

Using the disclosed MILs for extraction or preconcentration of microbes can speed up the detection, identification, or quantification of the microbes, because the MILs can preconcentrate the microbes or eliminate other factors that might interfere or prevent the detection of the microbes. By dispersing hydrophobic MILs in an aqueous sample comprising microbes, the microbes can be rapidly extracted and isolated using an applied magnetic field. The extracted microbes were recovered from the MIL extraction phase by agitation in an extracting medium and subsequently the characteristic DNA of the microbes is amplified by RPA in a constant temperature.

Interestingly, the enrichment of viable *Salmonella* bacteria by MILs was dependent upon the identity of the paramagnetic metal incorporated into the chemical structure of the MIL, providing a basis for the design of MILs to exhibit enhanced cell extraction performance. Under optimized conditions, the MIL comprised of a trihexyl(tetradecyl) phosphonium cation ($[P_{6661}^+]$) and Ni(II) hexafluoroacetylacetonate-based anion ($[Ni(hfacac)_3^+]$) was capable of enriching sufficient viable cells for the detection of viable *Salmonella* bacteria concentrations as low as about $10^4$ CFUs mL$^{-1}$ in a food sample with an extraction/recovery procedure of less than 10 min. The MIL-based extraction method was also coupled with RPA amplification for the rapid analysis of viable *Salmonella* bacteria, demonstrating the compatibility of MILs with both culture-based and nucleic acid-based methodologies for viable *Salmonella* bacteria detection.

Extracting or concentrating microbes from a sample and then using RPA to amplify microbes' characteristic DNA is one of the approaches to improve the existing microbe testing throughput, since doing so decreases the amount of time for proper identification and quantification. Furthermore, the methods or kits disclosed herein make microbes' detection and identification on site or in field possible, without the need for any power equipment or tool.

All publications, patent applications, issued patents, and other documents referred to in this specification are indicative of the level of ordinary skill in the art to which this disclosure pertains and are herein incorporated by reference to the same extent as if each individual publication or patent application was specifically and individually indicated as incorporated by reference. Definitions that are contained in text incorporated by reference are excluded to the extent that they contradict definitions in this disclosure.

EXAMPLES

Embodiments of the disclosed methods are further defined in the following non-limiting Examples. These Examples, while indicating certain embodiments of the disclosed methods, are given by way of illustration only and should not be considered as limiting in any way. From the above discussion and these Examples, one skilled in the art can ascertain the essential characteristics of this disclosure, and without departing from the spirit and scope thereof, can make various changes and modifications of the embodiments of the disclosed methods to adapt it to various usages and conditions. Thus, various modifications of the embodiments of the disclosed methods, in addition to those shown and described herein, will be apparent to those skilled in the art from the foregoing description. Such modifications are also intended to fall within the scope of the appended claims.

Materials and Methods—Examples 1 to 6

Magnetic Ionic Liquids

The structures of the exemplary MIL solvents are shown in FIG. 1A. Synthesis and characterization of the MILs was performed as previously described in U.S. patent application Ser. No. 15/950,916. The MIL solvents were purified by liquid-liquid extraction with acetonitrile/hexane and dried in vacuo. The MILs were kept for long-term storage in capped glass vials and MILs were stored in a desiccator for at least 24 h prior to use.

Bacteria and Culture Conditions

*Serratia marcescens* (originally from Carolina Biological Supply Company, Burlington, NC, USA) was sourced from a teaching lab at Iowa State University. *Salmonella enterica* subspecies *enterica* ser. Typhimurium ATCC 14028 and *Escherichia coli* ATCC 25922 were from the American Type Culture Collection (ATCC, Manassas, VA, USA). Overnight cultures (10 mL) of *S. marcescens* were grown at 25° C. in 250 mL glass Erlenmeyer flasks containing Luria Bertani (LB) broth (Becton, Dickinson and Company [BD], Franklin Lakes, NJ, USA) supplemented with 1% (wt/vol) glycerol to accelerate production of the red pigment prodigiosin. Flasks were incubated with shaking at 190 rpm in a Shel Lab Shaking Incubator (Sheldon Manufacturing, Inc., Cornelius, OR, USA). S. Typhimurium and *E. coli* were grown in 14 mL polystyrene round-bottom tubes (Corning Inc., Corning, NY, USA) containing 10 mL Tryptic Soy Broth (TSB) (BD), and incubated at 37° C. in a Lab-Line Imperial III Incubator (Thermo Fisher Scientific, Waltham, MA, USA). Organisms were enumerated using Tryptic Soy Agar (TSA) plates (BD).

Pasteurized Liquid Food Products

Two-percent milk (Hy-Vee Reduced Fat Milk), almond milk (Hy-Vee All Natural Original), and a liquid egg product (Hy-Vee 99% Real Egg) were purchased from a local grocery store (Hy-Vee, Ames, IA) for evaluation of MIL-based capture in liquid food products. All foods were evaluated before the "Sell by", "Best if used by" or "Use by" dates listed on their packaging.

MIL-Based Extraction of Viable Bacteria

Figure 1B:
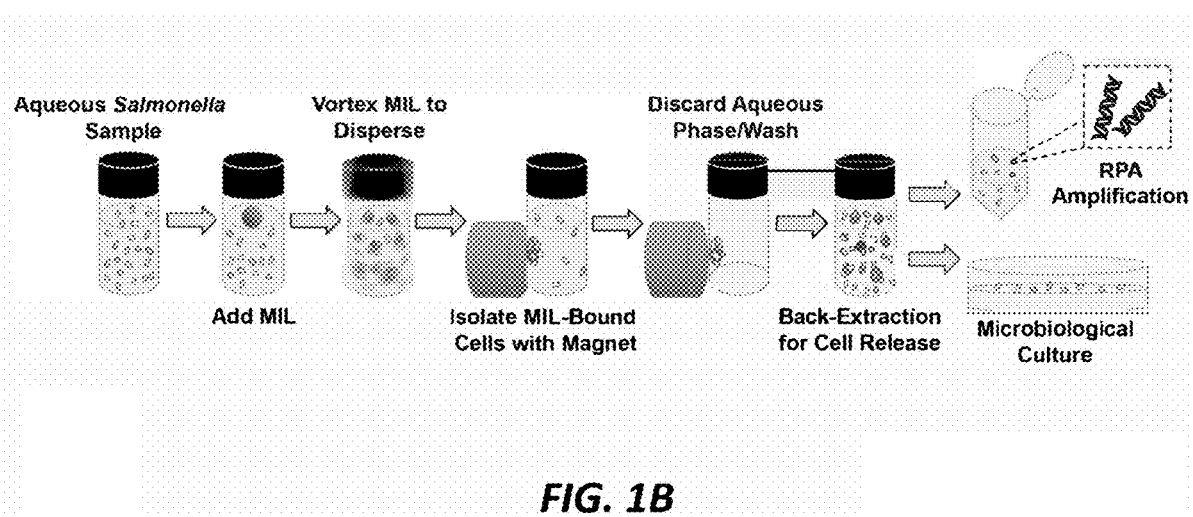
FIG. 1B shows the schematic for the extraction and preconcentration of Salmonella Typhimurium from aqueous food samples, followed by downstream analysis using RPA amplification and microbiological culture detection methods.

A representative schematic for the MIL-based extraction of bacteria is depicted in FIG. 1B. A 1 mL aliquot of diluted cell suspension, artificially spiked milk, almond milk, or liquid egg product was added to a 2 mL or 4 mL screw cap glass vial. A small volume of MIL (e.g., 15 µL) was added and vortexed vigorously for 30 s to create a cell-capturing microdroplet dispersion. With some samples (e.g. the egg product, due to viscosity and foaming), a magnet was applied externally to concentrate the cell-enriched MIL, although this step was not necessary with some samples, as the hydrophobic, denser-than-water MIL droplets were able to sink to the bottom of the extraction vial.

After gravity-based deposition or magnetic extraction, the aqueous phase was then discarded, and the MIL was subjected to a brief wash step using 1 mL of nuclease-free water (Integrated DNA Technologies, Coralville, IA, USA), to ensure adequate removal of residual bacteria that were not captured by the MIL microdroplets.

Recovery of viable cells from the MIL extraction phase was achieved through a "back-extraction" step that involved vortexing the cell-enriched MIL in 1 mL or 200 µL of a Luria Bertani-derived nutritive medium comprised of tryptone (20 g/L; "2× tryptone") and NaCl (10 g/L; "1×NaCl") for 2 min.

After back-extraction, captured bacteria were detected using microbiological culture or RPA. Prior to RPA, the cell-enriched back-extraction media was heated at 100° C. for 10 min for cell lysis and release of target nucleic acids. The MIL-RPA method was compared to a commercial nucleic acid sample preparation approach using the PrepMan Ultra Sample Preparation Reagent (PMU; Life Technologies, Carlsbad, CA, USA) according to the manufacturer's instructions.

Plating and Enumeration

Following back-extraction, aliquots of the cell-enriched modified LB media were serially diluted in 0.1% peptone water. A 10 µL aliquot of each dilution was applied to the appropriate lane on square, gridded TSA plates. The track plates were then tilted at an approximately 80° angle for 15 min to allow the deposited liquid to travel toward the opposite end of the plate. Plates were incubated for 48 hours at 25° C. (*S. marcescens*) or for 24 h at 37° C. (S. Typhimurium). Colonies were manually counted for determination of the number of CFUs in each sample. The enrichment factor ($E_F$) for the MIL-based method was calculated using Equation (1), where $C_{MIL}$ represents the concentration of bacteria in suspension following MIL-based extraction and $C_S$ is the concentration of bacteria in the initial sample.

$$E_F = C_{MIL}/C_S \quad (1)$$

Recombinase Polymerase Amplification

RPA TwistAmp Basic and TwistFlow *Salmonella* were purchased from TwistDX (Cambridge, UK). RPA was carried out according to the manufacturer's instructions and results were visualized using either gel electrophoresis (TwistAmp Basic kit) or a chromatographic lateral flow assay (TwistFlow *Salmonella* kit). Using the TwistAmp Basic kit, a 340 bp region of the putative dienelactone hydrolase gene (DLH) was amplified using the following primer set: (Forward primer) 5'-GCC GGG CAG CRA TTA TTC TGC ATG AA-3' (SEQ ID NO: 1) and (Reverse primer) 5'-TGG CGT ATA CGG GAA CCG TAA TAG CA-3' (SEQ ID NO: 2).

The DLH primer set used in this study were both 1) 26 nucleotides in length, 2) contained between 30-50% guanidine content in the first ten nucleotides on the 5'-end, and 3) generated an expected amplicon size of 340 bp. This primer set was previously unpublished and originally intended for PCR detection of *Salmonella enterica* subsp. *enterica* (*Salmonella* subspecies I), which are responsible for the majority of *Salmonella* infections in humans. The primer set targets a putative dienelactone hydrolase protein, generating an expected 340 bp amplicon. Surprisingly, in this study, this primer set yielded stronger amplification results than did other established primers examined, such as the invA primers.

An in silico analysis of this primer set using the Primer-Blast tool (National Center for Biotechnology Information; www.ncbi.nlm.nih.gov/tools/primer-blast/index.cgi) indicated that within the *Salmonella enterica* I database (NCBI taxonomy ID: 59201), the primer set matched several subspecies I serotypes, including the top three disease-causing serotypes identified in the most recent Centers for Disease Control and Prevention (CDC) *Salmonella* Surveillance Report (*S. Enteritidis* (225 hits within the *S. enterica* I database), S. Typhimurium (57 hits), and *S. Newport* (21 hits). Of these three, S. Typhimurium and *S. Newport* have been involved in outbreaks associated with various foods, while *S. Enteritidis* has long been especially problematic in eggs.

Furthermore, because the Primer-Blast software does not accommodate degenerate bases (the DLH primer set contains an "R", which indicates either an "A" or a "G" in this position), it was expected that additional *Salmonella* serovars would be detected with this primer set.

The primer set targeting the invA gene is (Forward primer) 5'-CTA CAA GCA TGA AAT GGC AGA ACA GCG TCG-3' (SEQ ID NO: 3) and (Reverse primer) 5'-CAA CCA GAT AGG TAG GTA ATG GAA TGA CGA-3' (SEQ ID NO: 4).

Figure 3A:
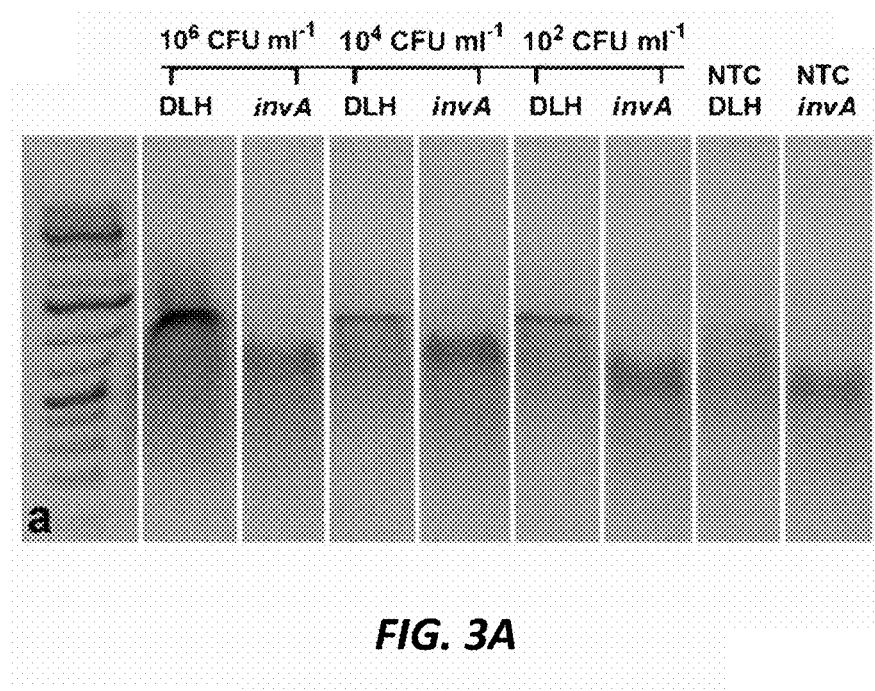
FIG. 3A shows the comparison of DLH and invA primers for detection of MIL-extracted S. Typhimurium using gel electrophoresis.
Figure 3B:
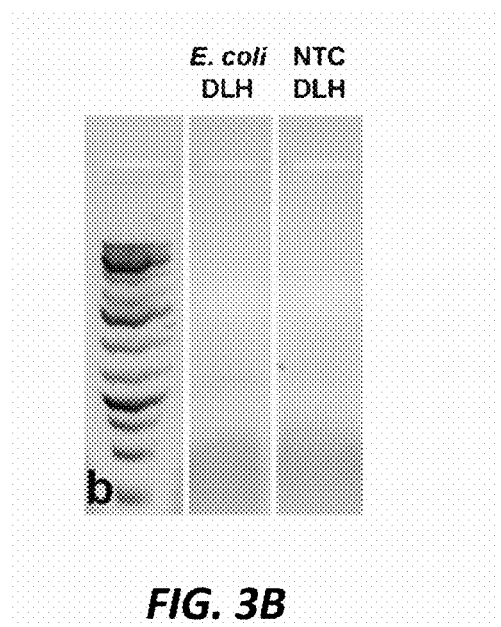
FIG. 3B shows that the evaluation of DLH RPA with MIL-extracted *E. coli* supports in silico results demonstrating the specificity of the DLH primers for *Salmonella* spp.

For both assays, primers were diluted with nuclease free water from a 100 µM stock of mixed primers to a working concentration of 10 µM. Because the DLH primer set resulted in higher amplicon production as indicated in FIG. 3A and FIG. 3B, it was used in subsequent experiments.

For the TwistFlow *Salmonella* kit (also targeting the invA gene), a master mix containing primer in rehydration buffer and nuclease-free water was prepared. Sample DNA was obtained from the MIL back-extraction or using the PMU approach as per manufacturer's instructions. For each kit, master mix, plus 1 µL of sample DNA was added to the lyophilized RPA reagents contained in a PCR tube, where the entire volume was mixed using a pipette. Following this, 2.5 µL of 280 mM magnesium acetate (TwistDX) was added to initiate amplification. Sample tubes were inverted vigorously 10 times, vortexed for 10 s, followed by centrifugation for 5 s to draw the sample to the base of the tube. This mixing process was repeated after 4 min of incubation, and after completion of incubation. For both the TwistAmp Basic and TwistFlow *Salmonella* kits, reactions were incubated using a GeneAmp PCR System 9700 (Applied Biosystems, Foster City, CA, USA) at 40° C. for 20 minutes. S. Typhimurium was tested for each RPA kit, while E. coli served as a negative control.

Gel Electrophoresis

After heating, RPA products generated using the Twist-Amp Basic kit were mixed with 10 µL of 6× bromophenol blue/xylene cyanol FF loading dye (Thermo Fisher Scientific) and loaded on a 1% agarose gel stained with either SYBR Safe DNA Gel Stain (Thermo Fisher Scientific) or GelRed (Biotium, Fremont, CA, USA). Using 1×TBE as the running buffer, samples were subjected to electrophoresis using a Mupid-2Plus Submarine Electrophoresis System (Mupid Co., Ltd., Tokyo, JP), for 35 min at 100 V. Gel bands were visualized using either a Safe Imager 2.0 Blue Light Transilluminator (Thermo Fisher Scientific), or an Azure Biosystems c300 imaging system (Azure Biosystems, Dublin, CA, USA) at 302 nm with a 20 s exposure time.

Lateral Flow Assay

Single-tube amplification products generated using the TwistFlow Salmonella kit were added directly to a nucleic acid lateral flow immunoassay (NALFIA) disposable cartridge (Ustar Biotechnologies (Hangzhou) Ltd., Hangzhou, CN). The NALFIA relies on visual detection of a test band facilitated by the extension of biotin and 6-carboxyfluorescin (6-FAM) labeled primers during RPA. The amplification product is visible by eye as a result of aggregation of streptavidin-conjugated gold nanoparticles, which bind to the biotin-labeled 5' end of the double-stranded amplicon. The terminal 6-FAM group of the amplicon is also selectively captured by the anti-FAM antibody, which is embedded in the test line on the lateral flow strip. A control line consisting of biotin-conjugated BSA exhibits strong affinity for any remaining streptavidin-conjugated gold nanoparticles and can be visualized for a valid assay. Generation of a red band at the test position indicates successful amplification of the double-stranded product, sandwiched between the bound anti-FAM antibody and the streptavidin-conjugated gold nanoparticles. A positive result was recorded if both the control and test bands were identified within 10 min, whereas detection of only the control band indicated a negative result.

Materials and Methods—Examples 7 to 15

Reagents and Magnetic Ionic Liquid Preparation

Figure 7A:
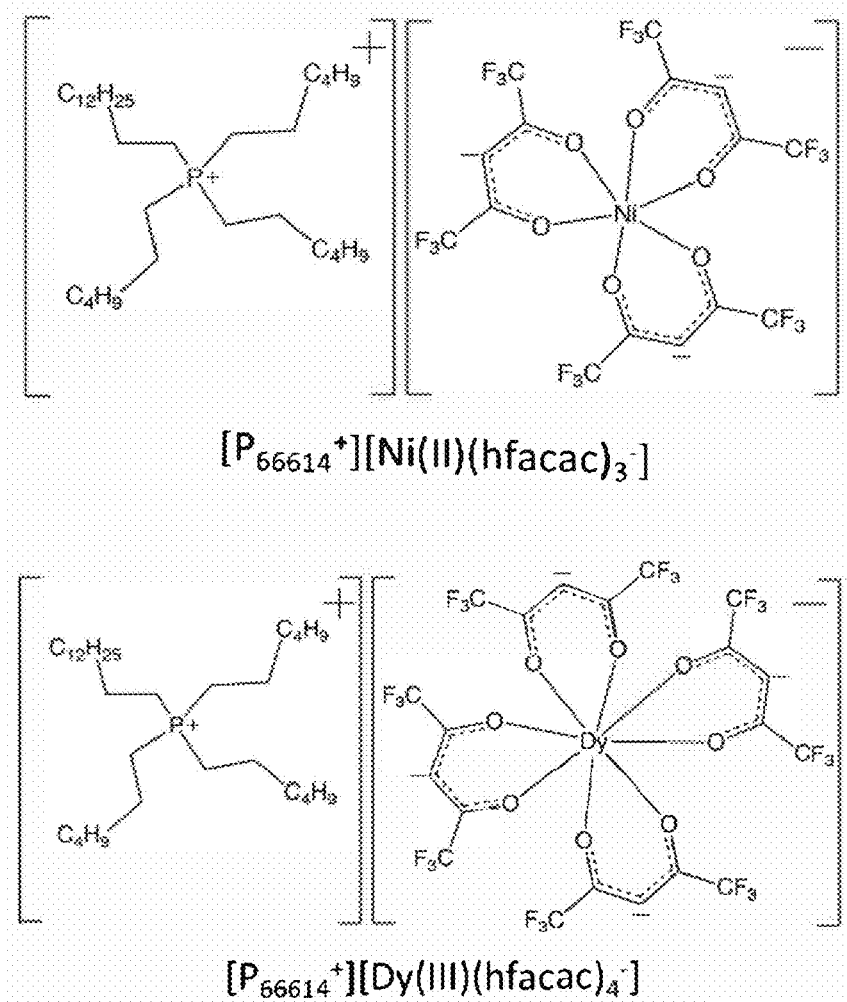
FIG. 7A shows the general structures of some exemplary MILs, including those used in Examples 7-15.

Chemical structures of the two MIL solvents examined in these examples are shown in FIG. 7A. Synthesis and characterization of the MILs was performed as previously described. A brief description of MIL synthesis is also provided below. MIL solvents were purified by liquid-liquid extraction with acetonitrile/hexane and dried in vacuo. Prior to all experiments, MILs were stored in a desiccator for at least 24 h.

The $[P_{6,6,6,14}^+][Ni(II) (hfacac)_3^-]$ $[P_{6,6,6,14}^+][Dy(III) (hfacac)_4^-]$ MILs were synthesized following a previously reported procedure. Briefly, 10 mmol of hexafluoroacetyl acetone was added dropwise into a round bottom flask sealed with a rubber septum containing 10 mmol of ammonium hydroxide in 30 mL of ethanol. After the white vapor formed settled, 3.3 mmol of nickel (II) chloride or 2.5 mmol of dysprosium(III) chloride hexahydrate were added and stirred at room temperature for 5 h. Following evaporation under vacuum, the crude product was dissolved in diethyl ether, filtered, and washed several times with deionized water until no apparent precipitate was observed when a $AgNO_3$ test was performed. Subsequently, diethyl ether was evaporated and the purified salt dried overnight in a vacuum oven at 50° C. The purified salt was dissolved in methanol and an equimolar amount of trihexyl(tetradecyl)phosphonium chloride was added and stirred overnight. The crude MIL product was dissolved in hexane and filtered. The product was subsequently washed with aliquots of water until no precipitate was observed during a $AgNO_3$ test. Hexane was then evaporated and the purified MIL was dried in a vacuum oven overnight at 50° C.

Bacteria and Culture Conditions

All of the bacterial strains used in these examples belong to the family Enterobacteriaceae and are listed in Table 1. All growth media were from Becton, Dickinson and Company (Franklin Lakes, NJ, USA). Cultures of S. marcescens were grown as described above. Salmonella and E. coli were grown 24 h in 10 mL volumes of Tryptic Soy Broth (TSB) at 37° C. K. aerogenes and C. sakazakii were grown in 5 mL volumes of TSB at 30° C. and Y. enterocolitica strains were grown at 37° C., with shaking (190 rpm) on a Shel Lab Shaking incubator (Sheldon Manufacturing, Inc., Cornelius, OR, USA). Plant pathogens were grown in 10 mL volumes of Columbia Broth (CB) at 28° C. with shaking at 190 rpm. Depending on the experiment, bacteria were enumerated using Tryptic Soy Agar (TSA), Columbia Agar (CA), Bismuth Sulfite Agar (BSA) or Violet Red Bile Glucose Agar (VRBGA) plates as described under "Plating and Enumeration".

TABLE 1

| Organism | Source |
| --- | --- |
| Cronobacter sakazakii 01088P (derived from ATCC 29544) | Microbiologics[a] |
| Erwinia amylovora Ea935 | ISU PP[b] |
| Escherichia coli O157:H7 N886-71 | OHA[c] |
| Escherichia coli O157:H7 N366-2-2 | OHA |
| Escherichia coli O157:H7 N549-3-1 | OHA |
| Escherichia coli O157:H7 N317-3-1 | OHA |
| Escherichia coli O157:H7 N192-5-1 | OHA |
| Escherichia coli O157:H7 N192-6-1 | OHA |
| Escherichia coli O157:H7 N336-4-1 | OHA |
| Escherichia coli O157:H7 N405-5-8 | OHA |
| Klebsiella aerogenes ATCC 29940 | ISU PP |
| Pantoea eucalypti 299R (formerly Pantoea agglomerans 299R) | ISU PP |
| Pantoea stewartii Rif9A | ISU PP |
| Pectobacterium carotovorum pv. carotovorum | ISU PP |
| Salmonella bongori SA4410 | SGSC[d] |
| Salmonella enterica subsp. arizonae SA4407 | SGSC |
| Salmonella enterica subsp. diarizonae SA4408 | SGSC |
| Salmonella enterica subsp. enterica ser. Minnesota SLH 157 | SLH[e] |
| Salmonella enterica subsp. enterica ser. Minnesota mR613 | SGSC |
| Salmonella enterica subsp. enterica ser. Typhimurium ATCC 14028 | ATCC[f] |
| Salmonella enterica subsp. houtenae SA4409 | SGSC |
| Salmonella enterica subsp. indica SA4411 | SGSC |
| Salmonella enterica subsp. salamae SA4406 | SGSC |
| Serratia marcescens | CBS[g] |
| Yersinia enterocolitica subsp. enterocolitica ATCC 9160 | ATCC[f] |
| Yersinia enterocolitica subsp. enterocolitica ATCC 23715 | ATCC |

[a]Microbiologics (St. Cloud, MN); ISU PP,
[b]Iowa State University Plant Pathology;
[c]OHA, Oregon Health Authority, Public Health Division (Portland, OR, USA);
[d]SGSC, Salmonella Genetic Stock Centre (Calgary, Alberta, Canada);
[e]SLH, Wisconsin State Laboratory of Hygiene (Madison, WI, USA);
[f]ATCC, American Type Culture Collection (Manassas, VA, USA);
[g]CBS, Carolina Biological Supply (Burlington, NC)

MIL-Based Whole-Cell Extraction

Figure 7B:
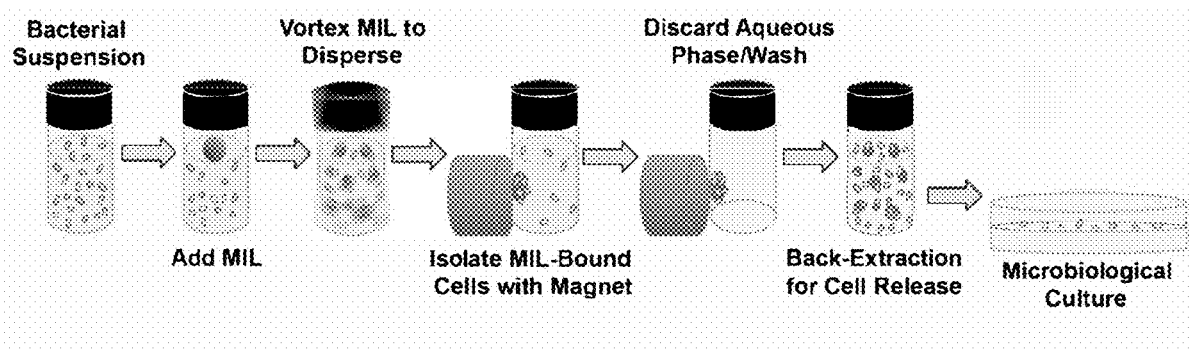
FIG. 7B shows a schematic for the capture, concentration and recovery of enterobacteria from aqueous samples, followed by downstream analysis by microbial culture using non-selective and/or selective media.

A universal schematic for MIL-based cell extraction is depicted in FIG. 7B. A 1 mL volume of diluted cell suspension was added to a flat-bottomed 4-mL screw cap glass vial. Fifteen microliters of either the Ni(II) or Dy(III) MIL was added and dispersed into microdroplets by vortex agitation for 30 s. The aqueous phase was decanted following dispersive extraction, and the MIL was subjected to a brief wash step using 1 mL of nuclease-free water (Integrated DNA Technologies, Coralville, IA, USA) to ensure adequate removal of loosely or incidentally bound cells. After washing, release of viable cells from the MIL extraction phase was carried out using a "back-extraction" step accomplished through addition of 1 mL of an ionically-rich nutritive medium comprised of 20 g $L^{-1}$ tryptone and 10 g $L^{-1}$ NaCl, followed by a 120 s vortex step. After back-extraction, aliquots of the cell-enriched back-extraction medium were enumerated using the track dilution method using 100×100 mm square, gridded TSA, BSA, CA or VRBGA plates.

Plating and Enumeration

Following back-extraction, aliquots of the cell-enriched back-extraction medium were serially diluted in 0.1% peptone water and a 10 μL aliquot of each dilution was applied to a separate lane on square plates containing an appropriate agar medium. The plates were then tilted at an approximately 80° angle for 15 min to allow the droplets to travel toward the opposite end of the plate. The plates were incubated for 24 h at 37° C. (TSA, VRBGA), for 48 h at 37° C. (BSA) or for 24 h at 37° C. (CA). Colonies were counted and colony forming units (CFU) were determined. The enrichment factor ($E_F$) for MIL-based extraction was calculated using Equation 1, where $C_{MIL}$ represents the concentration of bacteria in suspension following extraction using the MIL and $C_S$ is the initial concentration of bacteria in the sample.

$$E_F = \frac{C_{MIL}}{C_S} \quad (1)$$

Exposure to Ni(II) MIL as a Function of Time and Evaluation of [EMIM$^+$][SCN$^-$] IL Toxicity To examine whether exposure time to the Ni(II) MIL affected cell viability, MIL-based whole-cell extraction was performed using the Ni(II) MIL, and cell-enriched back-extraction media were enumerated at 0, 5, 10 and 15 min on both TSA and BSA. To evaluate toxicity of the [EMIM$^+$][SCN$^-$] IL, one milliliter of diluted S. Typhimurium ATCC 14028 cell suspension was added to a 4-mL screw cap glass vial. A 5% (vol/vol) or 50% (vol/vol) aqueous solution of 1-ethyl-3-methylimidazolium thiocyanate ("[EMIM$^+$][SCN$^-$]") (IoLiTec, Tuscaloosa, AL, USA) was added and mixed by vortexing for 30 s. Aliquots were enumerated at 0, 5, 10 and 15 min using TSA and BSA.

Comparison of Air-Displacement and Positive Displacement Pipettes for MIL Handling A 1 mL volume of diluted S. Typhimurium ATCC 14028 cell suspension was added to a 4-mL screw cap glass vial. Fifteen microliters of the Ni(II) MIL was added using either a Pipetman Classic P20 air-displacement pipette (Gilson, Middleton, WI, USA), or a Microman E M25E positive-displacement pipette (Gilson) and dispersed into microdroplets by vortex agitation for 30 s. MIL-based extraction and enumeration was carried out as previously described.

Exposure to Dy(III) MIL, DyCl$_3$ and ([NH$_4^+$][Dy(hfacac)$_4^-$])

One milliliter of diluted S. Typhimurium ATCC 14028 cell suspension was added to a 4-mL screw cap glass vial. Fifteen microliters of either the Dy(III) MIL or 2-10 μL of 100 mM DyCl$_3$ solution or 10 mg of the ammonium tetra(hexafluoroaceto)dysprosium salt (15) ([NH$_4^-$][Dy(hfacac)$_4^-$]) ("Dy(III) ammonium salt") was added and dispersed by vortex agitation for 30 s. Aliquots of the Dy(III) MIL- or Dy(III) ammonium salt-exposed cell suspension were enumerated using square TSA or BSA plates (BD).

Impact of Ionic Environment on Ni(II) MIL Dispersion Properties and Bacteria-MIL Interactions by Flow Imaging Microscopy For analysis of MIL dispersion properties as a function of ionic environment, microdroplet suspensions of the Ni(II) MIL were generated as above for whole-cell extraction of bacteria and analyzed with a FlowCam 8000 instrument (Fluid Imaging Technologies, Inc., Scarborough, ME). Briefly, three peptone water (PW) formulations representing multiples of the manufacturer's basal formulation for this medium were added to 4-mL screw cap glass vials. Fifteen microliters of the Ni(II) MIL were added to each PW formulation and the mixture dispersed with vortexing for 30 s for microdroplet formation. Samples were analyzed immediately using the FlowCam instrument using the 10× objective (100 μm field of view). Samples (20 μL) were taken from the top portion of each tube with a ~25 s collection time. PW formulations evaluated were 1× (0.5% NaCl/1% peptone), 5× (2.5% NaCl/5% peptone) and 10× (5% NaCl/10% peptone). Data were analyzed with VISUALSPREADSHEET® software (v. 5.0, Fluid Imaging Technologies, Inc.). A basic size filter of 5 μm (minimum droplet size) to 10,000 μm (maximum droplet size) was applied, and droplet distributions were plotted as volume (%) vs. equivalent spherical diameter (ESD). Key measurements tabulated for each ionic condition include mean droplet diameter (ESD), maximum droplet size, $D_{50}$ (median droplet size; 50% are smaller and 50% are larger than this value), $D_{90}$ (90% of droplets are smaller than this value) and number of droplets mL$^{-1}$. The same settings were used for analysis of bacteria-MIL interactions, with high concentrations (~$10^7$-$10^8$ CFU mL$^{-1}$) of S. marcescens suspended in 1× PW prior to addition of the MIL and sampling.

Statistical Analysis

The following statistical analysis was performed in SAS 9.4. Four master suspensions of bacteria were prepared for four Salmonella enterica serovars: subsp. Typhimurium, subsp. arizonae, subsp. diarizonae and subsp. houtenae. Two master suspensions were made for the remaining three Salmonella serovars or species: S. enterica subsp. indica, subsp. salamae and S. bongori. For E. coli O157:H7, two master suspensions of bacteria were prepared for each of the eight strains studied. For all bacteria tested, two replicate extractions from the same master suspension were performed, using the $10^{-3}$ dilution. Following MIL-based capture, back-extraction solutions were plated to non-selective agar (TSA) and selective agar (BSA) for Salmonella and SMAC for E. coli. To identify whether significant differences existed for the capture of Salmonella and E. coli O157:H7, we applied a linear mixed model for the response variable (enrichment factor) with log transformation in order to reduce skewness. We treat both the strain and the medium as fixed effects and the suspension of bacteria as the random block.

In order to compare potential injury caused by the MIL across genera (Salmonella serovars and STEC Escherichia), a medium suitable for growth of both organisms (VRBGA) was used in parallel with TSA and resulting counts were compared in experimental settings repeated across five different days. In each experiment, three Salmonella serovars were tested: S. Typhimurium ATCC 14028, S. Minnesota SLH 157, and deep rough mutant S. Minnesota mR613. Two E. coli strains were also tested: E. coli O157:H7 N192-6-1 and E. coli O157:H7 N192-5-1. We applied the linear mixed model for the log-transformed enrichment factors with fixed strain and agar effects and random blocks of the experiment days as samples from a population of days.

Example 1

Optimization of MIL Extraction Conditions for a Model Gram-Negative Bacteria

In this Example, the non-pathogenic *Serratia marcescens* was used as a model gram-negative bacterium for optimizing capturing and concentrating bacteria. *S. marcescens* is a gram-negative bacterium in the same family as *Salmonella*. It produces a reddish-orange pigment known as prodigiosin. This property facilitates unambiguous visual detection of *S. marcescens* and make it a good model gram-negative bacterium in development of pre-analytical sample preparation methods.

Since the chemical structure of the MIL has profound implications on its extraction behavior, three exemplary MILs (Ni(II), Co(II) and Dy(III)) were chosen for their bacterial extraction.

FIG. 1A shows the general structures of some exemplary MILs, including those used in this Example. FIG. 1B shows the schematic for the extraction and preconcentration of *Salmonella* Typhimurium from aqueous food samples, followed by downstream analysis using RPA amplification and microbiological culture detection methods. In some experiments, the cell-enriched MIL microdroplets were collected as a function of MIL density (~1.3 g/mL for the Ni(II) MIL), in others, a magnet was used.

In this Example, the capturing step was done by vigorously dispersing a small volume of MIL (e.g., 15 µL) in an aqueous suspension of *S. marcescens* ($1 \times 10^3$ CFU/mL). After the bacteria cells were extracted into the resulting MIL microdroplets, the cell-enriched microdroplets were harvested based on either MIL density (~1.3 g/mL for the Ni(II) MIL) or through manipulation with an external magnetic field as shown in FIG. 1B.

After the cell-enriched MIL was rinsed with deionized water, the bacteria cells were recovered from the MILs using Luria-Bertani nutrient broth (LB, per L: 10 g tryptone, 5 g yeast extract, 10 g NaCl) or other medium compositions, plated, and incubated at 25° C. for 48 hours prior to enumeration.

To maximize the recovery of viable bacteria from the MIL extraction phase, several LB-based back-extraction media varying in ionic strength and nutrient composition were investigated for its effect, using Co(II) MIL as the extracting MIL.

For these experiments, suspensions of *S. marcescens* ($1 \times 10^3$ CFU/mL, in 1 mL 0.1% peptone) were vortexed for 30 seconds with 15 µL of the Co(II) MIL, then resuspended for a 2 min back-extraction into 1 mL of either water (control), LB medium or 7 variations of the basic LB medium recipe.

Figure 2:
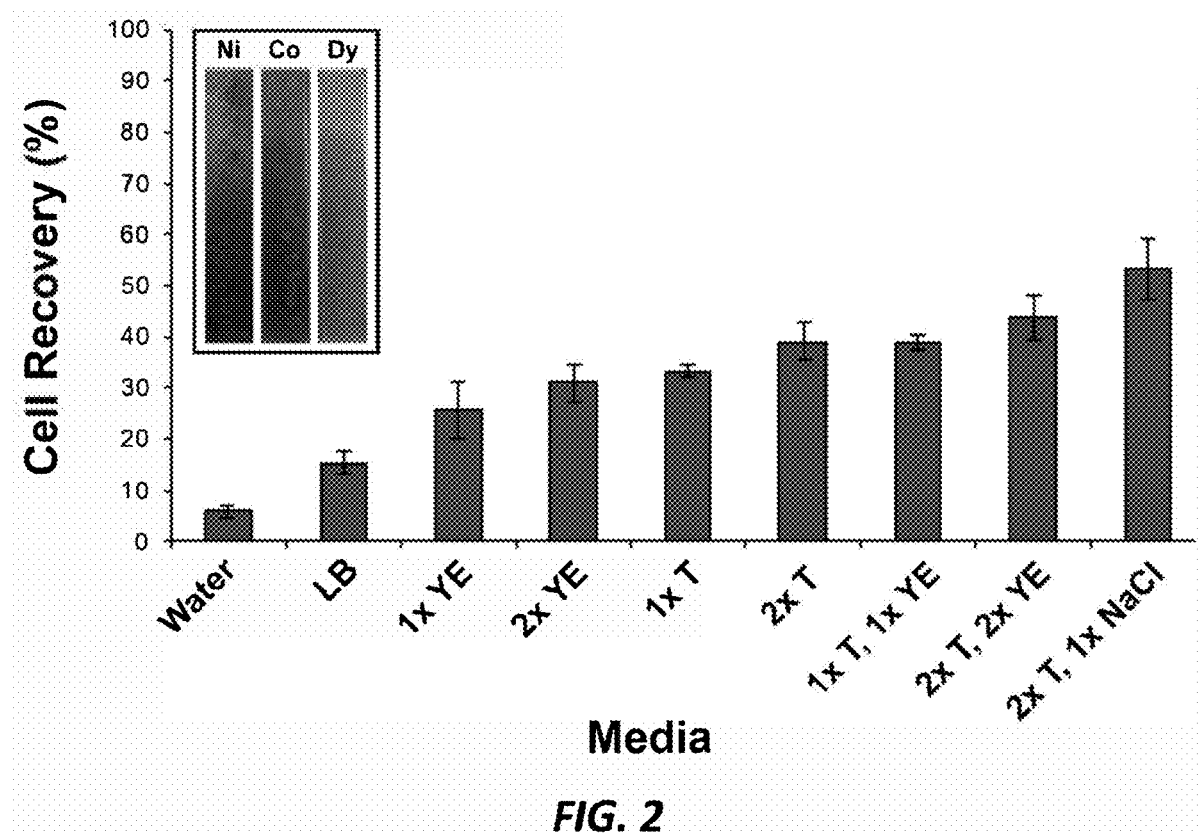
FIG. 2 shows the recovery of S. marcescens extracted with Co(II) MIL as a function of back-extraction medium composition.

FIG. 2 shows the recovery of *S. marcescens* extracted with Co(II) MIL as a function of back-extraction medium composition. In FIG. 2, the percentages of initial cell load recovered from the Co(II) MIL extractant using aqueous back-extraction media of different ionic composition were shown. The back-extraction media were water (control), LB medium, and 7 variations of the basic LB medium with different ionic compositions, which were 1×YE (5 g/L yeast extract); 2×YE (10 g/L yeast extract); 1×T (10 g/L tryptone); 2×T (20 g/L tryptone); 1×T, 1×YE (10 g/L tryptone, 5 g/L yeast extract); 2×T, 2×YE (20 g/L tryptone, 10 g/L yeast extract); 2×T, 1×NaCl (20 g/L tryptone, 10 g/L NaCl). Average cell recoveries and error from 3 replicate experiments were also shown in FIG. 2. The inset in FIG. 2 shows the representative cell growth on track plates obtained following the extraction of *S. marcescens* using Ni(II), Co(II), and Dy(III) MILs, respectively.

As shown in FIG. 2, back-extraction using deionized water resulted in the lowest quantity of bacteria cells recovered from the MIL while the greatest quantity of cells was obtained with a nutrient-rich tryptone medium supplemented with NaCl (2×T, 1×NaCl).

Back-extracted samples were then diluted 100-fold prior to plating to ensure that countable dilutions within the statistically valid range of 25-250 CFU were obtained. The results showed that *S. marcescens* cells were physically enriched by the MIL to levels between 5 and 6 times higher than their initial concentration. As a result of this Example, it can be concluded that the hydrophobic MIL solvent imposes stress on the cell in the extraction process, that a supportive nutrient media helps the stressed cell to recover, and that the 2×T, 1×NaCl back-extraction medium provided the highest recoveries for *S. marcescens*.

Example 2

MIL Extraction Conditions for S. Typhimurium Bacteria

In this Example, extraction and preconcentration of S. Typhimurium by the exemplary MILs were investigated using the 2×T, 1×NaCl back-extraction medium. The results showed that as with *S. marcescens*, similar recoveries of viable *Salmonella* were observed for both Ni(II) and Co(II) MILs, resulting in enrichment factors of approximately 12, which was comparable to previous enrichment factors for the MIL-based extraction of *E. coli*. The results in the Example demonstrated that using MIL and proper back-extraction medium, it was possible to preconcentrate viable pathogenic *S. marcescens* bacteria from aqueous suspensions.

Because Ni(II) and Co(II) MILs showed results were similar, subsequent experiments toward coupling MIL-based bacterial extraction with molecular detection using RPA were performed using the [P66614+] [Ni(hfacac)$_3^-$] MIL.

Example 3

Combining MIL-Based Extraction with *Salmonella*-Targeted RPA

Because nucleic acid amplification techniques can dramatically decrease analysis times and increase sample throughput, they are becoming increasingly popular alternatives to culture-based methods, especially for sample screening purposes.

In this Example, the feasibility of coupling the MIL-based method for capturing and concentrating S. Typhimurium from aqueous media with the speed and simplicity of RPA analysis were investigated.

Here, after preconcentration and recovery of S. Typhimurium from an aqueous sample using the Ni(II) MIL, the back-extraction suspension was heated for 10 min at 100° C. to lyse the bacteria and release their nucleic acids for downstream RPA analysis.

First, two primer sets for the amplification of nucleic acids from S. Typhimurium: primers targeting the invA gene (invA primer) and primers identified via comparative genomic analysis and amplifying a 340 bp region of a putative dienelactone hydrolase gene (DLH primer), were compared.

FIG. 3A shows the comparison of DLH and invA primers for detection of MIL-extracted S. Typhimurium using gel electrophoresis. Suspensions of *Salmonella* Typhimurium in aqueous media at three different levels ($10^6$, $10^4$, and $10^2$ CFU/mL) were extracted and recovered using the Ni(II) MIL and the medium, subjected to a 20 min RPA using the DLH and invA primers and examined on an agarose gel stained with SYBR Safe DNA Gel Stain. FIG. 3A shows that the bands for DLH primers consistently showed higher fluorescence (greater product yield) across all cell concentrations used.

In order to demonstrate the selectivity of the DLH-targeted RPA primers for *Salmonella*, an aqueous suspension of *E. coli* ATCC 25922 prepared at a concentration of $10^5$ CFU/mL was extracted using the Ni(II) MIL and subjected to RPA analysis following recovery and lysis.

FIG. 3B shows that the evaluation of DLH RPA with MIL-extracted *E. coli* supports in silico results demonstrating the specificity of the DLH primers for *Salmonella* spp. An amplicon was not detected for the *E. coli* sample, indicating good selectivity of the DLH primers for *Salmonella*.

Example 4

Evaluating Use of a Power-Free Heat Source for *Salmonella*-Targeted RPA

A major limitation of many nucleic acid amplification methodologies is their reliance on electricity to power a heat source such as a thermal cycler in PCR or a heat block for isothermal methods. To circumvent this limitation, using super-saturated sodium acetate heat packs—a small, portable consumer-grade novelty product used in handwarmers and earmuffs (Cristalheat, xUmp.com)—as a power-free means for driving RPA were investigated in this Example.

First, the internal temperature of a template-free RPA reaction tube sandwiched between two activated heat packs using an OPTOCON FOTEMP1-4 fiber optic temperature monitoring system (Optocon AG, Dresden, Germany) was measured. Data were collected using the FOTEMP Assistant software, exported to Microsoft Excel and plotted in Prism graphing software (Prism 7 for Mac OS X, v. 7.0d, Graphpad Software, La Jolla, CA).

Figure 4:
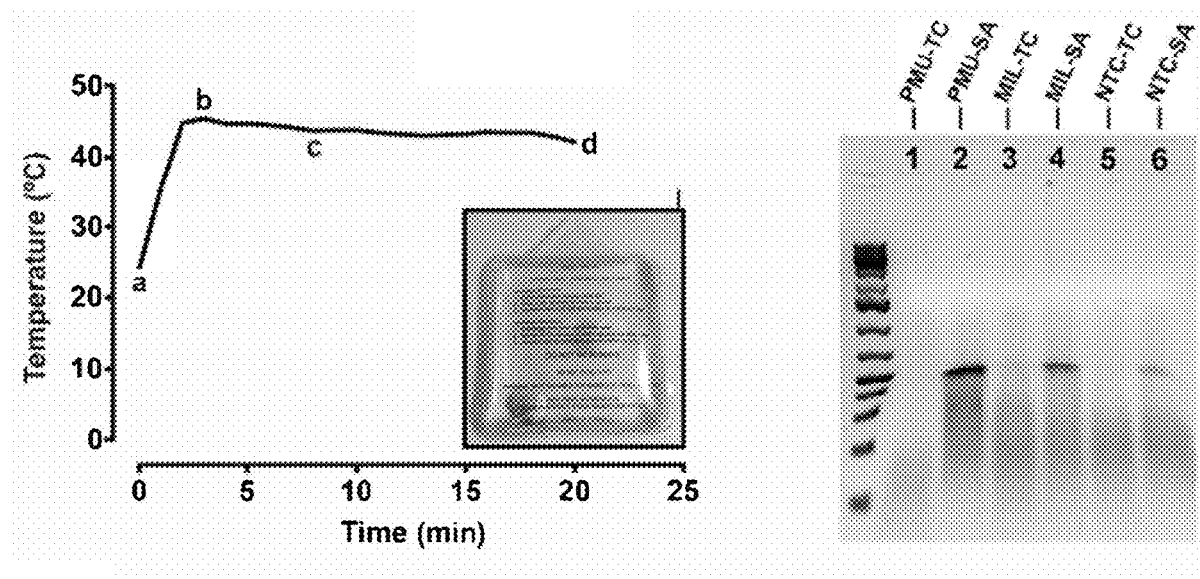
FIG. 4 shows the evaluation of sodium acetate heat pack for power-free incubation of RPA reactions.

FIG. 4 shows the evaluation of sodium acetate heat pack for power-free incubation of RPA reactions. The results as shown in FIG. 4 indicate that sodium acetate heat packs were able to provide near-optimal RPA reaction temperatures (reported range, 37° C.-42° C.) over typical amplification times. Temperatures at various points along the time-temperature curve are 25.2° C. (initial temperature, point a), 45.4° C. (point b), 43.7° C. (point c), and 42.1° C. (point d). Temperatures remained within the optimal RPA reaction range for up to 40 minutes. FIG. 4 also shows the comparison of DLH-RPA reactions driven with a thermal cycler (TC) or with sodium acetate heat packs (SA). Bacterial DNA was obtained using the PrepMan Ultra Sample Preparation Reagent (PMU) or via MIL-based extraction (MIL).

As shown in FIG. 4, the temperature of the RPA mixture increased rapidly after heat pack activation, reached equilibrium between 42° C. and 44° C. and remained within optimal RPA temperature range for up to 40 min.

Next, the performance of heat pack-driven RPA using the DLH primer set and MIL-extracted S. Typhimurium was tested. Intense amplicon bands were seen for sodium acetate-driven DLH-RPA with DNA isolated using either the PrepMan Ultra Sample Preparation Reagent (PMU-SA) or with MIL-extracted cells (MIL-SA) as shown in FIG. 4. Although a band was seen with the sodium acetate-heated no-template control (NTC-SA), it is expected that use of lateral flow-based detection would enable differentiation of legitimate amplicons from spurious NTC bands sometimes seen on agarose gels with RPA. The results highlight the utility of sodium acetate heat packs as a viable, power-free means for amplifying nucleic acids from microbial pathogens using RPA.

Example 5

Comparison of Methods for Amplicon Detection, Further Optimization of MIL Approach All elements of a detection assay (cell capture, release of nucleic acids, amplification of target DNA, and product detection) may impact the quality of the result. In this Example, different methods for nucleic acid release in conjunction with further optimization of the MIL-based workflow (larger sample vial size, smaller back-extraction volume) and two approaches for amplicon detection (gel electrophoresis, nucleic acid lateral flow immunoassay [NALFIA]) were valuated.

For direct comparison of methods for release of nucleic acids prior to RPA, heating of the cell-enriched MIL to 100° C. (with modifications, as described below) with use of a commercial approach using PMU was compared. For both approaches, aqueous samples were inoculated with S. Typhimurium at concentrations ranging from $10^3$ to $10^6$ CFU/mL and DLH-targeted RPA was used.

The PMU method was used according to the manufacturer's instructions. Briefly, cells from a liquid suspension were lysed in 200 µL of PMU reagent, followed by heating (15 min, 100° C.), then a lengthy centrifugation step to separate cellular debris from the DNA-containing supernatant.

MIL-based extraction was compared with concurrent extraction using PrepMan Ultra Sample Preparation Reagent (PMU).

Figure 5:
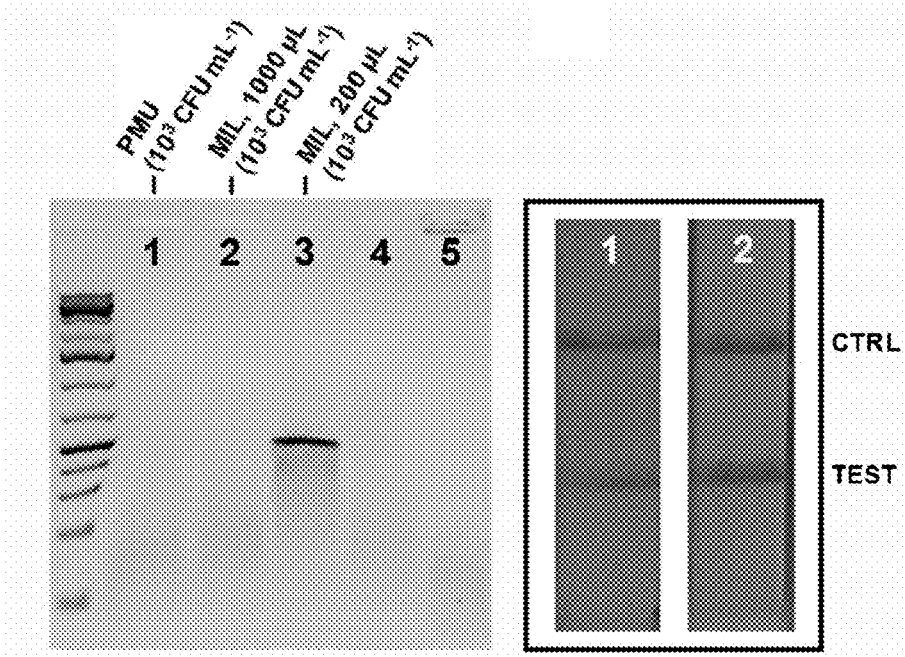
FIG. 5 shows the extraction of *Salmonella* Typhimurium using one of three MILs. The results from the combined MIL and RPA approach were visualized using gel electrophoresis (35 min) or lateral flow (10 min).

FIG. 5 shows the extraction of *Salmonella* Typhimurium using one of three MILs. The results from the combined MIL and RPA approach were visualized using gel electrophoresis (35 min) or lateral flow (10 min). For gel electrophoresis (FIG. 5, left hand panel), PMU limit of detection (LOD) was consistently identified as $10^4$ CFU/mL, however, bands were inconsistently present at lower levels, and were less defined (FIG. 5, lane 1) than detection using MILs at the same level (FIG. 5, lane 3). Using gel electrophoresis, at lower concentrations of S. Typhimurium, the MIL-based extraction outperformed PMU.

Based on the observations of liquid behavior during vortexing process during MIL extraction, it was found that decreasing the sample vial size from 4 mL to 2 mL and decreasing the back-extraction volume from 1 mL to 200 µL could lower the detection limit of the MIL approach to $10^3$ CFU/mL, presumably due to enhanced contact between the MIL and back extraction solution when a smaller sample vial was used and the increased concentration of bacteria in the smaller back-extraction volume as indicated in FIG. 5, gel image, lane 3. These slight modifications improved the sensitivity of the streamlined "capture, concentrate, heat, and amplify" MIL-RPA process, without the addition of further assay elements.

FIG. 5 also shows using a smaller amount (200 μL) of recovery medium during MIL-based extraction resulted in better amplification and visualization of DNA (FIG. 5, lane 3), than compared with the conventional 1000 μL volume (FIG. 5, lane 2). FIG. 5, lanes 4, 5 represent no template controls (NTC). Without these process modifications, the detection limit for the MIL-RPA approach was $10^4$ CFU mL/1 for gel electrophoresis-based visualization of *Salmonella* DLH amplicons.

As indicated in FIG. 5, right panel, using lateral flow, detection was achieved as low as $10^4$ CFU/mL for PMU (strip 1), while limit of detection (LOD) using MILs was $10^4$ CFU/mL (strip 2). By this approach, PMU outperformed the MILs.

PMU was not evaluated for lysis of MIL-captured cells, as this would have introduced additional assay elements, namely use of a chemical lysis reagent and a centrifugation step.

Because conventional gel electrophoresis step is inherently laboratory-bound and adds time to get result, a rapid and portable alternative method for amplicon detection was evaluated. On the other hand, due to its simplicity and portability, nucleic acid lateral flow immunoassay (NALFIA) is often used in resource-limited environments or in non-laboratory settings, as it does not require electricity or laboratory equipment.

For evaluation of NALFIA, the Ni(II) MIL was used for optimized preconcentration and extraction of aqueous samples of S. Typhimurium at concentrations ranging from $10^3$ to $10^6$ CFU/mL and RPA was carried out using a prepared TwistFlow *Salmonella* kit from TwistDX. Visualization of the amplified product was achieved using a 5 min NALFIA step. Initially, this combined MIL-RPA-NALFIA approach facilitated detection at levels as low as $10^5$ CFU/mL.

Since the detection limits using NALFIA were 2 log higher than with gel electrophoresis, any effect of the metal ions released from the hydrophobic MIL phase (e.g., $Ni^{2+}$) during back-extraction on the outcome of the NALFIA step was investigated. For this purpose, PMU samples were spiked with levels of $NiCl_2$ ranging from 0.2 mM to 2 mM. Visible control and test bands were observed for all $NiCl_2$ samples, indicating that the $Ni^{2+}$ concentration present in the MIL back-extraction solution did not inhibit the NALFIA. However, it is conceivable that the lateral flow signal from lower DNA concentrations may be affected by the $Ni^{2+}$ ions.

It is important to note that the NALFIA targets the invA gene, using primers and conditions developed by the manufacturer. Our choice of the dienelactone hydrolase gene target for the gel electrophoresis experiments may also have contributed to differences in observed detection limits due to differences in amplification efficiency between the two primer sets. In order to improve detection limits, the back-extraction volume was decreased to 200 μL, resulting in detection limits for S. Typhimurium as low as $10^3$ CFU/mL with the Ni(II) MIL as indicated in FIG. 5. While the PMU method provided detection of *Salmonella* at levels as low as $10^4$ CFU/mL, PMU requires the use of a benchtop centrifuge that is incompatible with pathogen analysis in the field or in resource limited settings.

Example 6

Rapid Detection of *Salmonella* Using RPA in Liquid Food Samples

To examine the application of the combined MIL-RPA method in a practical setting, it was applied for the detection of S. Typhimurium in food samples including milk (2% milk fat) and almond milk. S. Typhimurium cells were inoculated into 1 mL samples at $10^5$ CFU/mL and extracted using the Ni(II) MIL under optimized conditions. The combined approach enabled detection of S. Typhimurium at $10^5$ CFU/mL as shown in FIG. 6A-FIG. 6C.

In this Example, the combined MIL and RPA approach was applied to almond milk, milk (2% milk fat), 50:50 dilution of milk (2% milk fat:0.1% peptone water), and liquid egg product, respectively. Results were visualized using gel electrophoresis (35 min) or lateral flow (10 min). MIL-based extraction was compared with concurrent extraction using PrepMan Ultra Sample Preparation Reagent (PMU).

Figure 6A:
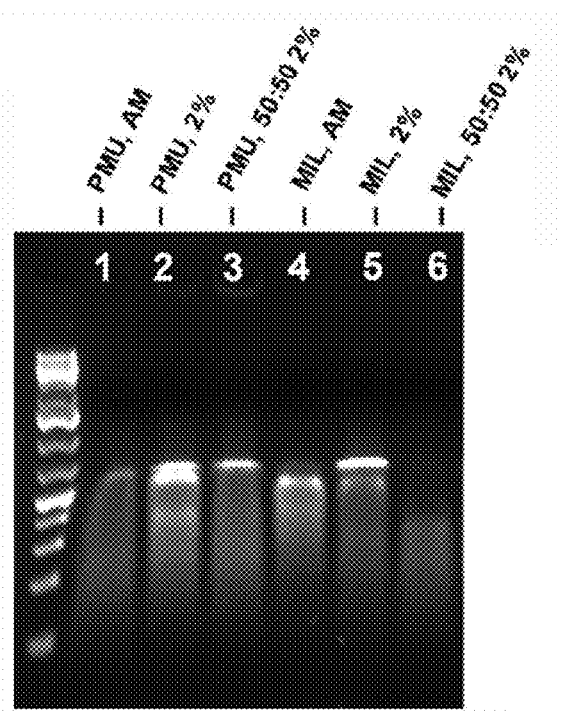
FIG. 6A-FIG. 6C show RPA-based detection of *Salmonella* Typhimurium in various liquid food products or samples.
Figure 6B:
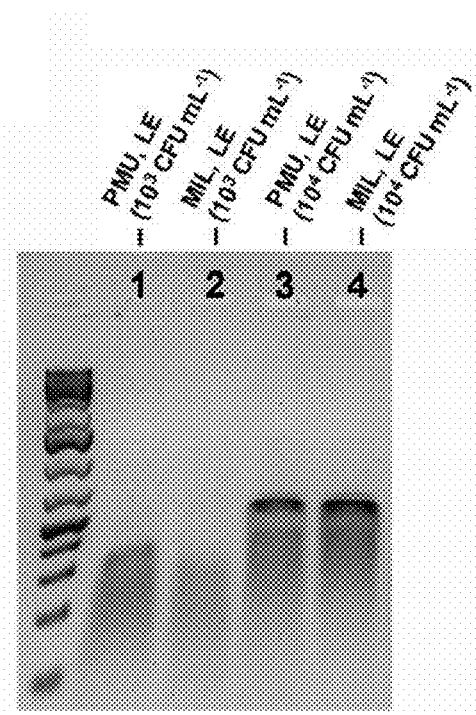
Figure 6C:
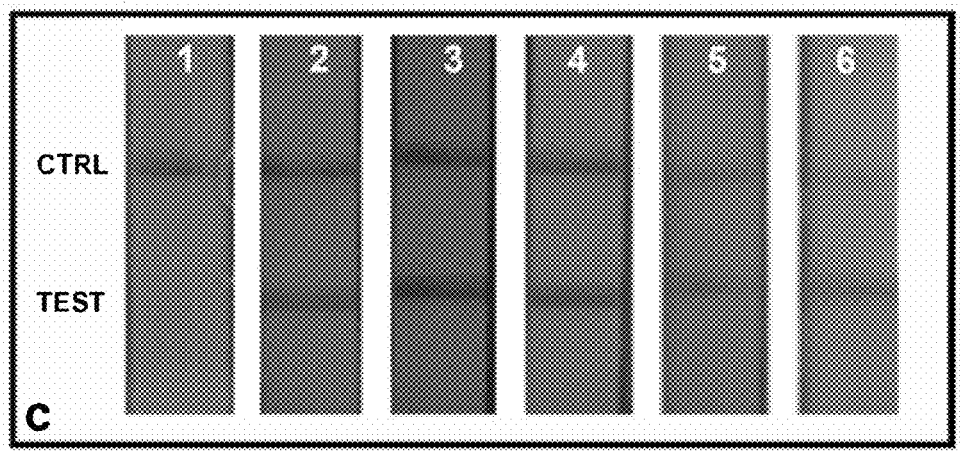

FIG. 6A-FIG. 6C show RPA-based detection of *Salmonella* Typhimurium in various liquid food products or samples. FIG. 6A shows the results for almond milk (lanes 1, 4), milk (2% milk fat) (lanes 2, 5), and 50:50 milk dilution samples (lanes 3, 6) spiked with S. Typhimurium, using gel electrophoresis and either extraction method (PMU or MIL). As shown in FIG. 6A, the detection was achieved at $10^5$ CFU/mL, with the most intense bands observed for the milk (2% milk fat) samples extracted using either the PMU or MIL approach (lanes 2, 5). FIG. 6B shows the results for the liquid egg samples spiked with S. Typhimurium. PMU and MIL LOD was identified as $10^4$ CFU/ml (lanes 3, 4); for both extraction methods, detection was not achieved at $10^3$ CFU/mL (lanes 1, 2). FIG. 6C shows the results using lateral flow as detection method. For the liquid egg samples spiked with S. Typhimurium, LOD was identified $10^4$ CFU/mL for both PMU (lanes 3 and 4) and MIL-extracted samples (lanes 5 and 6); lanes 1 and 2 represents the no template control (NTC) and internal control, respectively.

PMU method did not consistently detect S. Typhimurium in the spiked 2% milk samples, likely due to interference from the ubiquitous fats and lipids in the sample. Because *Salmonella* spp. have been especially problematic in eggs, with large outbreaks occurring in 2010 (almost a half a billion eggs recalled) and 2018 (almost 207 million eggs recalled), the MIL-based preconcentration method was applied to liquid egg samples spiked with concentrations of S. Typhimurium ranging from $10^3$ to $10^5$ CFU/mL.

The foamy nature of the liquid egg sample initially caused challenges in recovering a sufficient volume of MIL for downstream detection bacteria. However, prolonged exposure of the sample (approximately 1 min) to a 0.66 T rod magnet to the base of the 2 mL glass vial facilitated collection of the cell-enriched MIL solvent and enabled detection limits as low as $10^4$ CFU/mL as shown in FIG. 6B.

The commercial PMU method was concurrently compared to the MIL-based approach and exhibited an identical detection limit using RPA and gel electrophoresis. However, the PMU method resulted in less intense bands than those from the MIL-based extraction method as shown in FIG. 6B.

The Ni(II) MIL was also applied for preconcentration of S. Typhimurium in liquid egg samples coupled to RPA and a downstream NALFIA step. Using the combined MIL-RPA-NALFIA approach facilitated detection at levels as low as $10^4$ CFU/mL in inoculated liquid egg samples as shown in FIG. 6C. Once again, this method was concurrently compared with the use of PMU, which maintained similar detection levels but required a laboratory-bound centrifuge that is not compatible with field sampling or on-site analysis.

Example 7

Figure 8:
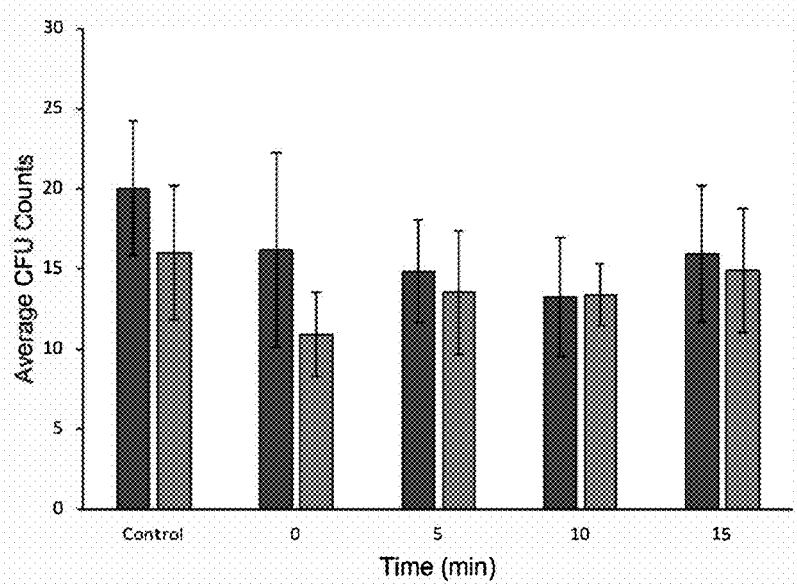
FIG. 8 shows recovery of *Salmonella* Typhimurium extracted with Ni(II) MIL as a function of time (min). Average colony forming unit (CFU) counts recovered from the aqueous Ni(II) MIL back-extraction phase over time (0-15 min). A suspension of S. Typhimurium ATCC 14028 was prepared and captured with the Ni(II) MIL as described in the text, back-extracted using modified LB broth containing 20 g L$^{-1}$ tryptone and 10 g L$^{-1}$ NaCl, then plated on TSA (dark bars) and BSA (light bars). Also shown are results for a standard not treated with the MIL (Control).

Exposure to Ni(II) MIL as a Function of Time and Evaluation of [EMIM$^+$][SCN$^-$] IL Toxicity Because culture-based methods depend on sample preparation steps that preserve bacterial viability, potential deleterious cytotoxic effects imparted by MIL extractants must be considered. To begin our further study of MIL-bacterial interactions, we selected S. Typhimurium ATCC 14028 as a model gram-negative pathogen and the Ni(II) MIL as extractant. Briefly, a 1 mL aliquot of TSB was inoculated with 1×10$^5$ CFU mL$^{-1}$ of bacteria and spiked with 15 µL of the Ni(II) MIL, and the general schematic for MIL-based extraction and recovery followed as shown in FIG. 7B. After extraction, 10 µL aliquots of the back-extraction solution were enumerated at 0, 5, 10 and 15 min using TSA and BSA. Average CFU counts were compared to a standard that was not exposed to the Ni(II) MIL. As shown in FIG. 8, average CFU counts for S. Typhimurium exposed to the Ni(II)-based MIL appeared to be similar on both TSA and BSA for exposure periods ranging from 0 to 15 min. To better understand the data in FIG. 8, statistical analyses of Ni(II) MIL capture precision and CFU count variation as a function of MIL exposure time were performed. Variation in MIL capture may stem from inherent randomness of MIL dispersion and coalescence behaviors.

Enrichment factors were calculated as a function of time. Table 2 shows enrichment factors for S. Typhimurium as a function of exposure time to the Ni(II) MIL. For TSA, the resulting average $E_F$ value was 7.2±0.6 (n=4); for BSA, the average $E_F$ value was 8.2±1.0 (n=4).

TABLE 2

| Time (min) | Enrichment Factor (TSA) | Enrichment Factor (BSA) |
|---|---|---|
| 0 | 8 | 7 |
| 5 | 7 | 8 |
| 10 | 6 | 8 |
| 15 | 8 | 9 |

The effects of 5% or 50% (vol/vol) aqueous solutions of the [EMIM$^+$][SCN$^-$] IL on the viability of the cells were also evaluated. Average CFU counts were compared to a standard not exposed to [EMIM$^+$][SCN$^-$]. In our hands, when S. Typhimurium was exposed to 50% (vol/vol) solutions of [EMIM$^+$][SCN$^-$], no recovery was observed on either TSA or BSA after 5 min of exposure.

Cell injury can be detected by plating MIL-treated cells in parallel on both non-selective and selective media and evaluating growth under each condition. Gram-negative cells possess an outer membrane (OM), which protects them against the diffusion of otherwise toxic molecules into the cell. As a result, physiologically intact gram-negative cells are able to tolerate exposure to toxic agents such as bile salts, crystal violet or brilliant green used in selective agars designed to limit the growth of gram-positive cells. Injury to gram-negative cells caused by exposure to deleterious physical or chemical conditions is typically characterized by damage to the OM, which causes these cells to become "leaky" and show impaired growth on selective agars. Injury can therefore be detected by plating treated cells in parallel on both non-selective and selective agars and comparing the results. When we exposed suspensions of S. Typhimurium to the Ni(II) MIL for times ranging from 0 min (essentially our standard 30 s extraction protocol) to 15 min, the resulting average CFU counts on TSA and BSA appeared similar, regardless of exposure time.

The [EMIM$^+$] [SCN$^-$] IL has been previously investigated for solubilization of protein-rich food matrices as a means for sample preparation. The [EMIM$^+$] cation potentially acts as a detergent, while the [SCN$^-$] anion is chaotropic. The ability to essentially obliterate difficult food matrices with this IL, then collect released bacterial cells for analysis represents a novel advance in sample preparation. However, [EMIM$^+$] [SCN$^-$] was reported to be injurious to Salmonella Typhimurium in this application, with only 34-45% of inoculated S. Typhimurium recovered after IL-mediated matrix lysis when plated to a selective agar. In our hands, when S. Typhimurium was exposed to [EMIM$^+$][SCN$^-$] as originally described for IL-based extraction of this pathogen from foods, no recovery was observed on either TSA or BSA, confirming the injurious nature of this IL in stark contrast to and in direct comparison with our "cell-friendly" Ni(II) MIL.

It is possible that a major contributor to the innocuous behavior of our Ni(II) MIL with gram-negative bacteria stems from the inherent capacity of the OM to exclude hydrophobic compounds—which the MIL clearly is. We therefore sought to further investigate the role of the OM 1) as a key cell structure of potential importance in mediating MIL-based binding and capture of cells and 2) in protecting gram-negative cells against potential MIL toxicity.

Example 8

Evaluation of Capture and Recovery of Wild Type and Mutant Salmonella Minnesota Strains Using the Ni(II) MIL To further evaluate the importance of the OM to serve as a surface to which the MIL can bind and as a protective layer from potentially deleterious activities of the Ni(II) MIL, capture and recovery of two physiological variants of S. Minnesota was performed. The strains compared were S. Minnesota SLH 157 (wild type, functional OM) and S. Minnesota mR613 (OM mutant). S. Minnesota mR613 is considered a "deep rough" mutant, possessing a truncated OM core. Compared to the wild type, cells with a truncated OM are dramatically more susceptible to damage from antimicrobial agents or chemically harsh environments. To study the effect of the Ni(II) MIL exposure on the recovery of wild type and mutant strains of S. Minnesota, a 1 mL aliquot of TSB was inoculated with 1×10$^5$ CFU mL$^{-1}$ of bacteria and spiked with 15 µL of the Ni(II) MIL. MIL-based extraction was performed and 10 µL aliquots of the back-extraction solution were enumerated using TSA and BSA plates. Average CFU counts were compared to a standard that was not exposed to the Ni(II) MIL. Extraction and recovery of S. Typhimurium was also assessed. Enrichment factors were calculated. Table 3 shows enrichment factors for S. Typhimurium, S. Minnesota SLH 157 (wild type) and S. Minnesota mR613 (mutant).

TABLE 3

| Strain | Enrichment Factor (TSA) | Enrichment Factor (BSA) |
|---|---|---|
| S. Typhimurium | 10 | 14 |
| S. Minnesota SLH 157 | 17 | 11 |
| S. Minnesota mR613 | 4 | * |

* For both the standard and the MIL-treated cells, no growth was observed on BSA using the S. Minnesota mR613 "deep rough" mutant strain.

While the extraction efficiency using the Ni(II) MIL was greatly reduced for *S. Minnesota* mR613, capture and recovery of viable cells was observed on TSA. As expected, no growth of mR613 was seen on BSA due to the inherent susceptibility of this OM mutant to selective agents. Likewise, growth of the *S. Minnesota* mR613 standard was observed on TSA but not on BSA.

Our ability to capture this mutant strain demonstrates two key points: 1) the Ni(II) MIL has the capacity to capture and concentrate a strain of *S. Minnesota* that displays a drastically different external surface than wild type cells, and 2) the post-capture growth behavior of this physiologically sensitive strain suggests that the Ni(II) MIL capture process is not overtly antimicrobial. Apparent absence of a toxic impact for the Ni(II) MIL on the "deep rough" mutant *S. Minnesota* strain may result from a lack of intrinsic chemical toxicity, from low diffusivity of the hydrophobic MIL across whatever remaining barrier is offered by this strain's truncated OM, the tendency of the insoluble, hydrophobic MIL to quickly sequester itself into large, non-diffusible aggregate structures in aqueous media, or any combination of these potential phenomena. These data suggest that gram-negative cell surface molecular diversity and character are likely important factors mediating successful cell binding and capture by MILs.

Example 9

Capture and Recovery of Seven Representative DNA Subgroups of *Salmonella* and Eight Strains of *E. coli* O157:H7

In order to explore the broader utility of our approach, evaluation of additional cell types is needed. We began this extended evaluation of the Ni(II) MIL with seven representative DNA subgroups of *Salmonella* and eight strains of *E. coli* O157:H7. Briefly, a 1 mL aliquot of TSB was inoculated with $1\times10^6$ CFU mL$^{-1}$ of bacteria, and spiked with 15 μL of the Ni(II) MIL. MIL-based extraction was performed and 10 μL aliquots of the back-extraction solution were enumerated using TSA and BSA plates (*Salmonella*) or TSA plates (*E. coli* O157:H7). Initially, we examined MacConkey Agar with Sorbitol (SMAC) as a common selective medium for parallel evaluation of injury in *Salmonella* and *E. coli* O157:H7, but *Salmonella* did not grow well on this medium (data not shown). We later determined that VRBGA was a suitable common medium for this purpose and used this in our statistical analysis. Average CFU counts were compared to standards that were not exposed to the Ni(II) MIL. Enrichment factors were calculated for *Salmonella* on both non-selective (TSA) and selective agars (BSA) and for *E. coli* O157:H7 on non-selective agar (TSA). Table 4 shows enrichment factors for seven representative DNA subgroups of *Salmonella* and eight strains of *E. coli* O157:H7. Note: As BSA is a *Salmonella*-specific agar *E. coli* O157:H7 was not plated to BSA in this example.

TABLE 4

| Strain | Enrichment Factor (TSA) | Enrichment Factor (BSA) |
| --- | --- | --- |
| *S. enterica* subsp. *salamae* | 12 | 9 |
| *S. enterica* subsp. *diarizonae* | 7 | 11 |
| *S. enterica* subsp. *houtenae* | 8 | 8 |
| S. Typhimurium | 8 | 6 |
| *S. bongori* | 4 | 4 |
| *S. enterica* subsp. *arizonae* | 3 | 2 |
| *S. enterica* subsp. *indica* | 3 | 4 |
| *E. coli* O157:H7 N192-6-1 | 9 | — |

TABLE 4-continued

| Strain | Enrichment Factor (TSA) | Enrichment Factor (BSA) |
| --- | --- | --- |
| *E. coli* O157:H7 N549-3-1 | 8 | — |
| *E. coli* O157:H7 N192-5-1 | 7 | — |
| *E. coli* O157:H7 N886-71 | 4 | — |
| *E. coli* O157:H7 N366-2-2 | 4 | — |
| *E. coli* O157:H7 N317-3-1 | 4 | — |
| *E. coli* O157:H7 N336-4-1 | 3 | — |
| *E. coli* O157:H7 N405-5-8 | 2 | — |

Our results for capture of the various strains of *Salmonella* and *E. coli* O157:H7 show that all strains of both pathogens could be captured to some degree, when plated onto TSA. *Salmonella* strains representing the seven DNA subgroups belonging to this genus also showed very similar results when plated to BSA (Table 4), suggesting a lack of MIL-imparted injury. To delve beyond superficial visual interpretation of the data, we evaluated a subset of the strains thus far examined and applied statistical analyses to determine 1) whether capture of bacteria varied significantly as a function of strain and 2) if selective agars used revealed the presence of MIL-conferred injury. Our analysis confirmed significant serotype or strain effects for capture of *Salmonella* (p-value<0.0001) and *E. coli* O157:H7 (p-value=0.0721). Regarding MIL-conferred injury, no significant differences (p-value=0.4491) were seen between TSA and VRBGA for recovery of *E. coli* O157:H7, indicating that for this agar pairing, no injury could be detected. Interestingly, while no statistically significant differences (p-value=0.7248) were seen for *Salmonella* serovars on TSA or BSA (i.e. no detectable injury), recovery of *Salmonella* on VRBGA was significantly lower than on TSA (p-value=0.0004). These results suggest that the choice of selective agar is important for both revealing the presence of injury and for informing practical application of MIL-based capture for cultural detection, especially if selective agars are to be used. Comparing the two selective agars, VRBGA contains two selective agents—crystal violet and bile salts, while the sole selective agent in BSA is brilliant green dye. Bile salts are generally agreed to be membrane-active amphiphilic "detergents", and gram-negative bacteria with an intact OM can exclude crystal violet from the cell, avoiding its deleterious effects. It is possible that the barrier function of the OM is altered in some way through its interaction with the MIL during capture, that VRBGA's bile salts and crystal violet act cooperatively on the impaired OM and that *Salmonella* is more susceptible to these effects than *E. coli* O157:H7. It is important to note that BSA is a robustly selective agar. The fact that MIL-exposed *Salmonella* serovars were not impaired for growth on BSA indicates that MIL-based capture can be paired with selective plating onto this medium without interference from the capture process.

Example 10

Comparison of the Initial Wash and Full MIL Extraction Procedure on the Recovery of S. Typhimurium Although all of the strains assessed were capable of being enriched by the MIL, some species were physically enriched to greater extents than others with extraction. In order to further examine the cause for this finding, the number of captured cells lost to the wash solution was investigated. The wash step is performed after the MIL enrichment step in order to remove any incidentally-adsorbed bacteria prior to back-extraction. It is hypothesized that the cells with lower enrichment factors have lower affinities for the MIL and are therefore lost in greater number to the wash solution than those having higher enrichment factors. To test this, five different *Salmonella* strains exhibiting varying degrees of enrichment in initial experiments were examined. The percent-loss during the wash step ranged from 47-79%. Table 5 shows percent-loss of cells to wash, relative affinity for MIL and $E_F$ of select *Salmonella* spp. $E_F$ data from Table 4 for three overlapping *Salmonella* strains are superimposed to highlight trends in percent-loss, relative affinity and $E_F$. The data for *S. Minnesota* mR613 (79% cell loss to wash) support the conclusion that the lower $E_F$ values observed for this strain result from lower affinity to the MIL, rather than from antimicrobial effects.

TABLE 5

| Strain | Percent-Loss[a] | Relative Affinity for MIL[b] | $E_F$ TSA/BSA[c] |
|---|---|---|---|
| S. enterica subsp. diarizonae | 47 ± 7 | +++++ | 7/11 |
| S. Typhimurium | 53 ± 3 | ++++ | 8/6 |
| S. Minnesota SLH 157 | 59 ± 3 | +++ | — |
| S. Minnesota mR613 | 69 ± 5 | ++ | — |
| S. enterica sub sp. arizonae | 79 ± 1 | + | 3/4 |

[a]Percent-loss was calculated by dividing the counts obtained from the wash solution by the sum of the counts of the wash and back-extraction solution, multiplied by 100.
[b]Relative affinity (RA) for MIL assumes higher losses during wash step are due to lower cellular affinity for the MIL.
[c]$E_F$ data from Table 4 for both TSA and BSA are provided here to show parity in RA- $E_F$ trends for select *Salmonella* spp.

This experiment provides evidence that differences in $E_F$ values for the various bacteria tested could be due to intrinsic differences in affinity for the MIL extraction phase. If this is true, bacteria with lower affinities for the MIL may be weakly bound, and are therefore easily removed by the wash step compared to the strains with higher observed enrichment factors.

Example 11

Capacity of the Ni(II) MIL for Capture of Other Members of the Family Enterobacteriaceae of Food Safety, Clinical or Agricultural Significance Our results show that all of the additional Enterobacteriaceae examined here could be concentrated from aqueous suspension using the Ni(II) MIL. These bacteria are ranked in descending order according to $E_F$, with *P. eucalypti, K. aerogenes* and *P. carotovorum* pv. *carotovorum* yielding much higher $E_F$ than seen with other bacteria tested. Table 6 shows enrichment factors for other enterobacterial strains.

TABLE 6

| Strain | Enrichment Factor |
|---|---|
| P. eucalypti 299R[a] | 169 |
| K. aerogenes ATCC 29940[b] | 71 |
| P. carotovorum pv. carotovorum[a] | 24 |
| C. sakazakii 01088P[b] | 12 |
| E. amylovora Ea935[a] | 10 |
| Y. enterocolitica ATCC 2371 [b] | 5 |
| Y. enterocolitica ATCC 9160 [b] | 5 |

[a]$E_F$ determined using Columbia Agar.
[b]$E_F$ determined using Tryptic Soy Agar.

Our work with additional enterobacterial strains of concern clearly highlights the broader utility of the Ni(II) MIL for capture and concentration of these economically important bacteria. Of particular interest was the extremely high $E_F$ result seen for *P. eucalypti* 299R (formerly *P. agglomerans* 299R), which yielded an $E_F$ of 169—approximately 20× greater than that for many of the other enterobacteria examined in this study. The reason for this result is not yet known, although this strain was visually more pigmented than other enterobacteria tested, suggesting a possible connection between carotenoid content and higher binding. Another potential reason for this result may be the formation of "symplasmata" by this strain. Symplasmata are multicellular aggregates (hence this strain's previous epithet "agglomerans", meaning "forming into a ball") that confer competitive advantages to this bacterium. Symplasmata are comprised of many (potentially hundreds of) clonal cells bound within a thick polysaccharide envelope and are known to form in laboratory media, as well as on plant surfaces. It is reasonable to suggest that our remarkable $E_F$ results for *P. eucalypti* 299R could be due to the presence of symplasmata in our culture of this organism. If this is the case, it would demonstrate the exciting potential of our MIL-based approach to capture and concentrate unique multicellular structures of importance to plant health in additional to individual bacterial cells.

The broad applicability of MIL-based capture and concentration to enterobacteria occurring across the production-to-consumption continuum underlines the potential value of this approach to rapid detection methods aimed at mitigating human disease and preventing crop loss. A brief overview of the significance of the bacteria included in this study to agriculture, food safety and human health is provided below. Foodborne and clinically-important enterobacteria include *Cronobacter sakazakii*, which is problematic in powdered infant formula, causing neonatal infections with mortality as high as 40%. Pathogenic *Escherichia coli* can be divided into several important groups based on pathology, with *E. coli* O157:H7 and five other Shiga toxin-forming *E. coli* (STEC) forming the "Big Six"—bacteria regarded by regulatory agencies as "zero tolerance" food adulterants. In 2018 there were two multistate outbreaks of *E. coli* O157:H7 in Romaine lettuce; at the end of 2019, another such outbreak and recall of Romaine lettuce from the Salinas Valley occurred, affecting 167 people in 27 states. *Salmonella* spp. represent one of the most pervasive bacterial threats to the food system, in terms of the estimated number of infections and breadth of foods affected. The genus *Yersinia* includes *Y. pestis*—the cause of the plague (the "Black Death") and *Y. enterocolitica*, which is transmitted through undercooked pork infections. On the clinical side, carbapenem-resistant Enterobacteriaceae, which includes some *Klebsiella* strains, has been prioritized as an "urgent threat" by the Centers for Disease Control and Prevention (CDC), meaning that urgent and aggressive action is required to counter this threat to public health. Enterobacterial plant pathogens include *Enwinia amylovora*, the cause of fire blight, which can decimate entire apple or pear orchards. *Pantoea* spp. cause infections in both humans and plants and, like *Cronobacter*, have been isolated from powdered infant formula. *P. eucalypti* is an epiphyte on many plants and causes disease in others, including pea, sweet corn and wheat, while *Pantoea stewartii* causes wilt in corn and seed rot in cotton, among others. *Pectobacterium carotovorum* pv. *carotovorum* is a ubiquitously distributed pathogen causing bacterial soft rot in various plants and blackleg disease in potato The family Enterobacteriaceae is a large group of genetically- and physiologically-related gram-negative bacteria existing in a wide variety of niches of importance to and overlapping with human activities. Although there is considerable diversity within the family, these bacteria share several structural and biochemical features that are of importance in defining their surface characteristics, and therefore, their potential to interact with MILs. These are discussed further below.

As gram-negative bacteria, the Enterobacteriaceae all possess a lipopolysaccharide outer membrane (OM) comprised of a lipid element, a conserved oligosaccharide core and a highly variable polysaccharide sequence, termed the "O-antigen". The OM serves as barrier to the diffusion of toxic compounds such as antibiotics, and the O-antigen plays roles in avoiding phagocytosis and protecting cells against complement-mediated cell lysis. There are two notable types of O-antigen variants in *Salmonella* and other enterobacteria—"rough" and "mucoid". Rough mutants have a truncated LPS and do not possess an O-antigen; mucoid variants have an O-antigen, but it is obscured by a capsule that obscures it from immunologic detection. The surface antigens displayed by the *Salmonella* strains representative of the seven DNA subgroups that comprise this genus are shown in Table 7. This table highlights the considerable surface molecular diversity of the *Salmonella* strains used in this study. Despite this molecular diversity and its expected impact on diversity of cell surface charge, all of these salmonellae could be captured by the Ni(II) MIL, with 4 of the 7 strains displaying $E_F$ on par with what we have previously observed for S. Typhimurium and non-pathogenic *E. coli*.

Another feature common to the family, as suggested by the name, is the Enterobacterial Common Antigen (ECA), a polysaccharide repeat structure located in the cell envelope that is linked to maintenance of OM integrity and represents a useful target for detection of enterobacterial strains. Additional cell surface structures that contribute to the molecular and charge diversity of enterobacteria include porins—transmembrane transport proteins, which also act as receptors for bacteriophage, fimbriae (also referred to as adhesins or pili)—stiff, hair-like appendages uniformly distributed across the cell surface and that mediate bacterial binding to host cells, and flagella. Flagella (H-antigen) are whip-like structures that confer cell motility and whose number and surface arrangement may vary according to cell type.

TABLE 7

| Strain | DNA Subgroup | Somatic (O) Antigen | Flagellar (H) Antigen Phase 1 | Phase 2 |
|---|---|---|---|---|
| S. Typhimurium ATCC 14028 | I | 4, 5, 12 | i | 1, 2 |
| S. salamae SA4406 | II | 1, 9, 12 | 1, w | e, n, x |
| S. arizonae SA4407 | IIIa | 51 | z(4), z(23) | (—) |
| S. diarizonae SA4408 | IIIb | 6, 7 | 1, v | z(53) |
| S. houtenae SA4409 | IV | 45 | g, z(51) | (—) |
| S. indica SA4411 | VI | 1, 6, 14, 25 | a | e, n, x |
| S. bongori SA4410 | V | 66 | z(41) | (—) |

Key cell surface antigens—lipopolysaccharide-based somatic (O) and flagellar (H) antigens are listed according to the Kauffmann-White scheme (Grimont and Weill, 2007). These data highlight the antigenic diversity (surface biochemical complexity) of these representatives of the seven DNA subgroups comprising the genus *Salmonella*, which all, to some degree, were captured by the Ni(II) MIL. "Diphasic" *Salmonella* are capable of expressing both Phase 1 or Phase 2 flagellar antigens in coordinate, "either/or" fashion. "Monophasic" *Salmonella*—those that only express Phase 1 flagellar antigens—are indicated by "(—)".

Example 12

Investigating Mechanisms for Observed Antimicrobial Activities of the Dy(III) MIL Incorporation of a rare-earth metal into the MIL structure is of significant interest as these metals possess greater magnetic moments. In principle, this should allow for improved magnetic manipulation compared to transition metal-based MILs. However, when the Dy(III) MIL was previously examined for the capture of bacteria, recovery of viable cells was not observed. To further explore these results and to determine if they result from intrinsic antimicrobial activity of this MIL, bacterial suspensions of S. Typhimurium were exposed to various structural components of the MIL.

Within 30 s of vortexing a cell suspension to which 15 μL of the Dy(III) MIL was added, we observed extensive flocculation and no growth after plating, suggesting that this MIL may have intrinsic antimicrobial activity, resulting in rapid cell lysis.

To gain further insight into this phenomenon, the effect of free elemental dysprosium was evaluated by subjecting the cells to 0.1 mM and 1.0 mM solutions of $DyCl_3$. The cells were exposed to the metal salt solutions for 30 s and subsequently plated on selective and non-selective media. Results shown in FIG. 9 demonstrate that growth can be observed on both types of plates. However, substantially lower counts were observed on BSA than TSA, particularly at the higher $DyCl_3$ concentration.

The partially inhibitory effects of $DyCl_3$ indicates that the coordinated metal itself may be partially responsible for the observed deleterious effects of the MIL. While the metal did show cytotoxicity, it cannot be completely responsible for the Dy(III) MIL's effect on the cells, as no flocculation was seen and growth was still observed. Since both the Ni(II) and the Dy(III) MILs contain identical cations ($[P_{6,6,6,14}^+]$), the role of the anion structure was evaluated. The anion of the Dy(III) MIL contains one additional hexafluoroacetylacetonate ligand than the Ni(II) MIL (FIG. 7), making the coordination geometry of the two complexes different. To test the effects of the anion structure, cells were subjected to 10 mg of the Dy(III) ammonium salt. After a 30 second vortex, similar flocculation was observed as when the cells were exposed to the native Dy(III) MIL. After plating and 24 h incubation, no growth was seen on either TSA or BSA. These results, combined with those from $DyCl_3$ exposure experiments, provide strong evidence that the anion structure is largely responsible for the antimicrobial effects of this MIL.

Example 13

Comparison of Positive- and Air-Displacement Pipettes for MIL Delivery

Figures 9, 10:
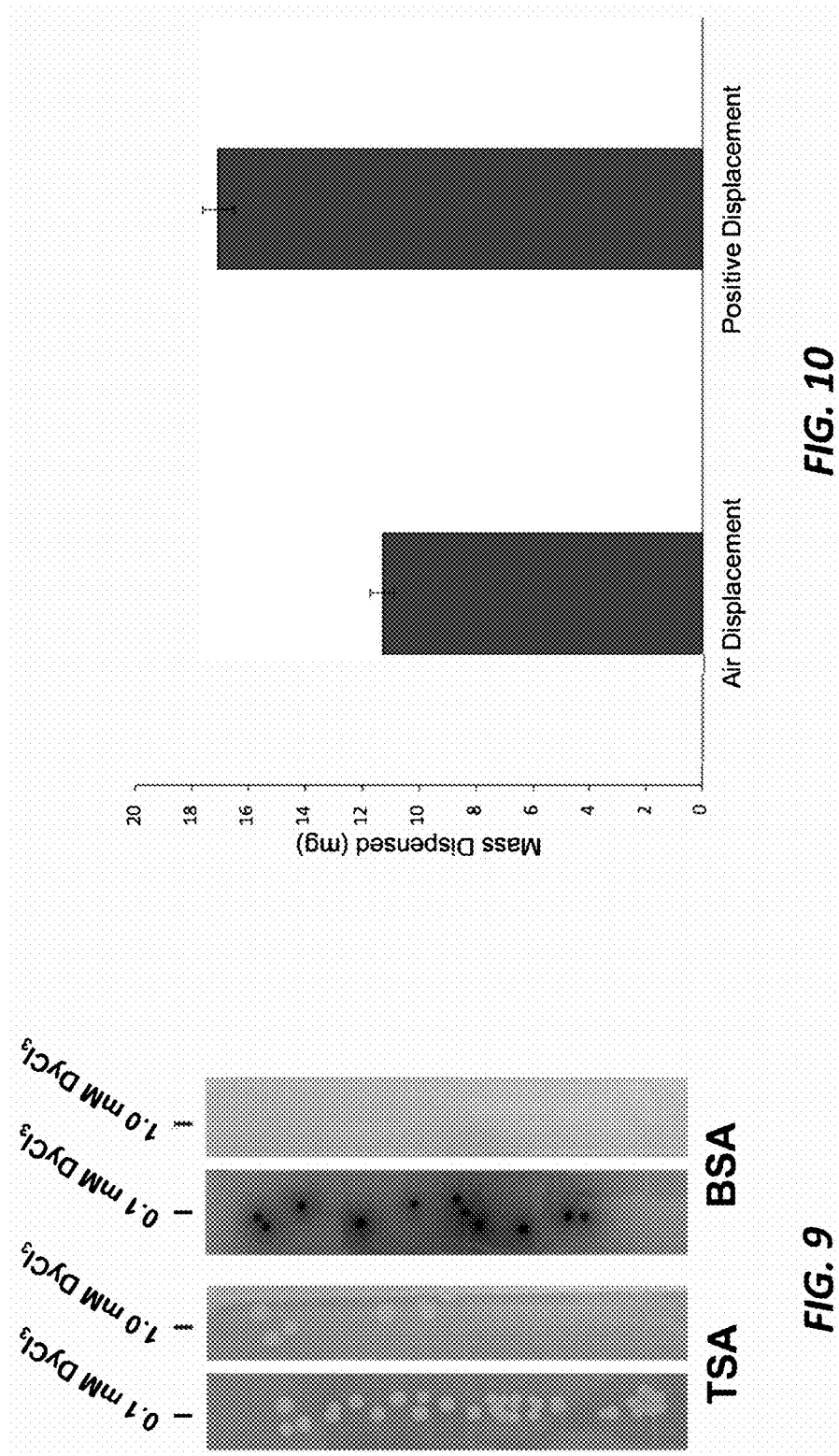
FIG. 9 shows recovery of *Salmonella* Typhimurium following 30 s exposure to 0.1 mM and 1.0 mM DyCl$_3$. Viable CFU counts recovered on non-selective TSA (left) and selective BSA (right) from the DyCl$_3$-exposed cells following a 30 s treatment.
FIG. 10 shows evaluation of Ni(II) MIL delivery using air displacement (AD) and positive displacement (PD) pipettes. The average mass in mg of Ni(II) MIL dispensed using the AD and PD pipettes is reported. The PD pipette was able to deliver a substantially greater mass of Ni(II) MIL (17.1±0.6 mg) compared to the AD pipette (11.3±0.4 mg).

We found that handling and delivery of the Ni(II) MIL was challenging when using traditional air-displacement (AD) pipettes, due to both MIL viscosity and incomplete delivery of aspirated MIL. We therefore sought to compare AD pipetting with piston-driven positive-displacement (PD) pipetting and the impact, if any, on bacterial extraction results. Briefly, 15 μL of MIL was delivered from each pipette and weighed using an analytical balance (n=3). The PD pipette was able to deliver a substantially greater mass of MIL (17.1±0.6 mg) compared to the AD pipette (11.3±0.4 mg), with similar reproducibility (FIG. 10). To test whether or not this difference impacted extraction performance, extractions were performed, using each pipette to dispense 15 μL of MIL. The calculated $E_F$ did not differ according to the pipetting method used, despite the disparity in the amount pipetted.

Although the PD pipette delivered substantially more of the target 15 μL volume of Ni(II) MIL, enrichment factors from bacterial extractions were not affected by this ~6 μL difference added to bacterial suspensions. These results suggest that, for the number of bacteria present in standardized suspensions, the amount of MIL used is above the carrying capacity of the MIL (the amount at which it is saturated and cannot bind additional bacteria). Apart from the performance equivalence of the two methods, PD pipetting was faster, easier and did not result in loss of MIL due to adherence to the pipette tip, which could be economically advantageous, especially for high-throughput applications.

Example 14

Figure 11:
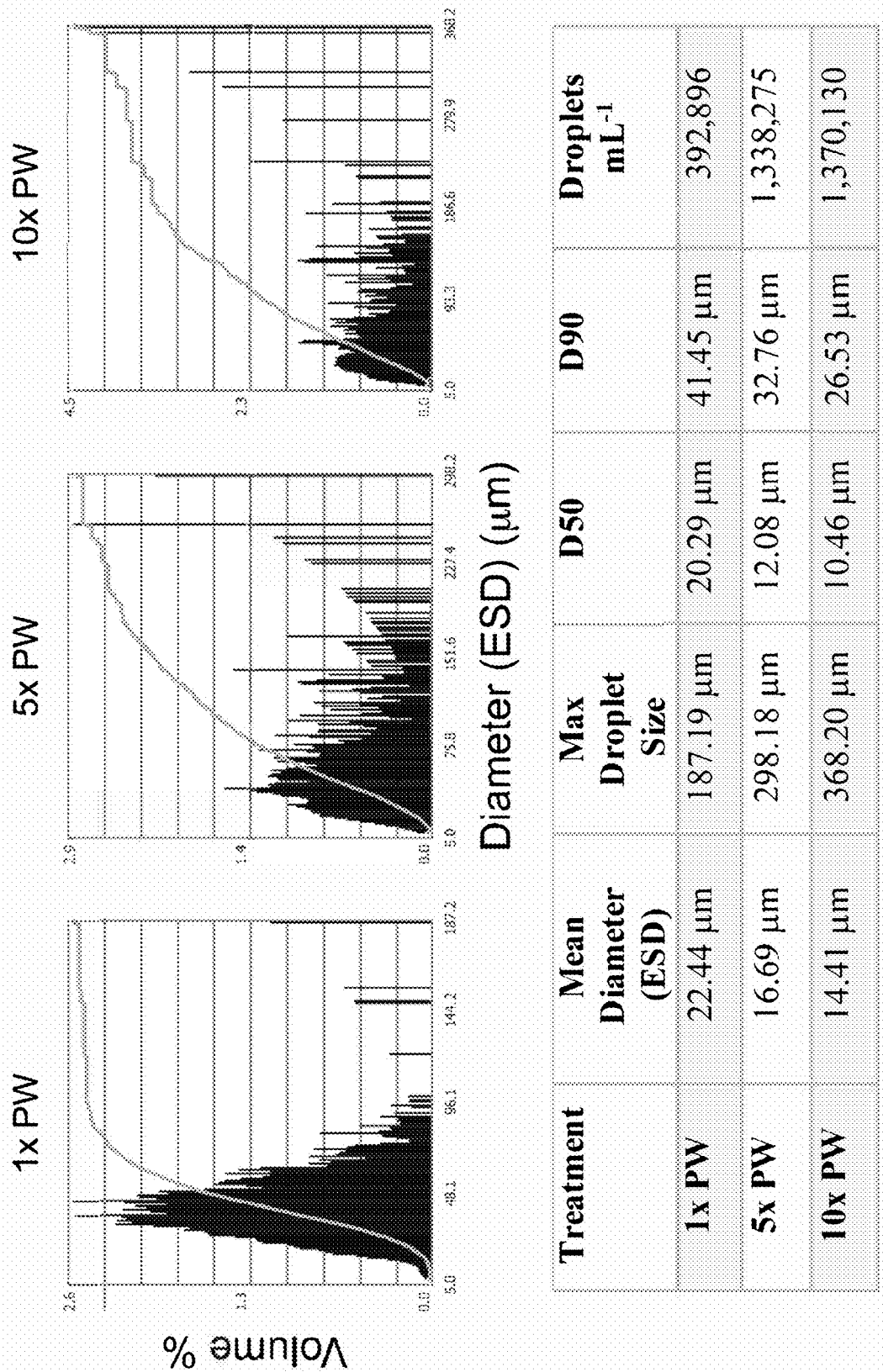
FIG. 11 shows visualization of MIL-bacteria interactions via Flow Imaging Microscopy (FIM). Key metrics from FIM analyses of Ni(II) MIL suspension characteristics under three different concentrations of peptone water (PW) are shown. VISUALSPREADSHEET® software (v. 5.0, Fluid Imaging Technologies) was used to analyze sample data. A trend toward smaller droplet size and greater extremes of maximum droplet size was seen as the ionic complexity of the medium increased.

Characterization of MIL Dispersions Under Differing Ionic Conditions Using Flow Imaging Microscopy As summed in FIG. 11, FIM measurements of Ni(II) MIL dispersions in aqueous samples of increasing ionic complexity (1×, 5× and 10× PW) showed that as solute concentration increased, droplet size decreased. As would be expected, these trends towards smaller particle sizes were directly correlated to increasing numbers of total particles per unit volume (particles $mL^{-1}$). An additional trend towards larger outlier droplets (overall droplet heterogeneity) was seen as ionic complexity increased.

As the ionic complexity of PW solutions increased, droplet size decreased, with trends toward smaller droplet size resulting in a commensurate trend towards higher droplet count (droplets $mL^{-1}$). The effect was not completely uniform, however, as overall sample heterogeneity, as characterized by increasing outlier particle size, increased along with increasing solute concentration. It is not clear how applicable the principles of traditional oil-in-water emulsion chemistry are to our consideration of MIL behavior in aqueous suspension, as the MILs, while hydrophobic, are not technically "oils". Further, because they are comprised of ion pairs, they are chemically inhomogeneous. As such, the term "emulsion", which also implies an inherently stable structure, can only be loosely applied to their behavior when they are mechanically dispersed in aqueous media.

Of importance to their application as sample preparation reagents, mechanically dispersed MILs form a short-lived "cloud" of particles capable of interacting with different charged species within aqueous matrices such as foods, including solutes and suspended particles, followed by eventual density-based coalescence at the bottom of the sample vial. Because they are paramagnetic, their separation from the aqueous phase, along with any bound species, can be hastened in the presence of a magnet. Our results with differing concentrations of PW suggest that interactions with and partitioning of charged solutes, such as NaCl and the peptidic and amino acid components of this medium into the MIL phase affect droplet size, and subsequently, the number of droplets $mL^{-1}$.

These interactions of the MIL with sample components may have important impacts on the efficacy of the MIL as a bacterial capture reagent. On one hand, a trend towards smaller droplets and greater overall numbers of droplets per unit volume is expected to favor more efficient collision with colloidal particles such as bacteria. However, we also hypothesize that higher sample ionic complexity may compete with bacterial binding, if such binding is governed solely by electrostatic binding effects. The concentrations of PW used here include levels of NaCl beyond which we would expect the Ni(II) MIL to be effective as a bacterial capture reagent in foods. For example, we previously used a medium containing only 1% NaCl for desorption of captured bacteria from the MIL phase during our "back extraction" procedure. To contextualize these salt levels in terms of model food systems, we used nutritional content panel information from store-bought chicken broth, a perceivably salty food, to calculate its NaCl content as ~0.2%—well below the 1% we used for MIL-desorption. Still, the use of PW-based model matrix formulations yielding NaCl concentrations ranging from 0.5% (food-like) to 5% provided new insights into MIL dispersion/medium composition trends that may inform applications of MILs in various sample types, including non-food samples.

It is not clear what the trend towards larger outlier droplets in the presence of higher ionic concentration indicates, as this could result from poorer initial MIL dispersion or from faster coalescence. We have used nonionic polyoxyethylene detergents such as Brij 700 to modify dispersion characteristics of MILs. This approach may be useful for ensuring greater droplet homogeneity, although the impacts of these detergents on extraction characteristics of MILs is unknown. Presumably, because they are nonionic in nature and our working hypothesis is that charge-based interactions are important in governing the partitioning of bacterial surface structures into MILs, they would not interfere with extraction behavior. However, we are also exploring other potential modes through which MILs might interact with bacteria, such as hydrophobic interactions. If these also play a role, the hydrophobic aliphatic chains of such detergents could partition into the MIL and affect extraction behavior. In the absence of such information, purely physical approaches for promoting droplet homogeneity, which could help reduce inter-experimental variability, such as the use of conical or baffled vials for sample dispersion may also be valuable, as they would not result in or depend on chemical modification of the MIL.

Example 15

Figure 12A:
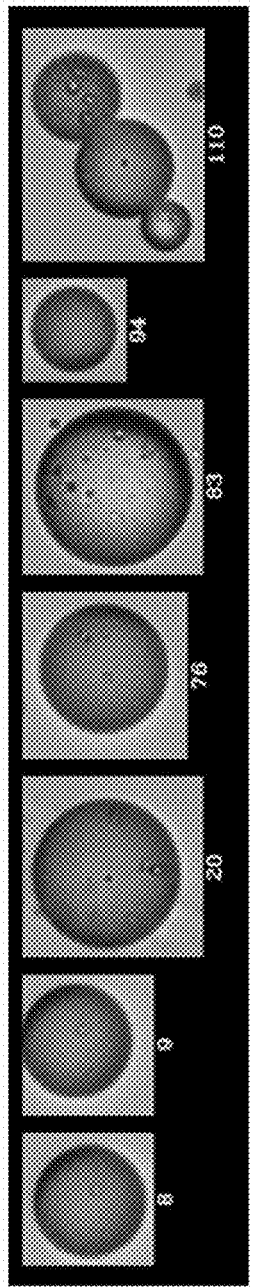
FIG. 12A-FIG. 12C show the general appearance of Ni(II) MIL suspended in aqueous media of increasing ionic complexity, without added bacteria.
Figure 12B:
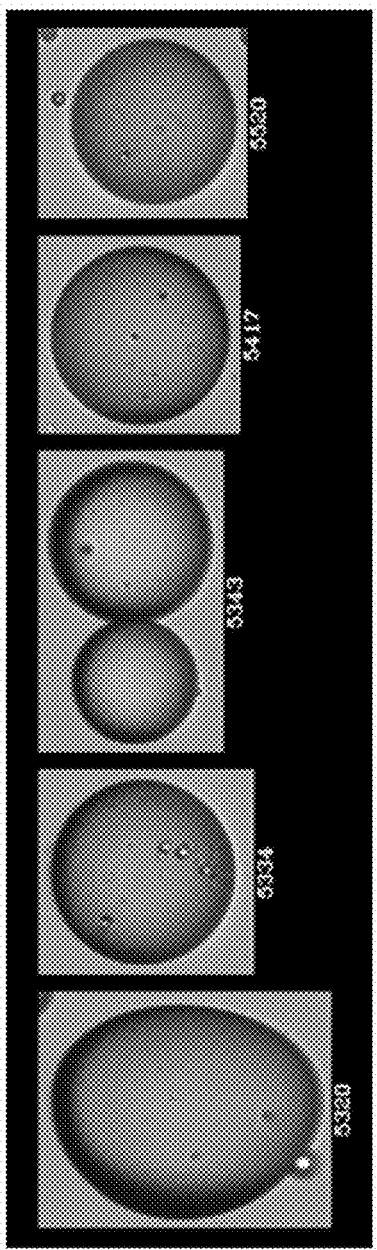
Figure 12C:
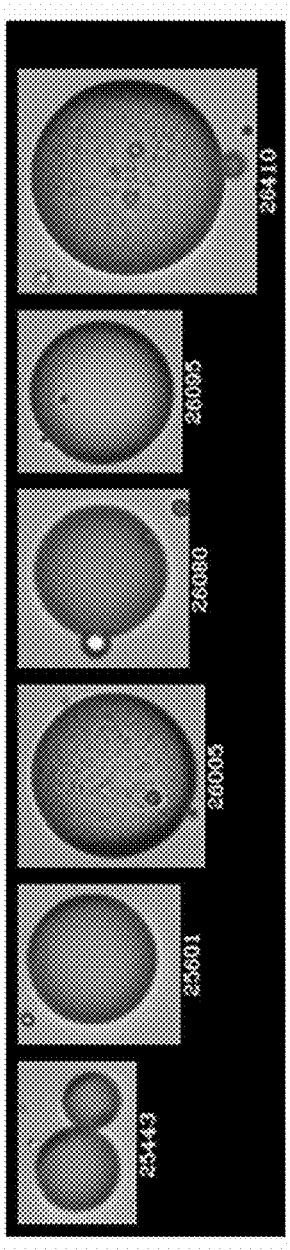
Figure 13:
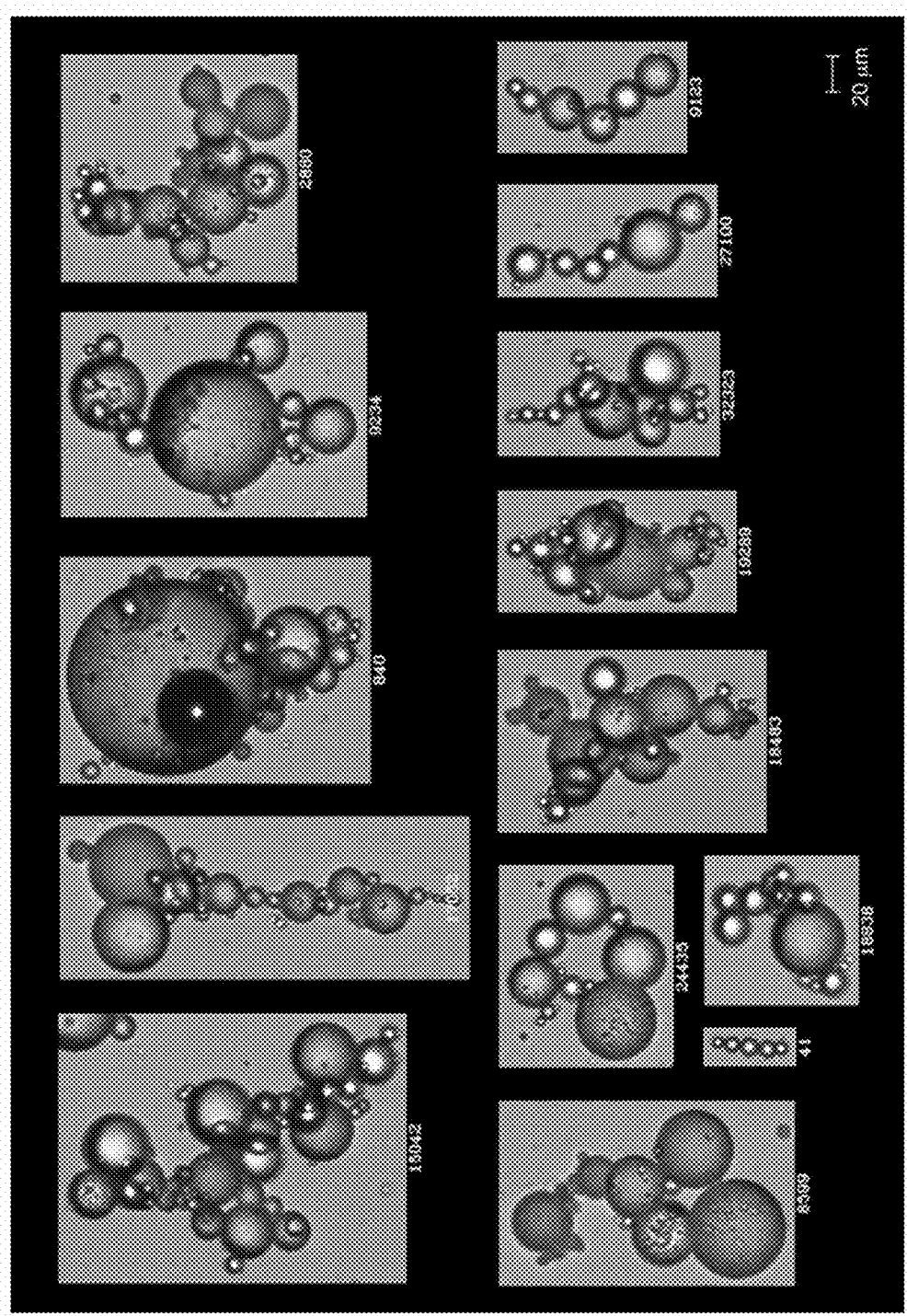
FIG. 13 shows *Serratia marcescens*-Induced Aggregation of Ni(II) MIL Droplets. The presence of *S. marcescens* resulted in a dramatic shift in the presentation of Ni(II) MIL droplets in 1× peptone water (PW). In the presence of *S. marcescens*, MIL droplets formed large and complex aggregates, which may suggest a physical mechanism for MIL-based concentration of bacteria.

*Serratia marcescens*-Induced Aggregation of Ni(II) MIL Droplets—Implications for MIL-Mediated Bacterial Concentration In general, cell-free suspensions of Ni(II) MILs under various conditions of ionic complexity yielded distributions of individual or minimally-aggregated droplets (FIG. 12). In some cases, apparent surface granularity of MIL droplets suggested a MIL coalescence mechanism similar to oil-in-water emulsions through aggregation and merging of smaller particles. In the presence of *S. marcescens* cells, however, we observed a radically different presentation of MIL droplets (FIG. 13), with the formation of multi-droplet aggregates and chains under the "food-like" conditions of 1× PW (0.5% NaCl, 1% peptone), which may suggest a physical mechanism for MIL-based concentration of bacteria.

Figure 14:
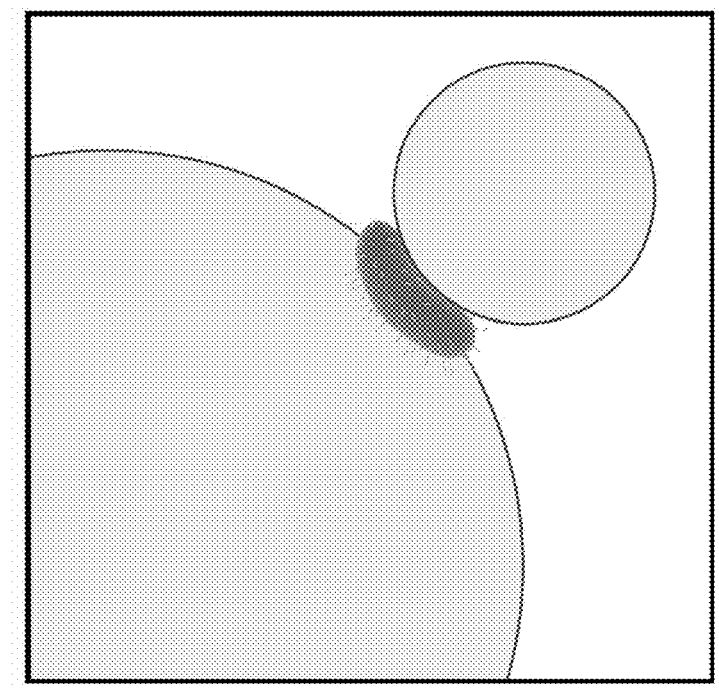
FIG. 14 shows a hypothesized mechanism for cell-mediated MIL aggregation. Based on the radically different aggregation behavior of the Ni(II) MIL when *S. marcescens* is present, we hypothesize that the structures (chains and other aggregates) observed result from interfacial "sandwiching" effects, where bound bacterial cells serve to link and bridge adjacent MIL droplets, leading to cell-mediated aggregation and gravimetric deposition of MIL-cell complexes at the bottom of the sample tube after vortexing.

The dramatically different presentation of MIL particles in the presence of *S. marcescens* was an unexpected result. Although the FlowCam magnification used (10×) was not sufficient for visualizing individual cells, we interpret the formation of large aggregates and chains in the presence of *S. marcescens* as the result of cell-mediated "bridging" of individual droplets. We expect that, although *S. marcescens* produces a hydrophobic pigment (prodigiosin) and is known to avidly partition into hydrocarbons such as n-hexadecane, as a bacterium, its native environment is largely aqueous and partitioning inside of MIL droplets would not be energetically favorable. We hypothesize that cells of *S. marcescens* are able to bind to and partition into MIL droplet surfaces, leaving one side of the organism in contact with the MIL and the other side exposed to the environment. Subsequent collision with and binding to suspended MIL particles creates a MIL-bacterium-MIL "sandwich" (FIG. 14), which, when repeated, results in the formation of the multi-droplet aggregates and chains we observed. These observations may provide a general model for MIL-bacteria interactions.

The invention is being thus described. It will be obvious that the same may be varied in many ways. Such variations are not to be regarded as a departure from the spirit and scope of the present disclosure and all such modifications are intended to be included within the scope of the following claims.

The above specification provides a description of a method and kit, all of which includes various magnetic ionic liquids to extract viable *Salmonella* bacteria. Since many embodiments can be made without departing from the spirit and scope of the present disclosure, the invention resides in the claims.

extracting the microbes or their diagnostically useful cellular components from the magnetic ionic liquid using an aqueous extracting medium to generate an extracted microbe sample;

detecting the microbes; wherein the detecting is performed by an amplification-based detection method comprising using Recombinase Polymerase Amplification (RPA) on the extracted microbe sample; wherein the RPA is carried out with a power-free heat source comprising a sodium acetate heat pack;

wherein the food sample comprises a liquid food or an aqueous suspension of a solid food, wherein the food sample comprises viable microbes, and wherein the viable microbes comprise gram-negative bacteria, gram-positive bacteria, viruses, or a mixture thereof.

What is claimed is:

1. A method of extracting and detecting microbes in a food sample, comprising:

contacting the food sample with a magnetic ionic liquid (MIL) for the period of a contacting time;

2. The method according to claim 1, wherein the microbes are gram-negative bacteria selected from the group consisting of *Cronobacter sakazakii, E. coli, Klebsiella aerogenes, Pantoea eucalypti, Pantoea stewartii, Pectobacterium carotovorum, Salmonella bongori, Salmonella enterica, Serratia marcescens, Yersinia enterocolitica*, and mixtures thereof.

3. The method according to claim 1, wherein the food sample comprises milk or egg.

4. The method according to claim 1, wherein the extracting medium is a Luria-Bertani-derived nutrient broth comprising more than 10 g/L of tryptone, more than 5 g/L of yeast extract, more than 10 g/L of NaCl, or combination thereof.

5. The method according to claim 1, wherein a volume ratio between the magnetic ionic liquid and the extracting medium is from about 1:5 to 1:15.

6. The method according to claim 1, wherein the RPA on the extracted microbe sample amplifies DNA or RNA of the microbes; and wherein RPA is applied to the extracted microbe sample for amplifying characteristic DNA of the microbes at a temperature of from about 20° C. to about 50° C.

7. The method according to claim 6, wherein the microbes are *Salmonella* and the RPA comprises using a dienelactone hydrolase primer.

8. The method according to claim 6, wherein the RPA comprises using a reverse transcriptase (RT) enzyme for characteristic RNA of the microbes.

9. The method according to claim 1, wherein results of the RPA are visualized using nucleic acid lateral flow immunoassay (NALFIA) or gel electrophoresis.

10. The method according to claim 1, wherein the magnetic ionic liquid comprises a paramagnetic anionic component and a cationic component,
wherein the cationic component has a general formula (I), (IV), or (V)

$$[(PR^1R^2R^3R^4)^+] \quad (I)$$

wherein each of the $R^1$, $R^2$, $R^3$, and $R^4$ is independently an unsubstituted or substituted alkyl;
wherein the paramagnetic anionic component has the following general formula (II), $$[M(Y)_x^-] \quad (II)$$

wherein M is transition metal or rare earth metal ion; and Y is a chelating agent having the general formula (III), (III)

each of the $R^{10}$ and $R^{11}$ are independently a substituted or unsubstituted methyl, phenyl, thiophenyl, napthyl, alkyl, or aryl group; and x is 3 or 4

(IV)

(V)

and wherein Ti comprises Co, Ni, Mn or a combination thereof and Ln comprises Dy, Gd, Ho, or a combination thereof.

11. The method according to claim 10, wherein the MIL has the anionic component of [Co(hfacac)$_3^-$], [Ni(hfacac)$_3^-$], ([Mn(hfacac)$_3^-$]), ([Dy(hfacac)$_4^-$]), ([Gd(hfacac)$_4^-$]), ([Nd(hfacac)$_4^-$]), or combination thereof; wherein hfacac is and has the cationic component of [(PR$^1$R$^2$R$^3$R$^4$)$^+$], wherein each of the $R^1$, $R^2$, $R^3$, and $R^4$ is independently a C$_2$-C$_{20}$ unsubstituted alkyl.

12. The method according to claim 1, wherein the magnetic ionic liquid comprises a paramagnetic cationic component and an anionic component, wherein the anionic component has a general formula (VI) or (VII)

(VI)

-continued
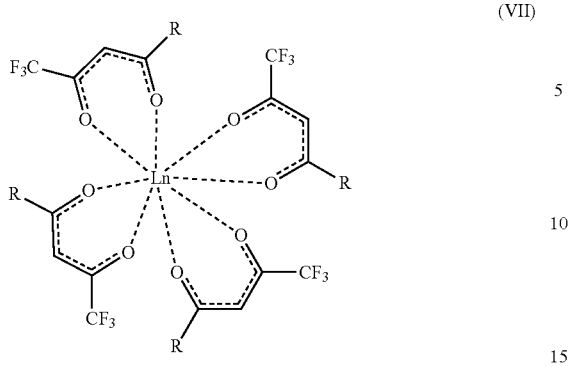
(VII)
wherein R is one or more of the following:
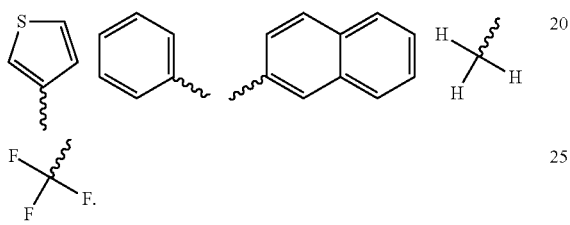
and wherein Ti comprises Co, Ni, Mn or a combination thereof and Ln comprises Dy, Gd, Ho, or a combination thereof.
* * * * *

```
                         SEQUENCE LISTING

<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: Primer

<400> SEQUENCE: 1
gccgggcagc rattattctg catgaa                                    26

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
tggcgtatac gggaaccgta atagca                                    26

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
ctacaagcat gaaatggcag aacagcgtcg                                30

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
caaccagata ggtaggtaat ggaatgacga                                30
```